US012653562B2

(12) United States Patent
Carreel

(10) Patent No.: US 12,653,562 B2
(45) Date of Patent: Jun. 16, 2026

(54) INSERTABLE DEVICE INCLUDING FLEXIBLE CIRCUITRY

(71) Applicant: SENSOME, Massy (FR)

(72) Inventor: Bruno Carreel, Arcueil (FR)

(73) Assignee: SENSOME, Massy (FR)

( * ) Notice: Subject to any disclaimer, the term of this patent is extended or adjusted under 35 U.S.C. 154(b) by 103 days.

(21) Appl. No.: 18/273,233

(22) PCT Filed: Jan. 20, 2022

(86) PCT No.: PCT/EP2022/051281
§ 371 (c)(1),
(2) Date: Jul. 19, 2023

(87) PCT Pub. No.: WO2022/157270
PCT Pub. Date: Jul. 28, 2022

(65) Prior Publication Data
US 2024/0299052 A1    Sep. 12, 2024

Related U.S. Application Data

(60) Provisional application No. 63/139,461, filed on Jan. 20, 2021.

(30) Foreign Application Priority Data

Jul. 12, 2021    (EP) .................................... 21305969

(51) Int. Cl.
*A61B 17/221* (2006.01)
*A61B 17/00* (2006.01)
(Continued)

(52) U.S. Cl.
CPC ...... *A61B 17/221* (2013.01); *A61B 17/00234* (2013.01); *G16H 20/40* (2018.01);
(Continued)

(58) Field of Classification Search
CPC .. H05K 1/028; A61B 17/00234; A61B 17/22; A61B 17/221; A61B 18/14;
(Continued)

(56) References Cited

U.S. PATENT DOCUMENTS

2012/0029343 A1*    2/2012    Wasson ................... H01F 5/003
336/200
2016/0322283 A1    11/2016    McMahon et al.
(Continued)

FOREIGN PATENT DOCUMENTS

CN        105286919 A    2/2016
CN        108209903 A    6/2018
(Continued)

OTHER PUBLICATIONS

European Examination Report dated Apr. 30, 2024, in corresponding European Patent Application No. 21305969.4 (4 pages).
(Continued)

*Primary Examiner* — Mohamed G Gabr
(74) *Attorney, Agent, or Firm* — Andrew J. Tibbett; Greenberg Traurig, LLP

(57) ABSTRACT

Embodiments described relate to a medical device including an invasive probe that, when inserted into a duct (e.g. vasculature) of an animal (e.g., a human or non-human animal, including a human or non-human mammal), may be used to aid in diagnosing and/or treating a lesion of the duct (e.g. a growth or deposit within vasculature that fully or partially blocks the vasculature). The invasive probe may have one or more sensors to sense characteristics of the lesion, including by detecting one or more characteristics of tissues and/or biological materials of the lesion.

20 Claims, 43 Drawing Sheets

(51) Int. Cl.
  *A61B 17/22*    (2006.01)
  *G16H 20/40*    (2018.01)

(52) U.S. Cl.
  CPC ............... *A61B 2017/00022* (2013.01); *A61B 2017/00199* (2013.01); *A61B 2017/00221* (2013.01); *A61B 2017/00238* (2013.01); *A61B 2017/00292* (2013.01); *A61B 2017/0046* (2013.01); *A61B 2017/00477* (2013.01); *A61B 2017/00526* (2013.01); *A61B 2017/00929* (2013.01); *A61B 2017/00951* (2013.01); *A61B 2017/22038* (2013.01)

(58) Field of Classification Search
  CPC ............ A61B 18/1477; A61B 18/1482; A61B 18/1492; A61B 2017/00022; A61B 2017/00026; A61B 2017/00199; A61B 2017/00221; A61B 2017/00238; A61B 2017/00292; A61B 2017/0046; A61B 2017/00477; A61B 2017/00526; A61B 2017/00929; A61B 2017/00951; A61B 2017/22038; A61B 2017/22079; A61B 2017/2215; A61B 2018/00452; A61B 2018/00577; A61B 2018/00875; A61B 2562/164; A61B 2562/166; A61B 2562/182; A61B 2562/222; A61B 5/02007; A61B 5/0536; A61B 5/0537; A61B 5/0538; A61B 5/6851; A61B 2034/101
See application file for complete search history.

(56)      References Cited

U.S. PATENT DOCUMENTS

| | | | |
|---|---|---|---|
| 2017/0100054 | A1 | 4/2017 | Tai et al. |
| 2019/0069949 | A1 | 3/2019 | Vrba et al. |
| 2019/0380651 | A1* | 12/2019 | Carreel ............... A61B 5/0538 |

FOREIGN PATENT DOCUMENTS

| | | | |
|---|---|---|---|
| CN | 110167429 | A | 8/2019 |
| CN | 111511303 | A | 8/2020 |
| JP | 2002-537885 | A | 11/2002 |
| JP | 2012-511963 | A | 5/2012 |
| JP | 2020-512034 | A | 4/2020 |
| WO | 00/51489 | A1 | 9/2000 |
| WO | 2015103580 | A2 | 7/2015 |
| WO | 2018/096182 | A2 | 5/2018 |

OTHER PUBLICATIONS

International Search Report; PCT/EP2022/051281; Date: Apr. 21, 2022; By: Authorized Officer: Emirdag, Eda.

Japanese Office Action date Oct. 7, 2025, from related Japanese Patent Application 2023-543125.

Chinese Office Action date Mar. 25, 2026, from related Chinese Patent Application 202280022771.3.

\* cited by examiner

100

START

102
Insert invasive probe into vasculature

104
Operate invasive probe to determine one or more characteristics of lesion

106
Operate medical device to generate and output treatment recommendation based on lesion characteristics

108
Select treatment option based on treatment recommendation

110
Treat lesion using selected treatment option

END

1300

START

1302
Detect characteristics of lesion,
including composition

1304
Based on composition, select
treatment option to recommend

1306
Monitor performance of
treatment option

1308
Output information on
status of treatment

1310
Based on status, generate and output recommendations on
manner in which to perform treatment

END

1400

START

1402
Receive characteristics of lesion

1404
Compare characteristics to
conditions for treatment options

1406
Output recommendation of treatment
options based on comparison

END

1520

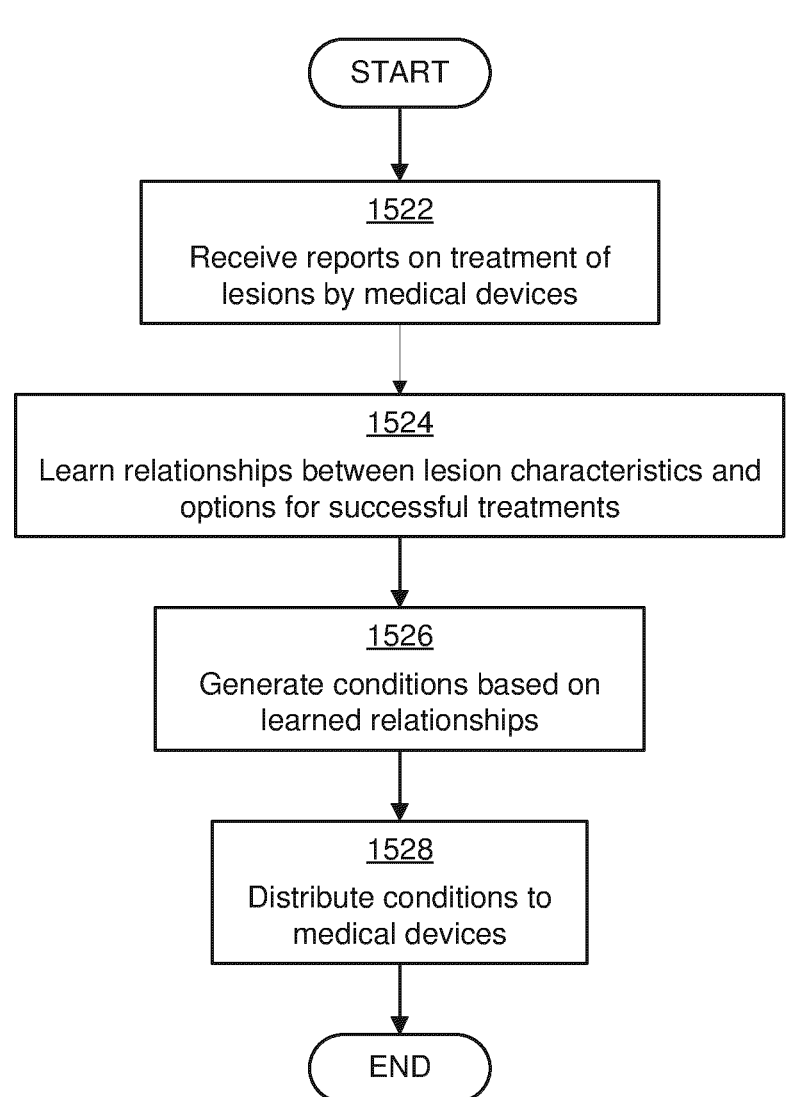

```
        ┌─────────────┐
        │    START    │
        └──────┬──────┘
               │
               ▼
   ┌───────────────────────────┐
   │           1522            │
   │  Receive reports on       │
   │  treatment of             │
   │  lesions by medical       │
   │  devices                  │
   └───────────┬───────────────┘
               │
               ▼
 ┌──────────────────────────────────────┐
 │                 1524                   │
 │  Learn relationships between lesion    │
 │  characteristics and                   │
 │  options for successful treatments     │
 └──────────────────┬─────────────────────┘
                    │
                    ▼
       ┌───────────────────────────┐
       │           1526            │
       │  Generate conditions      │
       │  based on                 │
       │  learned relationships    │
       └───────────┬───────────────┘
                   │
                   ▼
       ┌───────────────────────────┐
       │           1528            │
       │  Distribute conditions to │
       │  medical devices          │
       └───────────┬───────────────┘
                   │
                   ▼
            ┌─────────────┐
            │     END     │
            └─────────────┘
```

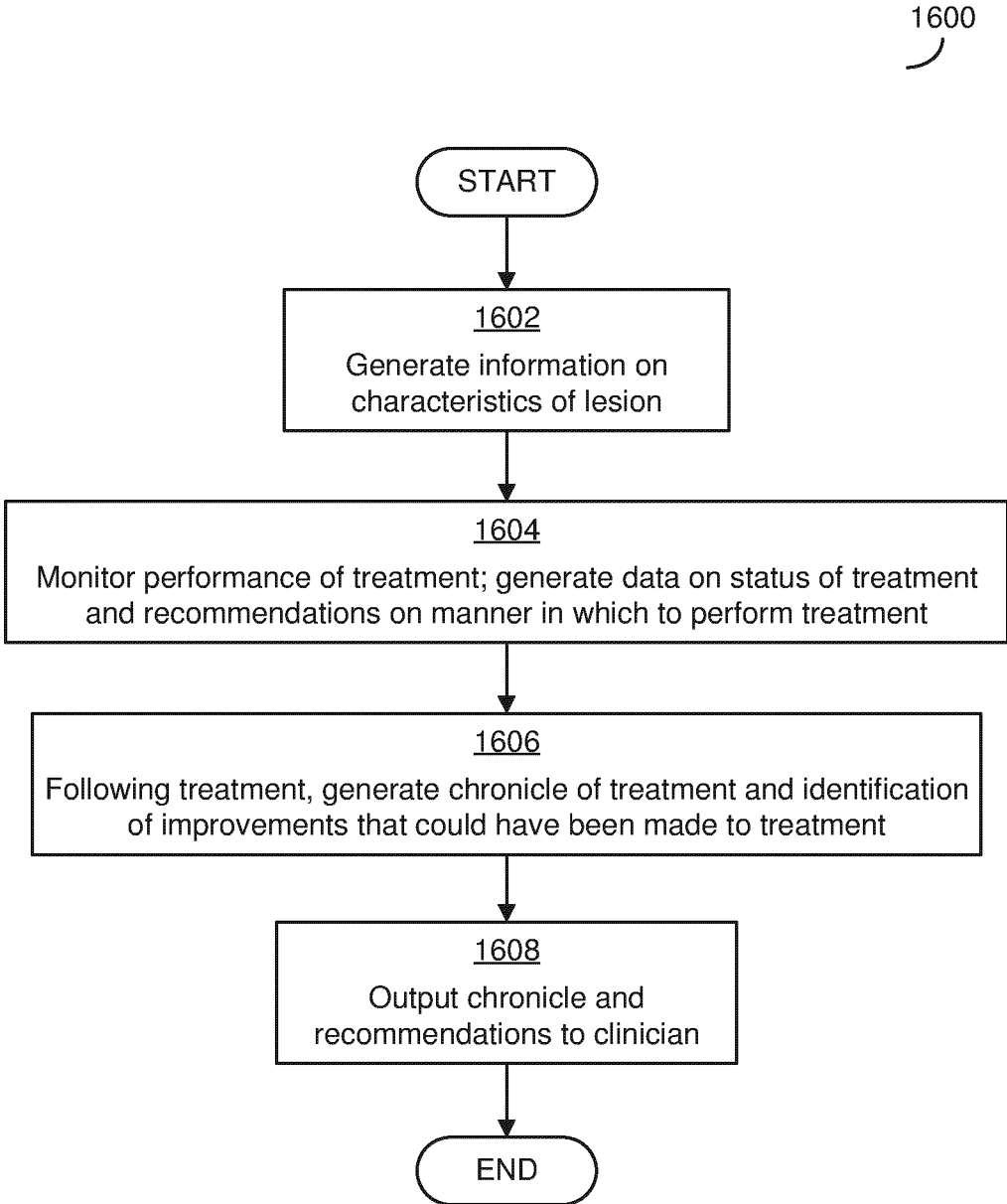

```
          ┌─────────────┐
          │    START    │
          └─────────────┘
                 │
                 ▼
      ┌────────────────────────┐
      │         1602           │
      │  Generate information  │
      │   on characteristics   │
      │       of lesion        │
      └────────────────────────┘
                 │
                 ▼
```

1604

Monitor performance of treatment; generate data on status of treatment and recommendations on manner in which to perform treatment

1606

Following treatment, generate chronicle of treatment and identification of improvements that could have been made to treatment

1608

Output chronicle and recommendations to clinician

END

START

2302
Detect characteristics of a cancerous cell

2304
Based on the detected characteristics, select treatment option to recommend 2306
Monitor performance of treatment option 2308
Output information on status of treatment

END

2400

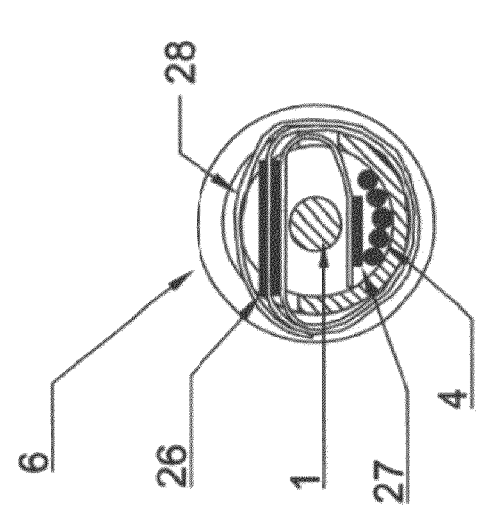
FIG. 36B
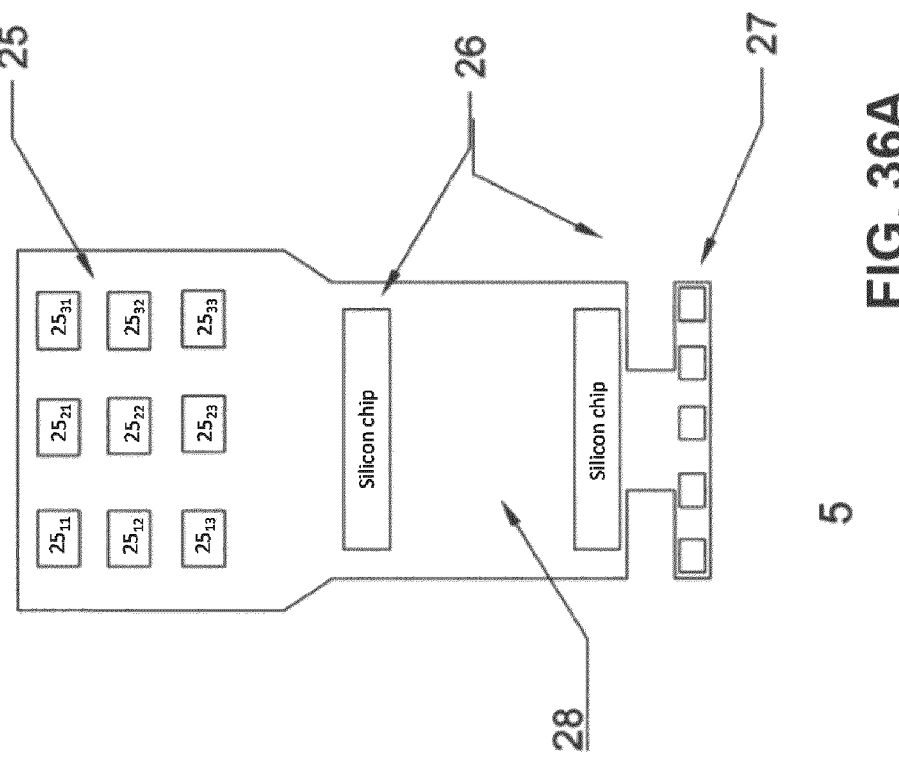
FIG. 36A

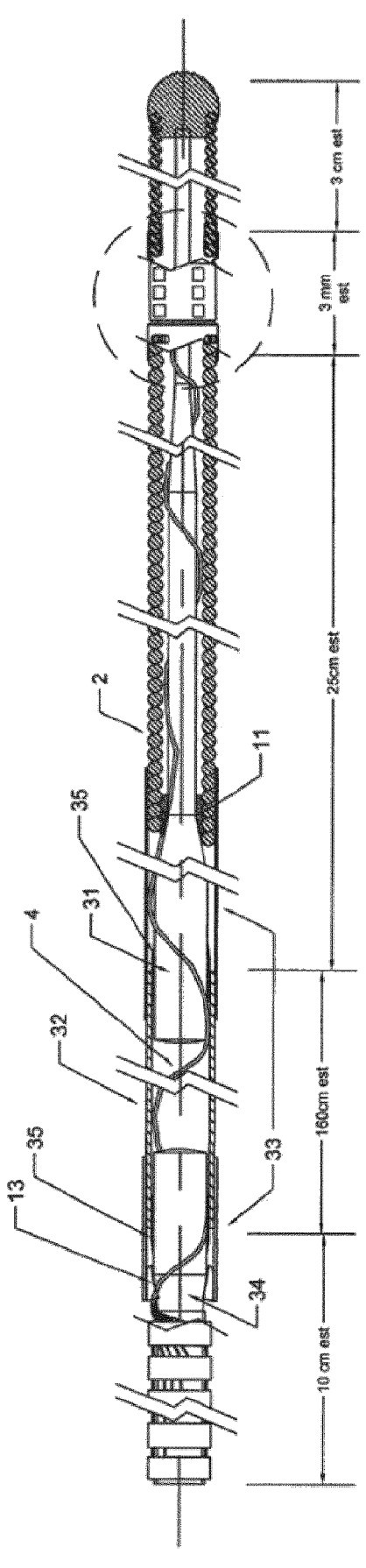
FIG. 37

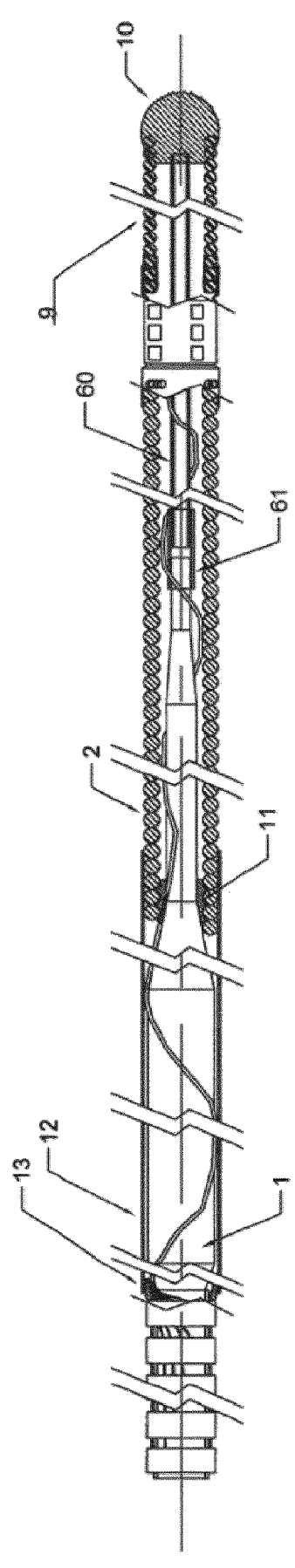
FIG. 40

4100

4100

4200
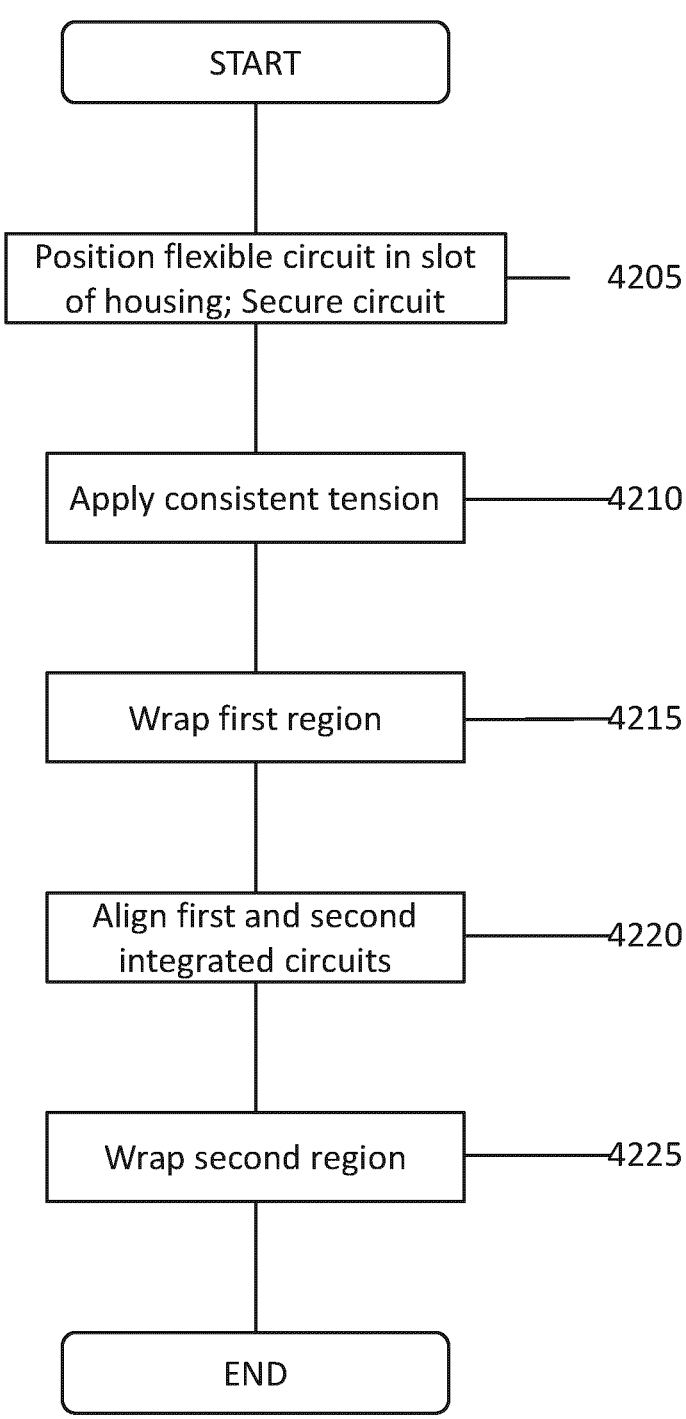
START
Position flexible circuit in slot of housing; Secure circuit — 4205
Apply consistent tension — 4210
Wrap first region — 4215
Align first and second integrated circuits — 4220
Wrap second region — 4225
END
*FIG. 42*

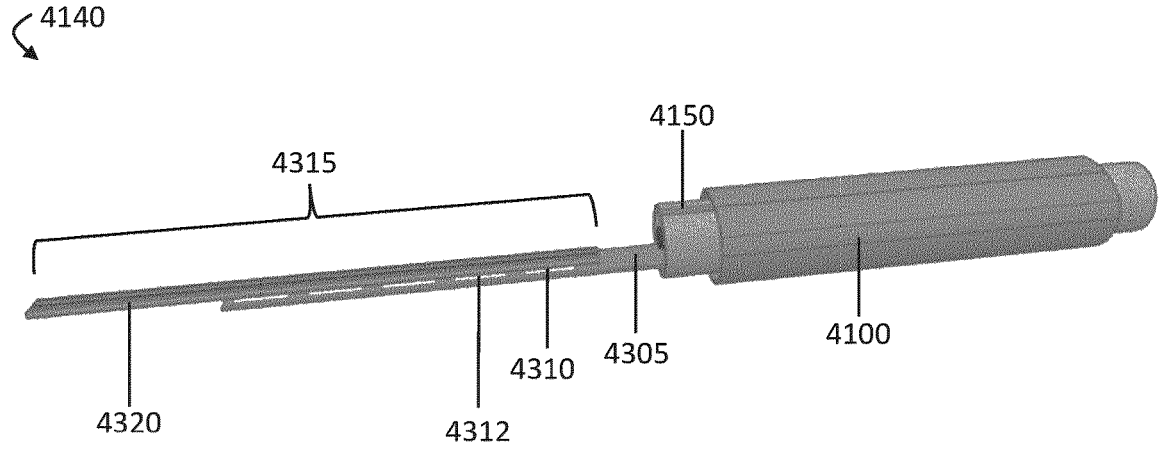
FIG. 43A
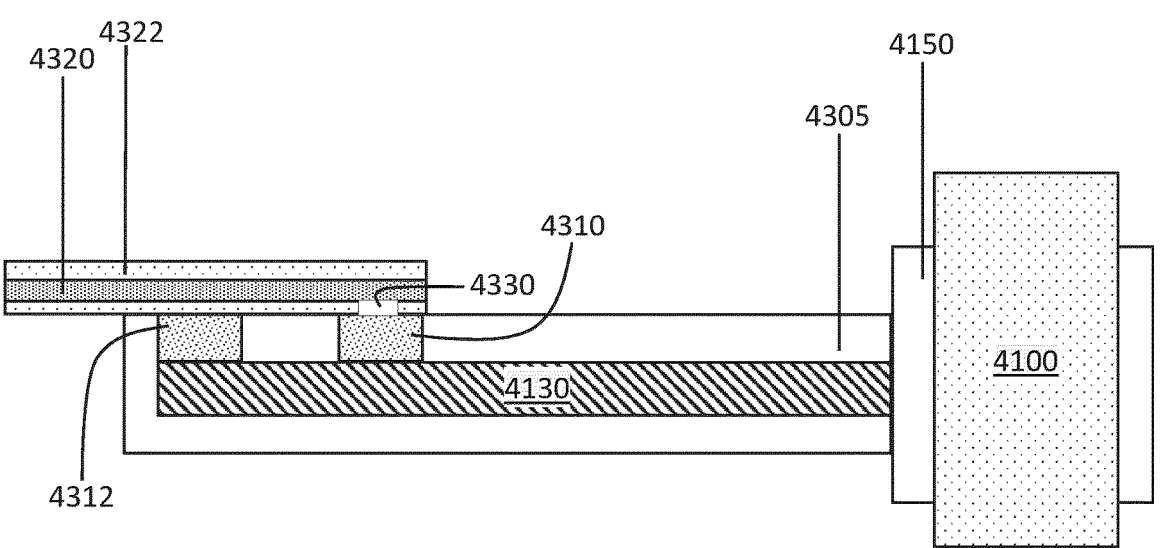
FIG. 43B

INSERTABLE DEVICE INCLUDING FLEXIBLE CIRCUITRY

CROSS-REFERENCE TO RELATED APPLICATIONS

This application is the U.S. National Stage application, pursuant to 35 U.S.C. § 371, of PCT International Patent Application No. PCT/EP2022/051281, filed Jan. 20, 2022, designating the United States and published in English, which claims priority under 35 U.S.C. §§ 119 and 365 to European Patent Application No. 21305969.4, filed Jul. 12, 2021, and U.S. Patent Application 63/139,461, filed on Jan. 20, 2021. The contents of each of the aforementioned applications are incorporated herein by reference in their entirety.

BACKGROUND

Blockages of blood vessels (including veins or arteries) may occur in various parts of an animal (e.g., a human or a non-human animal) and may have significant repercussions. In an ischemic stroke, for example, a blood clot fully or partially blocks blood flow in a cerebral artery. If the clot is not treated quickly, insufficient blood flow may cause irreparable damage to the brain.

Blockages may be caused by blood clots, which may be caused by coagulation of red and/or white blood cells and/or platelets within a blood vessel. The coagulation may be triggered by a variety of factors, including an injury, abnormal blood flow at the site of the blockage, a disease/condition predisposing an animal to coagulation, and/or other factors.

A common treatment of a clot is chemical dissolution of the clot, which is feasible within the first 4.5 hours following blockage of a blood vessel. Another common option is mechanical thrombectomy, in which an aspiration catheter or a stent-retriever is used to remove the blood clot from the blood vessel.

Stent-retrievers include a stent attached at the end of a wire. The stent is deployed into the vasculature and into the clot, expanded into the clot, and, after a typical waiting time of 0.5 to 10 minutes, extracted to pull the clot out of the blood vessel. Due to non-optimal grabbing of the clot by the stent-retriever, some parts of the clot may be left by or be lost from the retriever, such that several succession treatments (an average 3 times) may be necessary to treat the blockage and restore circulation in the vessel. Each repetition increases injury to the vessel wall and increases both the intervention duration and the duration of impeded blood flow due to the blockage, potentially leading to irreparable damage of the animal. The physio-mechanical process of clot grabbing is currently poorly understood, but the two most common explanations for non-optimal grabbing of a clot are (1) the stent-retriever never deploys into the blood clot and only friction induced by the stent-retriever pushing the blood clot against the wall is responsible for the retrieval of the clot, and (2) the stent deploys into the blood clot but an insufficient amount of time was provided for the stent to coalesce with the blood clot.

If an aspiration catheter is used to remove the blood clot, a clinician inserts the catheter into the vasculature and operates the catheter to aspirate the clot into the catheter. Depending on the diameter of the catheter, it may be placed in direct contact with the clot or placed in a proximal region of the vessel. Depending on the composition and viscosity of the clot, the aspiration method may differ. Some difficulties may arise with aspiration catheters. For example once the clot is aspirated into the catheter, it can block the flow inside the catheter. In such situations, a clinician may not be aware without extraction of the catheter whether the clot is blocking a tip of the catheter or is inside the catheter and blocking a tube. If the clot is blocking the tip of the catheter, there is a risk the clot may be inadvertently released during removal of the catheter, such that the clot may become an embolism that travels through the blood stream and blocks a vessel in another part of the animal.

SUMMARY

The present invention relates to a circuit board for use with an invasive probe to be inserted into a duct of an animal, the circuit board comprising:

a first region, comprising:
  an interconnect layer,
  a first polymer layer disposed on a first side of the interconnect layer, and
  a second polymer layer disposed on a second side of the interconnect layer opposite the first side; and
a second region, comprising:
  one or more integrated circuits,
  the interconnect layer connected to the one or more integrated circuits,
  the first polymer layer disposed on the first side of the interconnect layer and the one or more integrated circuit, and
  the second polymer layer disposed on the second side of the interconnect layer and the one or more integrated circuit side opposite the first side;
wherein in the first region a first thickness of the first polymer layer matches a second thickness of the second polymer layer, and wherein a first flexibility of the first region is greater than a second flexibility of the second region.

According to another advantageous aspects of the invention, the circuit board includes:

a first integrated circuit arranged to operate one or more sensors to sense one or more values, and
a second integrated circuit electrically connected to the first integrated circuit and comprising one or more circuits to be operated by the first integrated circuit.

The invention also relates to a circuit board for use with an invasive probe to be inserted into a duct of an animal, the circuit board comprising:

a first region, comprising:
  an interconnect layer,
  a first polymer layer disposed on a first side of the interconnect layer, and
  a second polymer layer disposed on a second side of the interconnect layer opposite the first side; and
a second region, comprising:
  a first integrated circuit arranged to operate one or more sensors to sense one or more values,
  a second integrated circuit electrically connected to the first integrated circuit and comprising one or more circuits to be operated by the first integrated circuit,
  the interconnect layer electrically connecting the first and second integrated circuits,
  the first polymer layer disposed on the first side of the interconnect layer and the first and second integrated circuits, and
  the second polymer layer disposed on the second side of the interconnect layer and the first and second integrated circuits opposite side the first side.

According to other advantageous aspects of the invention, the circuit board includes one or more of the following features, taken alone or in combination:

in the first region a first thickness of the first polymer layer matches a second thickness of the second polymer layer;

a first flexibility of the first region is greater than a second flexibility of the second region.

The invention also relates to an invasive probe, preferably a guidewire, comprising:

a housing;

one or more electrical components; and a circuit board as described above, the circuit board being at least partially disposed within the housing, wherein the one or more electrical components are mounted on the circuit board, and wherein the circuit board comprises:

a region of the circuit board that extends from the housing comprising two or more conductive contacts disposed outside of the inflexible housing, the two or more conductive contacts comprising a first contact and a second contact, at least one interconnect layer to electrically connect the two or more conductive contacts to the one or more electrical components, wherein a first wire is electrically connected to the first contact disposed outside of the inflexible housing, and wherein a second wire is electrically connected to the second contact disposed outside of the inflexible housing.

According to other advantageous aspects of the invention, the invasive probe includes one or more of the following features, taken alone or in any technically possible combination:

the invasive probe further comprises at least one additional wire, the two or more conductive contacts are three or more conductive contacts and comprise one or more additional conductive contacts disposed outside of the inflexible housing, the first wire, the second wire, and the at least one additional wire are joined in a ribbon, wherein the first wire, the second wire, and each of the at least one additional wires are electrically isolated from other wires of the ribbon and each wire of the ribbon is electrically connected to one conductive contact of the three or more conductive contacts;

each wire of the ribbon comprises an insulating jacket that electrically isolates the wire in the ribbon, and for each wire of the ribbon that is electrically connected to one conductive contact of the three or more conductive contacts of circuit board, the insulating jacket of the wire contacts the other conductive contacts of the three or more conductive contacts of the circuit board;

the three or more conductive contacts of the circuit board are distributed outside the inflexible housing across the region of the circuit board that extends from the inflexible housing, each wire of the ribbon includes an aperture in the associated insulating jacket of the wire at a position corresponding to a position of a conductive contact of the three or more conductive contacts to which the wire is electrically connected, and the invasive probe further comprises three or more regions of a conducting material joining the ribbon to the circuit board, the three or more regions of the conductive material respectively positioned on the circuit board at positions corresponding to positions of each of the three or more conductive contacts;

the circuit board is flexible, the ribbon is flexible, and the three or more regions of the conducting material form three or more regions of inflexibility where each is positioned on the circuit board;

the invasive probe further comprises an insulating glue disposed proximate an area where the first wire, the second wire, and/or additional wires are electrically connected to the first contact, the second contact, and/or additional conductive contacts;

the invasive probe is a guidewire comprising a core wire made in an electrically conductive material, each of the first wire, the second wire, and/or additional wires being arranged on an external surface of the core wire, the core wire being connected to a potential reference, preferably through a capacitor;

the first wire, the second wire, and/or additional wires include at least one of a ground wire and a positive potential wire for feeding electric power to the circuit board, and a signal-carrying wire for providing, to the circuit board, a time-dependent signal, the signal-carrying wire being arranged between the ground wire and the positive potential wire;

at least one integrated circuit is configured to implement a digital communication protocol by feeding a digital time-dependent signal through at least one of the first wire, the second wire, and/or additional wires;

the first region radially surrounds at least a portion of the second region with respect to a longitudinal direction of the housing;

the invasive probe further comprises an elongated core;

at least a portion of the second region is positioned adjacent to the elongated core;

the invasive probe further comprises a jacket;

the first region is a flexible region;

the second region is an inflexible region;

the first region is configured to have a bending radius ranging from 1 micron and 50 microns;

the first region is configured to surround at least a portion of the second region;

a thickness of the first polymer layer and a thickness of the second polymer layer are matched within the first region;

one or more of the integrated circuits of the second region is positioned nearer to a top surface of the first polymer layer relative to a bottom surface of the second polymer layer;

the one or more sensors comprises an electrode array;

the first integrated circuit is configured to control or receive data from the one or more sensors;

the second integrated circuit comprises a filtering capacitor.

The invention also relates to a method of fabricating an invasive probe as described above, wherein the housing includes a slot, the method comprising:

positioning a flexible circuit board as described above, with respect to the housing, wherein the positioning comprises positioning the second region of the flexible circuit board within the slot of the housing, and wrapping the first region of the flexible circuit board around the housing with the second region positioned within the slot.

According to other advantageous aspects of the invention, the method includes one or more of the following features, taken alone or in any technically possible combination:

wrapping the first region around the housing comprises applying a consistent pressure to the first region before and/or during the wrapping;

the method further comprises joining each of the plurality of wires of the invasive probe to a respective conductive contact of the plurality of conductive contacts of the invasive probe, wherein the plurality of conductive contacts are formed on the flexible circuit board of the invasive probe, the flexible circuit board being partially disposed within the inflexible housing and the plurality of conductive contacts being disposed outside of the inflexible housing;

the method further comprises joining at least a portion of the flexible circuit board with the housing using a non-conductive material.

Embodiments described relate to a medical device including an invasive probe that, when inserted into a duct (e.g. vasculature) of an animal (e.g., a human or non-human animal, including a human or non-human mammal), may aid in diagnosing and/or treating a lesion of the duct (e.g. a growth or deposit within vasculature that fully or partially blocks the vasculature). The invasive probe may have one or more sensors to sense characteristics of the lesion, including by detecting one or more characteristics of tissues and/or biological materials of the lesion. The medical device may be configured to analyze the characteristics of a lesion and, based on the analysis, provide treatment recommendations to a clinician. Such treatment recommendations may include a manner in which to treat a lesion, such as which treatment to use to treat a lesion and/or a manner in which to use a treatment device.

Certain embodiments relate to a guidewire comprising a solid elongated core having a proximal region and a distal region, a jacket enclosing at least a portion of the proximal region of the elongated core, one or more conductive wires leads extending along the elongated core and positioned to be disposed at least partially between the elongated core and the jacket, a flexible structure positioned around at least a portion of the distal region of the elongated core, and electronic circuitry electrically connected to the one or more conductive wire leads and coupled to the distal region of the elongated core.

Certain embodiments relate to a guidewire comprising a solid elongated core, a multi-filar coil positioned around a portion of the solid elongated core, a housing coupled to the solid elongated core and disposed between the multi-filar coil and a distal end of the elongated core, and a circuit disposed on a flexible substrate that is wrapped within and/or around at least a part of the housing, the flexible circuit comprising one or more impedance sensors.

Certain embodiments relate to an apparatus for detecting impedance of a tissue in a vascular system, the apparatus comprising a housing having a recess formed thereon, and a flexible substrate comprising thereon a plurality of electrodes and at least one first integrated circuit electrically coupled to the plurality of electrodes, the at least one first integrated circuit having a first circuit to generate probe signals and to drive the plurality of electrodes with the probe signals and a second circuit to process detection signals received by the plurality of electrodes in response to transmitting the probe signals outside the flexible substrate; wherein the flexible substrate is wrapped around a perimeter of the housing and has a portion that passes through the recess of the housing, the plurality of electrodes being disposed outside the housing and oriented outwardly relative to the housing.

Certain embodiments relate to a method for assembling a guidewire for use in vascular operations, the method comprising forming a jacket having a recess formed therethrough, passing a solid elongated core through the recess of the jacket, passing one or more conductive wire leads through the recess of the jacket and positioning the one or more conductive wire leads between the jacket and the elongated core, passing a portion of a multi-filar coil through the recess of the jacket, and necking the jacket to reduce the size of the lumen.

Certain embodiments relate to a method for assembling a device to be inserted within an anatomical duct of an animal. The method comprises forming a tubular jacket defining a lumen, passing an elongated core through the lumen of the tubular jacket, passing a portion of a flexible structure through the lumen of the tubular jacket, and necking the tubular jacket to reduce the size of the lumen.

In one aspect, a medical device for diagnosis and/or treatment of a lesion of a duct of an animal is described. In some embodiments, the medical device comprises an invasive probe for insertion into the duct of the animal and removal from the duct following the diagnosis and/or treatment, the invasive probe comprising at least one sensor to measure one or more characteristics of the lesion; at least one processor; and at least one storage medium having encoded thereon executable instructions that, when executed by at least one processor, cause the at least one processor to carry out a method comprising determining, based at least in part on an analysis of the one or more characteristics, one or more treatment recommendations for a manner in which to treat the lesion and outputting the one or more treatment recommendations to the user via a user interface.

In certain embodiments, the medical device comprises an invasive probe arranged to be inserted into a duct of an animal during diagnosis and/or treatment of a lesion of the duct and removed from the duct following the diagnosis and/or treatment, the invasive probe being configured to make one or more measurements of the lesion of the duct, the invasive probe comprising at least one impedance sensor and at least one circuit to drive the at least one impedance sensor to make a plurality of measurements of impedance of the lesion, wherein each measurement of the plurality of measurements of impedance corresponds to a frequency of a plurality of frequencies and is a measurement of impedance of the lesion when an electrical signal of the corresponding frequency is applied to the lesion.

Certain aspects are related to inventive methods of operating a medical device for diagnosis and/or treatment of a lesion of a duct of an animal, the medical device comprising an invasive probe to be inserted into the duct of the animal and removed from the duct following the diagnosis and/or treatment of the lesion. In some embodiments, the method comprises generating, with the invasive probe of the medical device while the invasive probe is disposed within the duct of the animal, data indicating one or more characteristics of the lesion of the duct of the animal, wherein generating the data comprises operating at least one sensor of the invasive probe to measure the one or more characteristics of the lesion; determining, using at least one processor of the medical device and based at least in part on an analysis of the one or more characteristics, one or more treatment recommendations for a manner in which to treat the lesion; and outputting the one or more treatment recommendations for presentation to a user via a user interface.

According to certain embodiments, a method of operating a medical device for diagnosis and/or treatment of a lesion of vasculature of an animal, the medical device comprising an invasive probe to be inserted into the vasculature of the animal and removed from the vasculature following the diagnosis and/or treatment of the lesion comprises generating, with the invasive probe of the medical device while the invasive probe is disposed within the vasculature of the animal, data indicating one or more electrical properties of the lesion of the vasculature of the animal, wherein generating the data comprises operating at least one sensor of the invasive probe to measure the one or more electrical properties of the lesion; and outputting information indicative of the one or more electrical properties, for presentation to a user via a user interface.

In some embodiments, an apparatus is described. In accordance with certain embodiments, the apparatus comprises at least one processor and at least one storage medium having encoded thereon executable instructions that, when executed by the at least one processor, cause the at least one processor to carry out a method comprising receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

At least one storage medium having encoded thereon executable instructions that, when executed by at least one processor, cause the at least one processor to carry out a method is described in accordance with certain embodiments. In some embodiments, the method comprises receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

Certain embodiments describe a method comprising operating at least one processor to carry out acts of: receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on application of a machine learning process to the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

According to some embodiments, a method of diagnosing and/or treating a lesion of a duct of an animal is described. In certain embodiments, the method comprises inserting into the duct of the animal an invasive probe of a medical device, the invasive probe comprising at least one sensor to measure one or more characteristics of a tissue and/or biological material of the lesion; operating the medical device to generate one or more recommendations on treatment of the lesion based at least in part on the one or more characteristics measured by the at least one sensor of the invasive probe; treating the lesion in accordance with the one or more recommendations of the medical device on treatment of the lesion; and removing the invasive probe from the duct of the animal.

According to some embodiments, a medical device configured to diagnose and/or treat a lesion of a duct of an animal is described. In certain embodiments, the medical device comprises inserting an invasive probe of the medical device into the duct of the animal, the invasive probe comprising at least one sensor to configured to measure one or more characteristics of a tissue and/or biological material of the lesion; further configured to generate one or more recommendations on treatment of the lesion based at least in part on a measurement of the one or more characteristics by the at least one sensor of the invasive probe; and further configured to deliver a treatment to the lesion in accordance with the one or more recommendations on treatment of the lesion. In certain embodiments, the medical device is also configured to remove the lesion from the duct of the animal.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. The foregoing is thus a non-limiting summary of the invention, which is defined by the attached claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 15A-15B are flowcharts of illustrative processes for operating a server to analyze reports on treatments to determine conditions with which to configure medical devices, which may be implemented in some embodiments;

FIG. 16 is an example of a process that may be implemented in some embodiments for generating a chronicle of a treatment;

FIG. 36A illustrates an example of a flexible circuit which may be used in some embodiments with the guidewire of FIG. 31;

FIG. 36B illustrates an example of an assembly using the housing of FIG. 35 and the flexible circuit of FIG. 36A, in accordance with some embodiments;

FIG. 37 is a schematic diagram illustrating another example of a guidewire which may be implemented in some embodiments;

FIG. 40 is a schematic diagram illustrating yet another example of a guidewire which may be implemented in some embodiments;

FIG. 42 is a flowchart of a method for positioning and wrapping a flexible circuit board within an inflexible housing of a guidewire, according to some embodiments;

FIGS. 43A-43B schematically illustrate a region of a circuit board disposed outside of an inflexible housing with conductive contacts of the circuit board attached to wires disposed outside of the inflexible housing, according to some embodiments.

DETAILED DESCRIPTION

Figure 1:
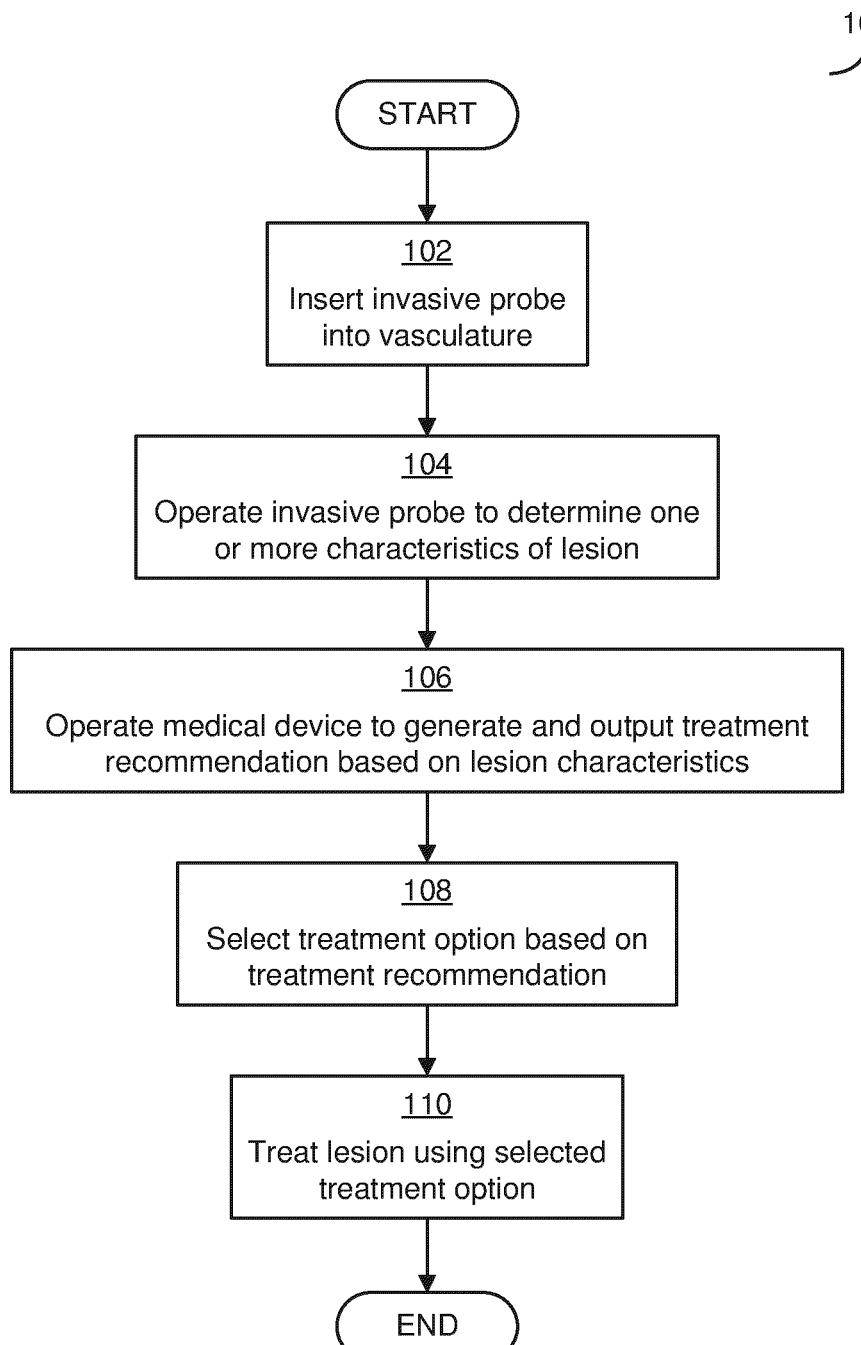
FIG. 1 is a flowchart of a manner in which a clinician may operate a medical device to diagnose and/or treat a lesion, in accordance with embodiments described herein.

Embodiments described herein relate to a medical device including an invasive probe that, when inserted into a duct of an animal (e.g., a human or non-human animal, including a human or non-human mammal), may aid in diagnosing and/or treating a lesion of the duct, which may be a blockage (e.g., a clot) that fully or partially blocks the duct. The duct may be, for example, a blood vessel of the animal or other duct and the lesion may be formed, in whole or in part, by a growth in the duct, an accumulation of material in the duct, and/or any other cause of a lesion. The invasive probe may have one or more sensors to sense characteristics of the lesion, including by detecting one or more characteristics of tissues and/or biological materials of the lesion. The medical device may be configured to analyze the characteristics of a lesion and, based on the analysis, provide treatment recommendations to a clinician. Such treatment recommendations may include a manner in which to treat the lesion, such as which treatment to use to treat the lesion (e.g., if the lesion is to be removed, whether to use an aspiration catheter or a stent-retriever) and/or a manner in which to use a treatment device (e.g., how fast to extract a stent-retriever).

The duct within the animal may be narrow in diameter. As a result of the narrow diameter of the duct, the invasive probe that is to be inserted within the duct is also limited in diameter, which limits the size of the probe and thus the space available for components of the invasive probe. Further, in navigating the animal to reach the duct and/or in navigating the duct, the invasive probe may need to move within winding and meandering pathways of anatomy of the animal that may themselves be narrow. To navigate these pathways, the invasive probe may need to be flexible. However, electrical components may be susceptible to breakage if flexed. Therefore, to ensure reliability of the components of the invasive probe, at least some components of the invasive probe may be arranged in a manner to prevent them from being subjected to flexing forces, such as being housed on and/or within an inflexible housing. Such an inflexible housing may increase reliability of the components, but being inflexible, stands in tension with the goal of ensuring flexibility of the invasive probe to navigate the anatomy of the animal. To satisfy both goals, the inflexible housing may need to be smaller still, to limit the portion of the invasive probe that is inflexible and ensure the invasive probe is able to navigate the anatomy of the animal and navigate the duct.

This limited space of the inflexible housing means there is limited space in which components of an invasive probe, such as electrical components, can be disposed, which can limit the number of components to be included in the invasive probe. Limiting the number of components can, in turn, limit the functionality of the invasive probe. The inventor has recognized and appreciated, however, that there may be advantageous ways in which to arrange components within an inflexible housing that may allow for increasing a number of components to enable increased functionality while maintaining a small size of an inflexible housing.

Some embodiments include a flexible circuit, which may be fabricated to contain sensors and electronic circuitry (e.g., integrated circuits, conductive pads, interconnect layers, wires) for probing a lesion or blockage of the duct. The flexible circuit may be a flexible circuit board on which one or more integrated circuits are disposed. The circuit board may be flexible to enable it to be, in some embodiments, wrapped within and/or around at least a portion of the invasive probe. Wrapping the flexible circuit board may allow for increasing a surface area of the circuit board while reducing the volume occupied by the flexible circuit, the diameter needed for the circuit board, or other dimensions of the interior of the invasive probe within which the flexible circuit board is arranged. Increasing the surface area can provide for more surface area on which to arrange electrical components such as integrated circuits, providing a tech-nique for arranging multiple (e.g., two, or more) integrated circuits on or within an inflexible housing of an invasive probe (e.g., a guidewire).

Those skilled in the art will appreciated that a flexible circuit board that is wrapped will impose flexing forces on components within and/or mounted to the flexible circuit board. Such flexing forces could degrade and/or break the components of the circuit board and impact reliability of the invasive probe. The inventor has recognized and appreciated that particular designs of the flexible circuit may mitigate these risks and enable flexibility and wrapping while also enabling reliability of the components.

In some embodiments, the flexible circuit comprises a first region (e.g., a flexible region) and a second region (e.g., a rigid region or inflexible region), where the first region is more flexible than the second region. This may advantageously provide the flexible circuit with some one or more portions that are relatively flexible where the circuit can wrap within and/or around a portion of the invasive probe or a portion of the flexible circuit board itself, while one or more other portions are relatively inflexible and are not wrapped or flexed—or are flexed less than the first portions—when the overall flexible circuit is wrapped.

The first region(s) of the flexible circuit may include some electrical components (e.g., passive components) such as passive interconnection material (e.g., conductive traces or other circuit board interconnect structures) that conveys electrical signals within the flexible circuit and between components of the invasive probe, and the first region(s) may be arranged to flex in a manner that mitigates flexing forces applied to these electrical components and/or enables flexing forces to be applied to the electrical components in a manner that mitigates risk of degrading or breaking the components. For example, the first region may include a first layer of flexible material, such as polyimide or another material, that is arranged on a top side of the first region, and a second layer of the flexible material that is arranged on a bottom side of the first region, with one or more layers of interconnect material (e.g., a conductive material) disposed between the two layers of flexible material. The two layers of flexible material may be arranged in the first regions with matching flexibility, such as by having matching (e.g., identical) thicknesses. Having matching flexibility on the top and bottom flexible layers may enable application of flexing forces to the interconnect material that mitigates risk of degradation or breakage of the interconnection material due to breakage.

The second region(s) of the flexible circuit, which are less flexible than the first regions, may contain chips or integrated circuits of the invasive probe, such as one or more integrated circuits for operating one or more sensors of the invasive probe to, for example, sense electrical characteristics of tissue(s) of the duct contacted by the invasive probe. In some embodiments, the second region(s) that are less flexible than the first region(s) may be inflexible. Having the second regions be inflexible or of less flexibility may allow for protecting the integrated circuit(s) of the second region from experiencing flexing forces that could degrade or break the integrated circuits. In some embodiments, the flexible circuit may be arranged in the invasive probe with respect to an inflexible housing of the invasive probe, with the integrated circuits of the second region(s) disposed in the inflexible housing in a location that the inflexible housing may provide some protection from or prevent application of flexing forces to the second region(s).

For some embodiments, the first region of the flexible circuit comprises an organic or polymeric material that provides or maintains flexibility for the flexible circuit board, while the second region of the flexible circuit may further comprise one or more inorganic components (e.g., a chip containing silicon and/or one or more other inorganic semiconductor materials) that are less flexible than the organic components.

In certain embodiments, the flexible circuit board comprises two or more integrated circuits (e.g., a first integrated circuit, a second integrated circuit) that are configured to sense a parameter or value (e.g., impedance) of a lesion of a duct. Of those two integrated circuits, functionality may be divided between them in a manner that may drive an increase in reliability of the sensing of the data. For example, a first integrated circuit may include active circuitry and be operatively coupled with and drive one or more sensors for measuring the impedance of a lesion and may be directly connected with the sensors (which may be implemented as one or more pairs of electrodes) in the flexible circuit. The first integrated circuit may be disposed on the flexible circuit board closer to the sensor(s) than the second integrated circuit. In some such embodiments, the second integrated circuit may include passive circuitry that is driven by the active circuitry of the first integrated circuit and may be configured to process information received from the first integrated circuit, such as to filter electrical signals prior to or as a part of transmission along a communication wire of the invasive probe, as one example. In some embodiments, the two or more integrated circuits may be contained within an inflexible region of the flexible circuit. In some such cases, the inflexible region may be two inflexible regions that are connected in the flexible circuit by a flexible region.

Certain embodiments herein also include techniques for connecting a circuit board (e.g., a flexible circuit board) of an invasive probe to other portions of the invasive probe, such as to one or more wires that provide power and/or communication to electronics of the invasive probe. Those skilled in the art will appreciate that a connection point between a wire and a circuit board is a potential area of weakness that can degrade or break if force is applied to it, including flexing force. Due to the flexing force that is anticipated to be applied to an invasive probe as it navigates anatomy of an animal, one skilled in the art would appreciate the desirability of including the connection points for wires of the invasive probe within an inflexible housing where the connection points may be protected from flexing forces. However, as described above, the dimensions of a duct and thus the invasive probe may be relatively small and there may be limited space in the inflexible housing. Including the connection points within the inflexible housing may limit the space available for components, which could include limiting the space available for wires and limit the number of wires. Limiting the number of wires may undesirably limit the functionality of the invasive probe. There is thus a tension between reliability and functionality that arises from including the connection points within the inflexible housing so as to derive the reliability benefits of the inflexible housing.

The inventor has recognized and appreciated the advantages of certain arrangements for connection points of wires of an invasive probe that allow for increased reliability even with the connection points disposed outside of an inflexible housing of an invasive probe. In some embodiments described herein, at least a portion or a region of a flexible circuit board may extend outside of an inflexible housing. This region of the flexible circuit board may be flexible and may contain two or more conductive contacts, including a first contact and a second contact. Two or more wires (e.g., a first wire, a second wire) disposed outside the housing may each be electrically connected to one of each of the two or more conductive contacts in the area outside of the inflexible housing. The electrical connections may be made in a manner that can advantageously provide electrical communication between the circuit and other portions of the guidewire, without shorting the two or more wires and while providing more space for components within the housing. For example, the wires of the invasive probe may be arranged as a ribbon wire in which insulating jackets of the wires are physically joined together. In this example, each insulating jacket for each wire of the ribbon may contact each conductive contact of the flexible circuit, but each wire is electrically connected to only one of the conductive contacts. A conductive material may be used in this example to bind the ribbon wire to each of the conductive contacts and form the electrical connection between each one wire and the respective conductive contact. Advantageously, the conductive material may also be inflexible once disposed on the flexible circuit, conductive contacts, and/or ribbon wire. The conductive material may then, in this example, form regions of inflexibility outside of the inflexible housing, with the regions of inflexibility separated by regions without the conductive material that are more flexible. Through this arrangement of regions of conductive material, areas of inflexibility interspersed with areas of flexibility may be provided, which may enable the invasive probe to be overall flexible enough to navigate anatomy of an animal while also providing inflexibility in targeted areas of the invasive probe to increase reliability of the electrical connections between the wires and the flexible circuit.

Various examples described herein will discuss a medical device in context of vasculature lesions and manners of treating vasculature lesions. It should be appreciated, however, that embodiments are not so limited. Techniques described herein for sensing characteristics of lesions and generating treatment recommendations may be used with any suitable anatomical duct of an animal. Such ducts may include vasculature ducts and gastrointestinal ducts, for example. Those skilled in the art will appreciate that ducts in anatomy differ from anatomical cavities. For example, a duct may be significantly smaller in one dimension (e.g., a width) than in another dimension (e.g., a length).

Thus, in some embodiments, the invasive probe may be a component of a medical device for diagnosis and/or treatment of a lesion of vasculature. For example, the medical device may be a thrombectomy device and the invasive probe may be a component of the thrombectomy device. Accordingly, the invasive probe may be a component of a guide wire, an aspiration catheter, a micro-catheter, a stent-retriever, and/or another thrombectomy device. In some embodiments, a medical device may include two or more of a guide wire, an aspiration catheter, and a stent-retriever and the invasive device may be a component of one or more of these, including all of these.

As mentioned above, some embodiments described herein relate to a medical device including an invasive probe that, when inserted into an animal (e.g., a human or non-human animal, including a human or non-human mammal), may aid in diagnosing and/or treating a biological structure of the animal. In some embodiments, the biological structure may be a lesion of the animal, and may in some cases be a lesion of a duct of the animal or a lesion that occurs elsewhere in the animal's anatomy (i.e., in a location other than a duct). The lesion may be an abnormality in the anatomy of the animal, such as a deviation from a normal structure and/or function of a part of an animal, such as an abnormality associated with injury, a medical condition, or a disease. The lesion may appear in different parts of the animal, for example it may be included within a duct of the animal. A lesion of a duct may, for example, act as a blockage that fully or partially blocks the duct. The duct may be, for example, a blood vessel of the animal or other duct and the lesion may be formed, in whole or in part, by a growth in the duct, an accumulation of material in the duct, and/or any other cause of a lesion. The invasive probe of some embodiments may have one or more sensors to sense characteristics of a biological structure (e.g., a lesion), including by which may include determining a composition of the biological structure.

In some embodiments, detecting a composition of a biological structure may include identifying one or more biological materials of the structure, including one or more cells and/or one or more tissues present in the structure, and/or one or more plaque materials present in the structure. The biological materials of the structure that are identified may be all biological materials present in the biological structure, or only some of the biological materials present in the structure. Where only some of the biological materials are identified, the identified material(s) may be only those materials of a certain type of material, such as tissues/cells of the biological structure (as compared to other materials, such as plaque materials) or a particular type of tissues/cells (e.g., red blood cells present in the lesion, and not other types of cells). In cases in which a composition is determined and in which only one or some type(s) of biological materials are identified, determining the composition may include determining the amount(s) of the identified material(s) in the biological structure, such as determining the amount(s) of the identified material(s) relative to the total materials of the lesion, including by calculating a ratio of one or more of the identified material(s) to the total materials of the biological structure.

The inventor has recognized that tools that reduce the time it takes to diagnose and/or successfully treat lesions (such as blood clots) formed in neurological vasculature, including brain vasculature, could be desirable and advantageous. Clots can develop at the location of a blocked vessel (e.g., as a thrombus), or they can originate in other areas of the vascular system such as within limbs, then break away and travel (e.g., as an embolism) to the brain and become lodged in a vessel of the brain. If the occlusion caused by the clot limits or blocks the flow of blood and oxygen, the patient may suffer a stroke. Patients suffering from strokes are often treated by catheterization. Treatment typically involves placing a catheter percutaneously into the carotid arteries, by advancing the catheter along a very flexible small guidewire. The clinician then attempts to remove the clot by various means. Often the first attempt to remove the clot will be by applying suction with an aspiration catheter. If this is not successful, another option is a mechanical removal tool, such as a stent-retriever. Often, suction may fail because of the nature of the clot, as clots of different types are more or less susceptible to removal using suction. Every minute that an artery in the brain is clogged, more damage to the brain may be occurring. Therefore, time can be of the essence when treating these patients. The inventor has recognized that having to experiment with and sequentially use various tools, i.e., a guidewire, an aspiration catheter, and possibly a stent-retriever, until the clot is removed, can complicate efforts to minimize treatment time and can lead to adverse outcomes for patients.

The inventor has further recognized that insertion of tools, including catheters and guide wires, through brain vasculature is often problematic. Cerebral vessels are connected to the rest of the vascular system through the carotid arteries. These arteries have particularly tortuous shapes, which complicate the insertion of the tools. Specifically, carotid arteries include s-shaped bends in the region proximate to the sphenoidal segment (often referred to as M1) and the insular segment (often referred to as M2). To insert a tool into brain vasculature from an origin point elsewhere in the body (e.g., starting from the periphery, such as a limb), clinicians pass the tool through this s-shaped bend. However, this s-shaped bend complicates insertion and complicates the design of tools.

While a tool will typically bend and flex when navigated through vasculature, the tortuous shape of the s-shaped bend often causes tools, upon passage, to kink or yield so as to retain a bend even when an external mechanical force is no longer applied to the tool. A kink may be a bend or even fold in the tool that is retained by the tool even when an external mechanical force is not applied to the tool, due to a deformation in one or more materials of the tool. Kinks in a tool, even when minor, or even minor bends may cause numerous problems. First, once kinked or bent, it may be difficult to transmit torque along the length of the tool. Transmission of torque allows for a distal end of a tool, located within vasculature, to be manipulated from a proximal end of a tool, potentially located outside the animal and operated by a clinician. When a kink or bend prevents or limits transmission of torque, this can significantly limit the clinician's ability to appropriately steer the tool through the patient's vasculature on the other side of the s-shaped bend. Second, while a tool typically easily bends and flexes back and forth in response to torque applied by a clinician, once a kink or bend develops, the tool may no longer bend and flex in the same manner. As a result of the kink or bend, the tool may instead resist imposition of torque. When the tool resists in this way, potential energy may build until the applied force overcomes the resistance imposed by the kink/bend. At the point the resistance is overcome, the tool may suddenly and powerfully react, snapping into a new position. This phenomenon is referred to as "whipping." In an area past the s-shaped bend, where such whipping can occur as a result of a kink/bend that arises while passing the s-shaped bend, the vasculature is delicate and small in dimension, and whipping can significantly damage the vasculature. Any damage to brain vasculature may be critical, as loss of full and proper blood flow to the brain can cause permanent damage within only minutes.

Because of the risk of whipping, an important aspect of design of tools for insertion into brain vasculature is reducing the likelihood of kinks occurring.

The inventor has recognized that devices that are inserted into ducts of a body, including inserted into neurovasculature via the s-shaped bend, that include multiple sensors to measure one or more properties of a biological structure, could be advantageously designed and adapted to mitigate or eliminate some or all of the above-described problems of typical, conventional tools. For example, sensors that measure impedance of a biological structure at one or more points of the biological structure or one or more points of an environment of the biological structure could be configured to process measurements to yield information regarding the nature of biological structures they encounter, such as information that may identify and/or characterize the biological structure, or information on how to treat the biological structure.

However, adding sensors in this manner strictly conflicts with the goal of reducing susceptibility to kinking. Multiple sensors are not typically included in devices of the type described herein. Including multiple sensors in typical conventional devices according to conventional designs would lead to an increase in the size of the insertable device to an undesirable extent. In addition, conventionally, such an insertable device would include a hollow tube at the core of the insertable device, and wires for conveying control signals and/or data to a sensor (conventional devices have at most one sensor) would travel the length of the insertable device along the tube. Increasing the number of sensors, according to a conventional design, would result in a corresponding increase in the number of wires, and would also in such a conventional device increase the diameter of the tube. Such an increase in the diameter of the tube can have a corresponding increase in the susceptibility to kinking. Such devices, with a larger diameter and increased susceptibility to kinking, would not be suitable for use with neurovasculature.

Accordingly, the inventors developed and have described herein alternatives to conventional designs for insertable devices, including guide wires, for use with an insertable probe that includes multiple sensors for detecting one or more properties of a biological structure. Such a device may, in some embodiments, be suitable for use with neurovasculature.

Described herein are embodiments of an insertable device, which in some such embodiments includes multiple sensors to detect one or more properties of a biological structure. In some embodiments, devices include multiple sensors while also being of small dimension and having limited susceptibility to kinking, and have good ability to transmit torque for a clinician operating the device to navigate the device through vasculature or other ducts.

Insertable devices of some embodiments described herein have solid cores. The insertable device may include one or more sensors on a probe at an end of an elongate body, where the probe and at least a part of the elongate body may be inserted within a body of an animal. In some such solid-core devices, an innermost portion of the probe and/or the body may be solid, such as being made of a solid steel rod. This is in contrast to conventional insertable devices that typically have a hollow core along the elongate body. Compared to hollow core device, of which conventional catheters are an example, certain embodiments of invasive devices described herein are more likely to maintain their cross-sectional shapes even when tightly bent. As a result, the invasive devices of some embodiments described herein are advantageous for use in tortuous anatomy, such as in the cerebral vasculature.

As described above, treatment of a lesion (e.g., treatment of a thrombus) can often involve the use of different combinations of procedures together, or the selection of a particular treatment option (e.g., one tool) from among a set of treatment options (e.g., multiple available tools). What makes it difficult to determine a priori which treatment is most likely to succeed is the wide variability between the nature and composition of lesions, which is often unknown for a particular lesion. While certain treatments may be particularly suitable for treatment of a specific type of lesion (e.g., a thrombus with a particular nature or composition), those same treatments may not be sufficiently effective or the best choice for use with other types of lesions. The inventor has recognized that the design and use of insertable devices capable of determining the nature and/or composition of a lesion can be advantageous in eliminating or mitigating this selection uncertainty. In particular and as a result, the inventor has developed tools for sensing one or more properties or attributes of a lesion, which can enable identifying and/or characterizing the lesion, and/or determining an appropriate treatment for the lesion. Certain embodiments of the disclosed insertable devices, e.g., those having multiple sensors for sensing one or more values of a biological structure (e.g., lesion) at one or more positions of the biological structure, can provide such functionality. The information obtained through use of the sensors may be then be used to determine one or more characteristics of the clot, such as the composition of the clot, which in turn may aid a system and/or a clinician in selecting or recommending a treatment for the biological structure.

In some embodiments, the invasive probe may include one or a number of sensors, which may include sensors to measure an impedance of the biological structure. The sensors may measure impedance of the lesion when electrical signals having particular frequencies are applied to the lesion. The medical device may be configured to, based on the impedance values, determine a composition of the biological structure and/or one or more characteristics of the biological structure. For example, each sensor may, in some embodiments, be operated to detect an impedance spectrum of a biological material contacting the sensor, such that different sensors of the invasive probe may, at the same time, generate different impedance spectra for different biological materials of the biological structure. In some embodiments, the medical device may then generate treatment recommendations based in part on the determined composition. As discussed above, determining the composition may include identifying amounts of one or more biological materials within a biological structure, which may be less than all materials of the biological structure. For example, in some embodiments, an amount of a biological structure that is composed of red blood cells is determined.

In some embodiments, the multiple sensors of an insertable device may be arranged in a probe section of the device, which may be in a distal "working zone" at the end of an elongate body of the insertable device (e.g., the last 30 cm-50 cm of a device). While in conventional devices wire leads are typically electrically isolated and arranged in a hollow core, in embodiments in which multiple sensors are arranged in a device with a solid core, the inventor has recognized that a different approach to electrical isolation of the electrical wires and couplings would be advantageous. Such isolation of the electrical components may prevent or reduce the chances of contact with environmental factors (e.g., liquids) that could cause shorts. In some embodiments, wire leads are wrapped around or otherwise disposed along a solid core and a protective jacket is encloses the wire leads. In some embodiments, the jacket may be sufficiently thin so that the thickness of the invasive probe is substantially unchanged yet sufficiently robust to isolate the wire lead and their connections from the fluids. In some embodiments, the jacket is made of polyimide.

The inventor has also discovered that by, in certain embodiments, disposing both sensors and other electronic circuits of the device in a distal portion of the device that may be inserted into a body of an animal and may have to navigate complex anatomy of small dimensions can result in certain operational and performance advantages. The inventor has further discovered that placing circuitry that operates the sensors, including circuitry to process values detected by the sensors, proximate to the sensors in certain embodiments can limit noise and/or attenuation of the signal. Particularly in the case of a device having a long elongate body, the farther the processing components are from the biological structure being sensed, typically the more susceptible the signal will be to effects of noise and attenuation.

In some embodiments, due to limitations on dimensions of anatomy that an insertable device may navigate, the diameter of a distal end of the device, including the probe and at least part of the elongate body, may advantageously not exceed 0.014" (double quotes are used herein to indicate measurements in inches), that is 0.36 mm (millimeters).

As discussed briefly above and in more detail below, in some embodiments, to accommodate sensors and circuits in the probe area of an insertable device, the sensors and/or circuits may be disposed on flexible substrates, including flexible circuit boards. These substrates can serve as support for the sensors and the chips hosting the circuits. Being flexible, in some embodiments, the substrates may be curved in such a way to substantially limit the overall dimensions, including wrapped around on itself within (or at least partially within) an insertable device. For example, at least a portion of the flexible substrate may be wrapped around a solid core of an insertable device. Sensors, when arranged on the flexible substrate, may be arranged such that when the flexible substrate is wrapped around an exterior of the probe of the insertable device, the sensors are arranged on an outside of the probe.

In some embodiments, such a flexible substrate may be tightly wound, and it may be beneficial for the flexible substrates to be extremely thin and made of resistant flexible materials. In some embodiments, chips located on the circuit board (e.g., a chip hosting processing circuitry) may not be flexible enough to be curved. In some such embodiments, chips or other components may be placed inside the probe with electrical interconnection to the flexible sensing part and interconnection to the wire leads. To protect soldering points of small wires that are attached to the flexible circuits from any environmental factors (e.g., liquids) that may case short-circuiting of the electronics, it may be desirable in some embodiments to embed all the soldering points in a polymer as epoxy, or in cyano (e.g., cyanoacrylate).

In some embodiments, to accommodate electronics circuitry inside the probe, there may be little packaging of the active electronics. For example, chips used in some embodiments may be initially packaged using standard packaging techniques, but may then be "thinned" to eliminate some of the packaging before being installed in the insertable device. To avoid or reduce the chances of rupture of electrical interconnections inside the flexible substrate, it may be desirable in some cases to avoid extreme bending of the flexible electronics, or place some elements more sensitive to bending in a mechanical neutral plane of the substrate to limit the stress in those elements while bending the substrate.

Certain of the disclosed devices are configured with good torque-ability, to aid a clinician in manipulating and steering the insertable device within a body of an animal. In some cases, the insertable device may be sufficiently torque-able for the clinician to be able to apply torque to the device and bend it to navigate tight curves in anatomy encountered along a path to an area of interest within the body (e.g., location of a suspected lesion).

In some such embodiments, a torque-able device has a core having a tapered shape from a proximal end (closer to the clinician) to a distal end (closer to a tip positioned farthest within a body of an animal). Closer to the proximal end, the region handled by the clinician, the core may be thicker to provide higher torque transmission. Closer to the distal end, the region may require more flexibility to be guided through tortuous anatomy of some parts of the body.

In this area, the thickness of the core may be reduced, which can increase flexibility. This core may, in some embodiments, be constructed of a high-strength, flexible material. For example, the core may be or include high strength stainless steel, such as HiTen 304V stainless steel.

In one example, an insertable device has a length that is approximately 200 cm between the handle and the tip, and includes multiple segments, some of which are tapered. The longest of these segments may have a length between 130 cm and 170 cm, in some embodiments, and a diameter between 0.010" (0.25 mm) and 0.014" (0.36 mm). Distal to this segment and developing into a more flexible "working zone" of a tool is a tapering section, which may be a taper having a length between 5 cm and 10 cm and a diameter tapering down to approximately 0.005" (0.13 mm). Following the taper may be a tapered 10 cm-long segment, and subsequently another taper having a length between 5 cm and 10 cm and diameter tapering down to approximately 0.003" (0.08 mm). The distal portion may have a length between 5 cm and 10 cm and a diameter of approximately 0.003" (0.08 mm). The flexible substrate may be wrapped around this distal portion of the probe. It should be appreciated, however, that these dimensions and tapers are merely illustrative and that other embodiments are possible. It should also be appreciated that the term "diameter" is used herein not only to refer to structures having circular cross sections, but also to structures not having circular cross section. In these circumstances, the term diameter refers to the maximum width of the structure's non-circular cross section.

In some embodiments, to further promote torque transmission, some probes may be wrapped, at least partially, using a filar coil. The filar coil may include one filament or may include multiple filaments forming a multi-filar coil. In some such cases, a multi-filar coil may be formed, at least in some embodiments, by winding one or more wires/filaments around the solid core of the probe. The wire(s) of the coil may provide an effective means for the transmission of torque in some embodiments. That is, when torque is imparted on the probe's handle by the clinician impacting one end of the wire(s) of the coil, the torque imposed on the wire(s) is transferred from winding to winding along the length of the probe. In some embodiments, the filar coil may be located in an area of the guidewire where the inner solid core has a tapered shape and is more flexible than other areas of the solid core. Adding the coil in this area may maintain flexibility (such as by not greatly reducing flexibility) while adding torqucability.

Torque-ability of the filar coil may be adjusted as desired by adjusting the pressure with which the windings are assembled against one another. In some such cases, the closer the wires are positioned to one another, the larger the torque transmission will be.

It should be appreciate that while embodiments are described herein in connection with vasculature, including cerebral vasculature, and are described as being advantages with some features of human anatomy (e.g., the s-shaped bend at the top of the carotid arteries), embodiments are not limited to operating with human vasculature. Embodiments instead may operate with any type of anatomy and with any type of animal, including non-human mammals or non-mammals.

In some embodiments, the invasive probe may include sensors to measure an impedance of the lesion. The sensors may measure impedance of the lesion when electrical signals having particular frequencies are applied to the lesion. The medical device may be configured to, based on the impedance values, determine a composition of the lesion. The medical device may then generate the treatment recommendations based in part on the determined composition.

Various examples described herein will discuss the medical device in context of vasculature lesions and manners of treating vasculature lesions. It should be appreciated, however, that embodiments are not so limited. Techniques described herein for sensing characteristics of lesions and generating treatment recommendations may be used with any suitable anatomical duct of an animal. Such ducts may include vasculature ducts and gastrointestinal ducts, for example. Those skilled in the art will appreciate that ducts in anatomy differ from anatomical cavities. For example, a duct may be significantly smaller in one dimension (e.g., a width) than in another dimension (e.g., a length). A duct may have a shape that is variably tubular, whereas a cavity may not be tubular.

Thus, in some embodiments, the invasive probe may be a component of a medical device for diagnosis and/or treatment of a lesion of vasculature. For example, the medical device may be a thrombectomy device and the invasive probe may be a component of the thrombectomy device. Accordingly, the invasive probe may be a component of a guide wire, an aspiration catheter, a micro-catheter, a stent-retriever, and/or another thrombectomy device. In some embodiments, a medical device may include two or more of a guide wire, an aspiration catheter, and a stent-retriever and the invasive device may be a component of one or more of these, including all of these.

The inventor has recognized and appreciated that conventional medical devices, including conventional thrombectomy devices, do not provide information on characteristics of lesions of vasculature including blood vessels, nor do the conventional medical devices provide information on status of treatment of a lesion. The inventor has additionally recognized and appreciated that this lack of information contributes to difficulties of treating lesions. For example, without information on a composition of a lesion, a clinician may have difficulty selecting between available treatment options, as each treatment option may work best for lesions of different compositions. Moreover, without information on a status of a treatment for a lesion, the clinician may not be aware of whether a treatment is being successfully or unsuccessfully performed. Because of this lack of information, multiple treatments may be necessary to correctly treat a lesion. Each such treatment increases risk of injury to a patient and, more importantly for some lesions, increases the duration of lesion. When a vessel is partially or fully blocked by a lesion, the decreased blood flow may cause injury to tissues of the animal.

Accordingly, in accordance with embodiments described herein, a medical device may determine characteristics of a lesion and monitor performance of a treatment, as well as generate recommendations on a manner in which to treat a lesion before and/or during the treatment. This additional information may aid a clinician in initially determining how to treat a lesion, as well as in performing the treatment to try to ensure that, or at least increase a chance that, a lesion is removed with only one treatment and that subsequent treatments are not needed for the same lesion. The medical device may provide information to the clinician in real-time, during a medical intervention, such as by providing real-time information to the clinician on interactions between the medical device and the lesion. Real-time may, in some embodiments, include providing information to the clinician within a time period of corresponding data being sensed by the medical device, where the time period may be less than 5 seconds, less than 10 seconds, less than 30 seconds, less than one minute, or less than 5 minutes, which may be dependent on requirements of an analysis to be performed on data to generate recommendations.

It should be appreciated that, while examples are described below in connection with lesions of ducts, not all lesions are formed within ducts, and that some embodiments may operate with lesions disposed in areas of the body other than ducts. For example, some cancerous cells may be formed on other parts of an animal (e.g., a human) body. Some embodiments described herein relate to diagnosis and/or treatment of lesions, such as cancerous cells, that are not typically found within ducts. It should be appreciated, however, that some cancerous cells may be found within ducts, and other embodiment described herein relate to diagnosis and/or treatment of such cancerous cells.

It should also be appreciated that while some examples described below relate to lesions, embodiments are not limited to operating with lesions and may operate with any biological structure of interest, having any suitable composition of biological materials.

General Discussion of Techniques

Figure 2:
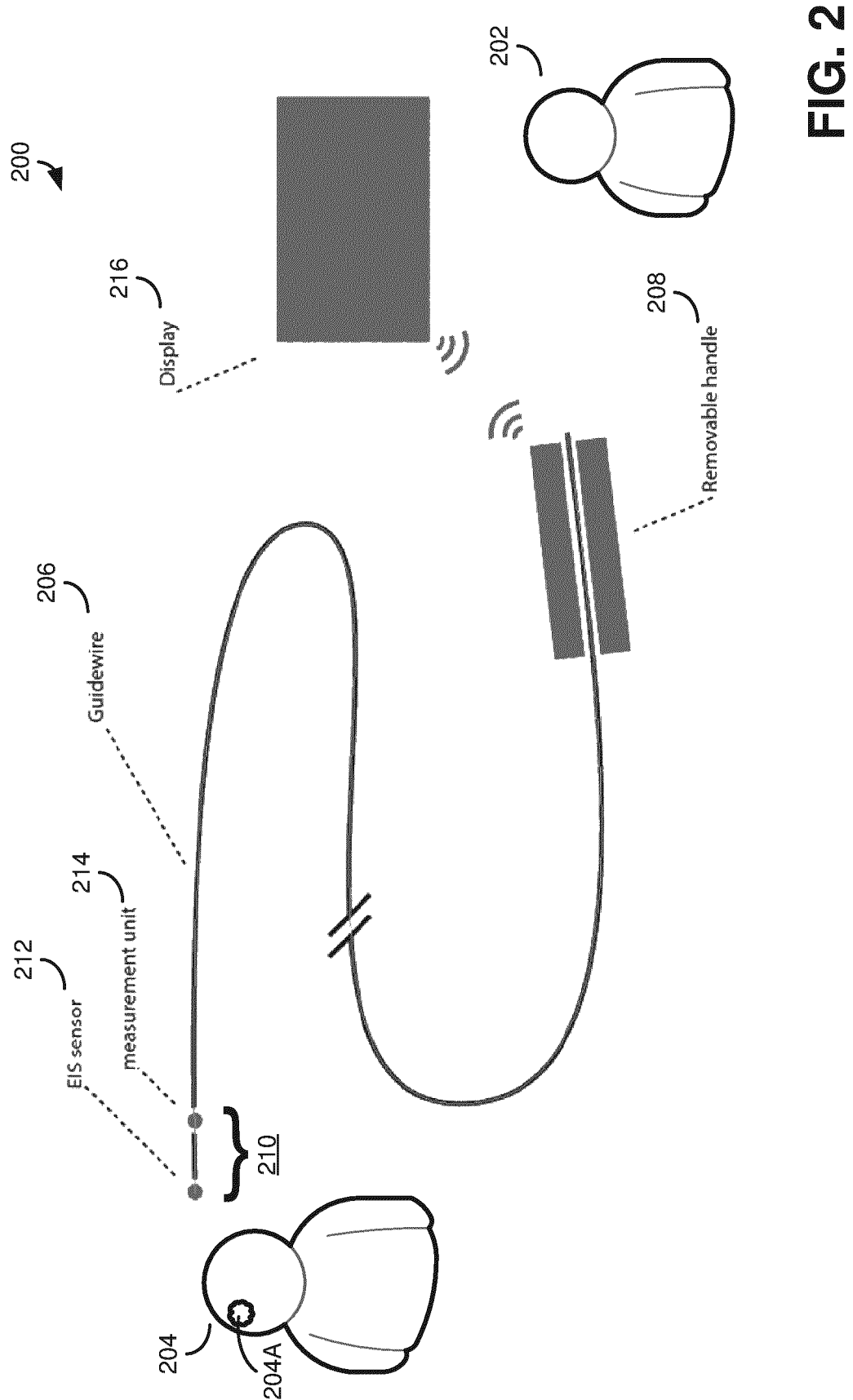
FIG. 2 is an illustration of an example of a medical device in accordance with some embodiments.
Figure 3:
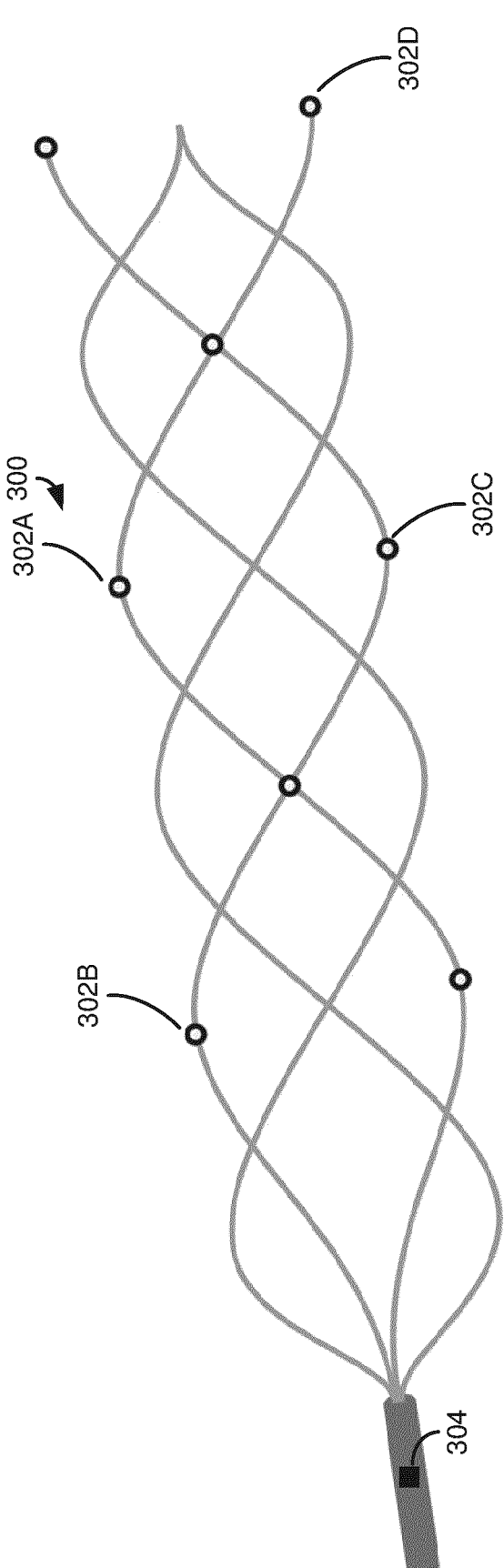
FIG. 3 is an illustration of an example of an invasive probe in accordance with some embodiments.

To provide context for a discussion of exemplary components of a medical device operating in accordance with some embodiments described herein, FIG. 1 is a flowchart of a process that may be followed by a clinician to operate such a medical device. FIGS. 2-3 illustrate examples of a medical device, while other figures below detail other components of a device and ways in which such a device may be operated.

The process 100 may be used to diagnose and/or treat a lesion in a subject that is an animal. The animal may be, for example, a human or a non-human animal, including a human or non-human mammal. The lesion may be a lesion within a duct, such as within a blood vessel like a vein or artery of the animal. A duct lesion may be fully or partially blocking the duct. Embodiments described herein may operate with lesions of different characteristics, such as:

in vasculature, a blood clot (including red blood cells, white blood cells, fibrins, thrombi, emboli, and/or platelets) that formed at the site of the lesion or formed elsewhere in the body and became stuck at the site of the lesion;

a growth from the duct wall toward a center of the duct, such as a growth of scar tissue following an injury to endothelial cells at the site of the lesion or other growth;

tissue (e.g., smooth muscle cells, elastic fibers, external elastic membrane, internal elastic member, loose connective tissues, and/or endothelial cells) otherwise extending from a wall of the duct toward a center of the duct that is not anatomically "normal" or "healthy" for that duct at that site;

an accumulation of plaque materials at the site of the lesion, including an accumulation of cholesterol, calcium, fatty substances, cellular waste products, fibrin, and/or other materials that may be found within fluids flowing through a duct of an animal (e.g., substances found within blood of an animal, in the case of a vasculature lesion);

cancerous cells found in ducts such as metastases and/or lymphomas; and/or any other tissues and/or biological materials that may cause a lesion of a duct of an animal.

Lesions of different characteristics may be formed outside ducts. These lesions include cancerous cells such as carcinomas, myelomas, leukemia, lymphoma, melanomas, neoplasms, mixed type and/or sarcomas.

In some embodiments, the histology of a lesion (e.g., which of the biological materials listed above the lesion possesses) may be determined through identifying, based on a plurality of impedance spectra for the lesion, a composition of a lesion, where the composition may indicate biological materials present in the lesion. Such an identification of biological tissues may include identifying tissues and/or cells that are present in the lesion, and/or plaque materials present in the lesion, and/or the relative amounts of such tissues, cells, or plaque materials in the lesion. In some embodiments, identifying the biological materials present in the lesion may include identifying a state of each biological material, such as, for tissues/cells, whether the tissues/cells are healthy or unhealthy. An unhealthy state of a cell may include, for example, whether the cell is inflamed, diseased, cancerous, or otherwise in an abnormal state.

It should be appreciated that embodiments are not limited to operating with lesions of any particular form or composition, or at any particular locations within an anatomy of a subject. As mentioned above, for case of description, various examples will be provided below in which the duct is vasculature of an animal.

Prior to the start of process 100 of FIG. 1, the subject may exhibit symptoms of a vasculature lesion. An initial determination may be made by a clinician of whether there is a lesion and a potential location of the lesion, such as using imaging techniques like angiography. Based on the symptoms and the initial determination of a location of a lesion, a clinician may choose to insert an invasive device into vasculature of the subject to further diagnose and/or treat the lesion. The clinician may be, for example, a doctor (e.g., a physician or surgeon) or may be another medical professional such as a nurse or medical technician operating the medical device (potentially under a doctor's oversight). In some embodiments, the clinician may be located in the same room as the subject, including next to the subject, while in other embodiments the clinician may be located remote from the subject (e.g., in a different room of the same building as the patient, or geographically remote from the patient) and operating a user interface that controls the medical device via one or more wired and/or wireless networks, including the Internet or other wide area network (WAN).

The process 100 begins in block 102, in which a clinician inserts an invasive probe into vasculature of the subject. The invasive probe inserted by the clinician in block 102 may be located at a distal end of a guide wire for the medical device, and may be shaped, sized, and arranged for insertion into vasculature. In addition, in block 102, the clinician may feed the invasive probe through the subject's vasculature until the invasive probe is located proximate to the lesion. To do so, the clinician may monitor a position of the invasive probe within a subject using imaging techniques, such as using angiography techniques. The insertion and feeding of the invasive probe in block 102 may be performed using suitable techniques for insertion of devices into vasculature, including using known techniques, as embodiments are not limited in this manner.

In block 104, the clinician operates the invasive probe to determine one or more characteristics of the lesion. A characteristic may include a phenotype and/or genotype of a biological structure like a lesion, including a property that distinguishes between biological structures or distinguishes between phenotypes of biological structures. A characteristic may be a property that impacts treatment of the lesion (or other biological structure), as lesions having the property may be treated from lesions not having the property, or lesions having different values for the property may be treated differently. Such properties may be histological, relating to an anatomy of the lesion, and/or anatomical, relating to how the lesion is positioned in or interacts with the body of the animal. A characteristic may therefore describe a lesion. Illustrative characteristics include a location of the lesion, a size of the lesion (e.g., length), a composition of the lesion, or other characteristics discussed in detail below. To determine the characteristics, one or more sensors of the invasive probe may make one or more measurements of tissues and/or other biological materials of the lesion, and/or of tissues/materials otherwise at the site of the lesion such as healthy tissues disposed near the lesion. Examples of sensors and measurements are described in detail below. To operate the invasive probe in block 104, the clinician may contact the lesion with the one or more sensors of the invasive probe, and/or operate a user interface of the medical device to trigger the invasive probe to use the sensor(s) to detect the characteristics of the lesion.

In some embodiments, determining one or more characteristics of the lesion may comprise identifying the composition of the lesion, for example by identifying the amount of different type of cells or tissues that are present in the lesion. As one example, it may be identified that a probed lesion is composed of 50% red blood cells, 30% fibrin and 20% platelets.

In block 106, the clinician operates the medical device to generate and output treatment recommendations for the lesion based on the determined characteristic(s) of the lesion. As discussed in detail below, the treatment recommendation(s) generated by the medical device based on the characteristic(s) of the lesion may include recommendations on a manner in which to treat a lesion, such as which treatment device to use to treat a lesion (e.g., if material of the lesion is to be removed from the subject, whether to use an aspiration catheter or a stent-retriever) and/or a manner in which to use a treatment device (e.g., how fast to extract a stent-retriever). As also discussed in detail below, the medical device may generate the treatment recommendations based on a variety of analyses, such as by comparing the characteristic(s) of the lesion to conditions associated with each of multiple different treatment options and outputting a recommendation of a treatment option when characteristic(s) of the lesion satisfy corresponding conditions for the treatment option. The output by the medical device may be via any suitable form of user interaction, including a visual, audible, and/or haptic feedback to the clinician via the user interface. In some embodiments, the medical device may in block 106 automatically, without further user intervention, analyze characteristic(s) of the lesion determined in block 104 and generate/output the treatment recommendations. In other embodiments, the clinician may operate the user interface of the medical device to request the analysis and generation/output of the treatment recommendations.

In block 108, the clinician considers the treatment recommendations of the medical device and selects a treatment option and, in block 110, treats the lesion using the selected treatment option.

In some embodiments, the selected treatment option may include insertion of additional invasive medical components into vasculature of the subject. If the invasive probe inserted in block 102 was a component of a guide wire, for example, an additional treatment device may be inserted along the guide wire. As a specific example of such a case, if the medical device recommends full or partial removal of the lesion using a stent-retriever, a stent-retriever may be inserted into the vasculature. As another example, if the medical device recommends removal instead with an aspiration catheter, the clinician may insert an aspiration catheter into the vasculature. As a further example, if the medical device recommends implantation of a stent, a stent implanter may be inserted into the vasculature.

In other embodiments, the treatment may not require insertion of another device. For example, the invasive probe inserted in block 102 may not be a component of a guide wire, but may instead be a component of treatment device such as a stent-retriever. In such a case, the treatment of block 110 may be performed using the treatment device that was inserted in block 102. For example, if the invasive probe inserted in block 102 is a component of a stent retriever, the treatment recommendation of block 106 may be specific to a manner of operating a stent-retriever, such as an amount to expand the stent, an amount of time to wait for a clot to coalesce with the stent, and/or a force or speed with which to withdraw the stent and clot. In such an embodiment, in block 110, the clinician may treat the lesion by operating the stent-retriever as recommended by the medical device in block 106.

Once the lesion is treated in block 110, the process 100 ends. Additional actions that may be taken in some embodiments following treatment of a lesion are described below.
Examples of Medical Devices As discussed above, FIG. 1 provided a general discussion of a manner in which a medical device may be operated in accordance with some embodiments described herein to diagnose and/or treat a lesion in vasculature of an animal. FIGS. 2-3 provide examples of some embodiments of a medical device that includes an invasive probe that may be inserted into vasculature as part of such diagnosis and/or treatment.

FIG. 2 illustrates a medical device 200 that may be operated by a clinician 202 to diagnose and/or treat a medical condition of a subject 204. The medical condition of the animal 204 (e.g., a human) may be a lesion 204A of vasculature, illustrated in the example of FIG. 2 as a lesion within a cranial blood vessel of a human, which may cause an ischemic stroke. As discussed above, the lesion 204A may be a blood clot, accumulation of plaque, excessive growth of smooth muscle tissue, and/or other lesion of a blood vessel.

The medical device 200 as illustrated in FIG. 2 includes a guidewire 206, a handle 208, and an invasive probe 210. The invasive probe 210 and at least some of the guidewire 206 may be inserted into vasculature of the subject 204 until the invasive probe 210 is located proximate to the lesion 204A. The invasive probe 210 may therefore be shaped and otherwise arranged for insertion into the vasculature (or other duct). In some embodiments, the invasive probe 210 will be attached to a guidewire that is approximately 300 micrometers, or a microcatheter that is approximately 300 μm to 4 mm in diameter, or another device having a diameter suitable for insertion into a duct of an animal. Such a device may be approximately 1 or 2 meters long in some such embodiments, with the invasive probe 210 located at one end of the guidewire/device, for example within last 5 centimeters of the device.

The invasive probe 210 that is inserted into the subject 204 may include one or more sensors 212 and a measurement unit 214. In some embodiments, the sensor(s) 212 may measure one or more electrical characteristics of the lesion 204A, including by measuring one or more electrical characteristics of tissue and/or biological material of the lesion 204A. The measurement unit 214 may receive data generated by the sensor(s) 212 and may, in some embodiments, generate one or more electrical signals to be applied to the lesion 204A as part of measuring the one or more electrical characteristics.

Examples of sensors 212 are described in detail below. As one specific example, the sensor(s) 212 may be impedance sensors and the measurement unit 214 may drive the sensor(s) 212 to perform Electrical Impedance Spectroscopy (EIS) of the lesion 204A. For example, the measurement unit 214 may include one or more oscillators to produce electrical signals of one or more frequencies, which may be specific frequencies that are selected (and that the oscillators of the measurement unit 214 are configured to produce) for discriminating between different tissues and/or different biological materials, to aid in identifying composition of a lesion 204A, as discussed in detail below. In embodiments that are arranged to test tissues/materials using multiple frequencies, the measurement unit 214 may include multiple oscillators, one oscillator being specific to each frequency to be tested and being arranged to generate a signal of that frequency.

In some embodiments in which the measurement unit 214 generates electrical signals to be applied to the lesion 204A, it may be advantageous for the measurement unit 214 to be included within the invasive probe 210 and inserted into the vasculature of the subject 204. This may place the measurement unit 214 in close proximity to the sensors 212 and lesions 204A, and limit noise in electrical signals applied to the lesion 204A. If the measurement unit 214 were located in the handle 208, for example, electrical signals generated by the measurement unit 214 would travel the length of the guidewire 206 before being output by the invasive probe 210 to be applied to the lesion 204A. If the signals were to travel the length of the guidewire 206, electrical noise may affect signal quality. By positioning the measurement unit 214 within the invasive probe 210, noise in the signals may be limited. When the measurement unit 214 is positioned within the invasive probe 210, it may be positioned within a lumen of the invasive probe 210, on a surface (interior or exterior) of the invasive probe 210, or embedded in a film affixed to a surface (interior or exterior) of the invasive probe 210.

The measurement unit 214 may, in some embodiments, be arranged as an Application Specific Integrated Circuit (ASIC). In some such embodiments, the ASIC may be manufactured using packaging processes that reduce silicon substrate layers. For example, during manufacturing, an integrated circuit may be manufactured with "active" silicon layers that include functional components on top of silicon substrate layers that do not include active components. The substrate layer may be the bottommost layer in the stack of layers, and in some cases may be the thickest layer. Conventionally, the substrate layers are left intact following manufacturing, to lend structural stability to the integrated circuit. In some embodiments, the measurement circuit 214 may be manufactured using a process that includes removing silicon substrate layer following manufacture of the active layer and before packaging. The manufacturing process may include removing the substrate from the bottom surface of the wafer, which may be a side opposite from the side on which the active components were manufactured. In some embodiments, all of the silicon substrate may be removed. In other embodiments, substantially all of the silicon substrate may be removed, where "substantially" removed includes leaving only enough silicon substrate to ensure proper electrical functioning of the active layer components, without leaving silicon substrate solely for structural support. After removal of the silicon substrate, the integrated circuit may be encased in a packaging material.

In some embodiments, placing the measurement unit 214 in close proximity to the sensors 212 and lesions 204A may limit the distance traveled by the electrical signals thus reducing signal attenuation. The reduction in signal attenuation may be particularly significant at higher frequencies, since electrical wires tend to exhibit low-pass frequency response. By reducing the distance traveled by the signals, the cut-off frequency of the electrical path between the signal source and the lesions may be increased, thereby increasing the range of frequencies that can be used in a diagnosis or a treatment. As a result, the ability to differentiate types of tissues or cells can be significantly enhanced. Placing the measurement unit 214 in close proximity to the sensors 212 and lesions 204A may increase the cut-off frequency up to 1 MHZ in some embodiments, up to 10 MHz in other embodiments, or up to 25 MHz in yet other embodiments. For comparison, when measurement unit 214 is located in the handle 208, the cut-off frequency may be limited to less than 500 KHz.

It should be appreciated that embodiments are not limited to the sensor(s) 212 being EIS sensors or being driven to perform EIS operations. In some embodiments, the sensor(s) 212 may be or include one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors. These sensors may include known, commercially-available sensors.

In some embodiments, the measurement unit 214 included in the invasive device 210 may be configured to drive the sensors 212 and/or process results from the sensors to generate data to be sent back along the guidewire 206 to the handle 208. This may be the case, for example, in embodiments in which treatment recommendations are to be generated by the medical device 200. Data indicative of characteristic(s) of a lesion 204A may be transmitted along the length of the guidewire 206. To limit effects of noise during such a transmission, in some embodiments the measurement unit 214 may include an analog-to-digital converter (ADC) or other component to generate digital data for transmission via a communication channel (e.g., one or more wires) running through the guidewire 206.

In accordance with embodiments described herein, the clinician 202 may treat the lesion 204A in accordance with one or more treatment recommendations generated by the medical device 200. While not illustrated in FIG. 2, the medical device 200 may include a controller to generate and output such treatment recommendations for treatment of the lesion 204A. The controller may, in some embodiments, be implemented as a lesion analysis facility, implemented as executable code that is to be executed by at least one processor of the medical device 200. The lesion analysis facility may analyze characteristic(s) of the lesion 204A determined by the medical device 200 (e.g., by invasive probe 210) in connection with configured information regarding one or more treatment recommendations. As one specific example, discussed in detail below, the lesion analysis facility may compare the characteristic(s) of the lesion 204A to conditions associated with various treatment recommendations and output a treatment recommendation when the characteristic(s) satisfy the condition(s) for that treatment recommendation.

In some embodiments, the processor to execute the lesion analysis facility and the storage medium (e.g., memory) storing the lesion analysis facility and the configured information for the treatment recommendations may be disposed within the handle 208. The lesion analysis facility executing on the processor(s) in the handle 208 may therefore receive from the measurement unit 214, via the communication channel of the guidewire 206, data indicative of one or more characteristics of the lesion 204A.

In other embodiments, however, the processor to execute the lesion analysis facility and the storage medium (e.g., memory) storing the lesion analysis facility and the configured information for the treatment recommendations may be disposed separate from the guidewire 206 and handle 208, such as by being disposed in a separate computing device. The computing device may be located proximate to the guidewire 206 and handle 208, such as by being located within the same room. The computing device may alternatively be located remote from the guidewire 206 and handle 208, such as by being located in a different room of the same building or geographically remote from the guidewire 206 and handle 208. In embodiments in which the processor/medium are separate from the guidewire 206 and handle 208, the computing device may receive the data indicative of the one or more characteristics of the lesion 204A via one or more wired and/or wireless communication networks, including a direct wire from the handle 208 to the computing device, a Wireless Personal Area Network (WPAN) between the handle 208 and the computing device, a Wireless Local Area Network (WLAN) between the handle 208 and the computing device, a Wireless Wide Area Network (WWAN) between the handle 208 and the computing device, and/or the Internet. Accordingly, in some embodiments the handle 208 may include one or more network adapters to communicate via one or more networks.

When treatment recommendations are generated by the medical device 200, the treatment recommendations may be output by the medical device 200, for presentation to the clinician 202 and/or any other user. The output may be via one or more networks to another device and/or to one or more displays, such as display 216, or other form of user interface. In the example of FIG. 2, the lesion analysis facility may execute on a processor disposed within the handle 208 and generate treatment recommendations, and the recommendations may be output via a wireless network adapter of the handle 208 to the display 216 for presentation to the clinician 202. Other forms of user interface may be used, as embodiments are not limited in this respect. Any suitable visual, audible, or haptic feedback may be used. For example, if a treatment recommendation is to recommend between removal of a lesion using either an aspiration catheter or a stent-retriever, the handle 208 may include a light emitting diode (LED) or other visual element for each option, and present the treatment recommendation by illuminating the appropriate LED. As another example, if a treatment recommendation relates to a manner of operating a stent-retriever and is, in particular, a recommendation of when to begin extraction following a waiting time, a signal to begin extraction may be output using a haptic signal provided via a vibration unit incorporated into the handle 208. Those skilled in the art will appreciate that, as with the computing device discussed above, elements of the user interface may be disposed within the handle 208 or separate from (or even remote from) the handle 208.

Power may be provided to the invasive probe 210 via a power cable extending along a length of the guidewire 206. The power cable may connect to a power supply in the handle 208, which may be a battery, an energy harvester, a connection to grid power supply, or other energy source, as embodiments are not limited in this respect.

In some embodiments, the handle 208 may include one or more sensors, not illustrated in FIG. 2. The sensor(s) incorporated in the handle 208 may monitor operation of the medical device 200, to inform a manner in which a treatment was performed by the clinician 202. For example, an accelerometer or other movement sensor may be arranged in the handle 208, to detect movement of the handle 208 that governs movement of the guidewire 206 and invasive probe 210. For example, by monitoring the accelerometer, a determination may be made of whether the clinician 202 performed multiple treatments to remove a lesion (e.g., multiple passes with an aspiration catheter or stent-retriever) or was able to extract the lesion with only a single pass.

In some embodiments, the handle 208 may be removable from the guidewire 206 and may be reusable between operations. Accordingly, while an invasive probe 210 and/or guidewire 206 may be arranged not to be reusable and may instead be arranged to be disposable for hygienic reasons, the handle 208 may be arranged to be removably attached to the guidewire 206 and reused with other guidewires 206 and invasive probes 210. For example, the guidewire 206 and the handle 208 may have complementary interfaces to allow the handle 208 to connect with the guidewire 206 and interface with components of the guidewire 206 (e.g., a communication channel, a power cable) and the invasive probe 210.

The clinician 202 may operate the medical device 200 via a user interface of the medical device, which include a display 216 and may be at least partially disposed within the handle 208. For example, the handle 208 may enable the clinician 202 to move the guidewire 206, and the invasive probe 210, forward and back within the vasculature and/or trigger operations of the invasive probe 210.

Operations of the invasive probe 210 may depend on components of the invasive probe 210. For example, the invasive probe 210 may include the sensor(s) 212 to sense one or more characteristics of the lesion 204A. The invasive probe 210 may additionally include the measurement unit 214 to operate the sensors to detect the one or more characteristics, such as by operating the one or more sensors to apply an electrical signal to the lesion 204A and make one or more measurements of the lesion 204A during and/or following application of the electrical signal. In some embodiments, the invasive probe 210 may include one or more components to treat a lesion 204A, including by implanting a stent and/or by removing the lesion 204A. Lesion removal components may include those related to any suitable techniques for removal of lesions, as embodiments are not limited in this respect. In some embodiments, for example, an invasive probe 210 may include stent-retriever components (e.g., a balloon) to perform a lesion retrieval using a stent, and/or aspiration catheter components to aspirate a lesion into a catheter. The invasive probe 210 may additionally include other sensors not shown in FIG. 2, including, for example, optical coherence tomography (OCT) sensors.

The user interface of the medical device, which may be incorporated in whole or in part in the handle 208, may therefore enable the clinician 202 to perform a number of different operations with the invasive probe 210. For example, a user interface of the handle 208 may enable the clinician 202 to trigger sensors 212 and measurement unit 214 to apply an electrical signal and/or make a measurement of the lesion 204A, and/or to perform one or more treatment operations to treat the lesion 204A.

While an example has been described in which medical device 200 may include treatment components to perform one or more operations to treat a lesion 204A, it should be appreciated that embodiments are not so limited. In some embodiments, medical device 200 may be a guide wire for additional treatment devices that are inserted along the guide wire to be positioned proximate to the lesion 204A and to treat the lesion 204A. For example, after insertion of the invasive probe 210 and guidewire 206, the clinician 202 may insert another device along the length of the guidewire 206, or may remove the guidewire 206 and invasive probe 210 and then insert a new device. The newly-inserted device may be, for example, a stent implanter, an aspiration catheter, a stent-retriever, or other device to treat the lesion 204A. In some embodiments in which an additional device is inserted, the handle 208 may be compatible with the additional device, such that the additional device and the handle 208 may have compatible interfaces and a user interface of the handle 208 may be used to operate the additional device.

In addition, while an example has been provided in which a clinician 202 manually operates the medical device 200 in accordance with treatment recommendations, embodiments are not so limited. In alternative embodiments, the medical device 200 may treat a lesion automatically, based on input from sensors 212. For example, as should be appreciated from the brief discussion above and the detailed discussion below, the medical device 200 may generate treatment recommendations on a manner in which to treat the lesion 204A. In some embodiments, the medical device 200, in accordance with the treatment recommendations and without user intervention (though, in some embodiments, under supervision of a clinician 202) insert and/or operate an aspiration catheter, stent-retriever, stent implanter or other device to treat the lesion 204A in accordance with the treatment recommendations.

It should be appreciated that embodiments are not limited to operating with medical devices that are invasive or include an invasive component that is inserted within the body of an animal. For example, non-invasive probes may have measurement units and/or sensors (such as EIS sensors) that operate as described herein, including operating using frequencies or features selected as described herein or using models trained as described herein. Such non-invasive devices may be, for example, used for diagnosis and/or treatment of skin lesions.

It should also be appreciated that techniques described herein are not limited to use with insertable devices such as a guidewire or other tool that may be inserted and then removed, but may also be used with implantable devices. For example, measurement units and sensors of the types described herein may be used with stents, such as where the sensors are positioned directly on the stent. In this way, monitoring of the tissues in the region where the stent is positioned may be performed once and after the stent is in place. The sensors may sense one or more characteristics (e.g., composition) of the tissues in the region where the stent is placed. The sensed characteristics may be used to infer characteristics of one or more biological structures contacted by the stent, to make determinations regarding the one or more biological structures. For example, the system may be used to determine whether a tissue that the stent is contacting is healthy or whether scar tissue or other non-healthy tissue is forming, or whether an occlusion has formed.

FIG. 3 illustrates an example of an invasive probe 210 with which some embodiments may operate. The invasive probe 210 of the example of FIG. 3 includes a mesh 300 that is arranged similarly to a stent. The invasive probe 210 may be operable as a stent-retriever in some embodiments. In other embodiments, the invasive probe 210 may not be operable as a stent-retriever but may include the mesh 300 or another structure to provide multiple points of contact between sensors and a lesion so as to detect characteristics of a lesion with greater accuracy than may be possible using only a single sensor.

Though, it should be appreciated that in some embodiments (not the embodiment of FIG. 3), an invasive probe 210 may include only one sensor, which may be located, for example, at a distal end of the invasive probe 210. Such a sensor may be implemented as two electrodes, one of which may apply an electrical signal to a lesion and one of which may receive the applied signal. Based on a comparison of the applied signal to the received signal, one or more determinations may be made, as discussed in detail below.

The inventor has recognized and appreciated, however, that including additional sensors in the invasive probe 210 may enable more detailed information to be determined. For example, including additional sensors in the invasive probe 210 may enable information on a composition of a lesion to be made with more precision as compared to only a single sensor. Such additional sensors may enable, for example, an impedance spectrum to be determined for each of multiple locations along the invasive probe, such that, in some cases, different impedance spectra may be determined, at different locations, for the same lesion. This may include, for example, determining an impedance spectrum using each sensor. Each impedance spectrum in this case would be the impedance spectrum of a biological material, of the lesion, that a sensor (with its two electrodes) contacts. Some lesions may include multiple different biological materials (e.g., different tissues or cells, or different plaque materials). In a case that each sensor of the invasive probe contacts a different biological material, each sensor may determine a different impedance spectrum, for each different biological material. Though, it may be the case that, for some lesions, two or more sensors of the invasive probe may contact the same biological material and, in such a case, may generate the same or substantially the same impedance spectra. Accordingly, in some embodiments, the invasive probe may operate each sensor to generate an impedance spectrum for a biological material of the lesion. Generating an impedance spectrum for each of multiple biological materials of the lesion (i.e., multiple impedance spectra for each lesion) contrasts with determining a single impedance spectrum for the lesion as a whole. Techniques for determining composition of a lesion using multiple sensors, including through performing EIS, are discussed below.

Accordingly, FIG. 3 illustrates an example of an invasive probe 210 having multiple sensors arranged along an exterior and/or interior surface of the probe 210. The sensors 302 (including sensors 302A, 302B, 302C, 302D, generically or collectively referred to herein as sensor(s) 302) may be arranged along the structure 300. In some embodiments, each sensor may be or include one or more electrodes to apply an electrical signal and/or detect an applied electrical signal.

In some embodiments, while not illustrated in FIG. 3, the invasive probe 210 may include a balloon to, when inflated, expand the structure 300 outward, to better contact a lesion. During use, for example, the structure 300 may be wholly or partially inserted into a lesion, such as until sensors located at a distal end of the structure 300 detect that they have passed to a far side of the lesion, after which the structure 300 may be expanded using the balloon until sensors 302 detect contact at multiple points. The inflation of the structure 300 may be controlled by a controller of the invasive probe 210 (e.g., measurement unit 304) or may be controlled by a lesion analysis facility disposed elsewhere in the medical device and/or by a clinician via a user interface of a medical device.

In some embodiments, a measurement unit 304 may operate the sensors 302 to perform one or more measurements, including by generating one or more electrical signals to apply to a lesion and analyzing data generated by sensors 302. The analysis of the data generated by the sensors 302 may include performing an analog-to-digital conversion of the data to be transmitted along a guidewire to an outside of a patient, such as to a lesion analysis facility or user interface as discussed above.

While examples have been provided in which the sensors 302 are electrical sensors, it should be appreciated that embodiments are not so limited. For example, the sensors 302 may be or include one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors.

Examples of Insertable Devices for In Vivo Sensing

In order to substantially decrease the time it takes a clinician to diagnose and (if applicable) treat a biological structure (e.g., a lesion), such as by removing a clot from a patient's vascular system, the inventor has developed invasive probes having sensors which may be used in determining one or more characteristics of the biological structure. With information on the characteristic(s) of the biological structure, the clinician may be able to differentiate between healthy tissues and different types of lesions, and the clinician may be able to select a treatment most suitable to a particular type of lesion. Described below are embodiments of insertable devices that have designs that can accommodate these sensors while maintaining a size that has been nearly standardized in the marketplace due to its suitability for various human anatomies. In some embodiments, such a design includes probe assemblies having flexible circuits. Being flexible, these circuits can be folded or wrapped as desired, thus substantially limiting the space occupied.

Invasive probes of the types described herein may be implemented as guidewires in some embodiments. Examples of these guidewires are described below in connection with FIGS. 31-44. It should be appreciated, however, that these are merely illustrative of embodiments of the guidewire, and that other embodiments are possible.

Figure 31:
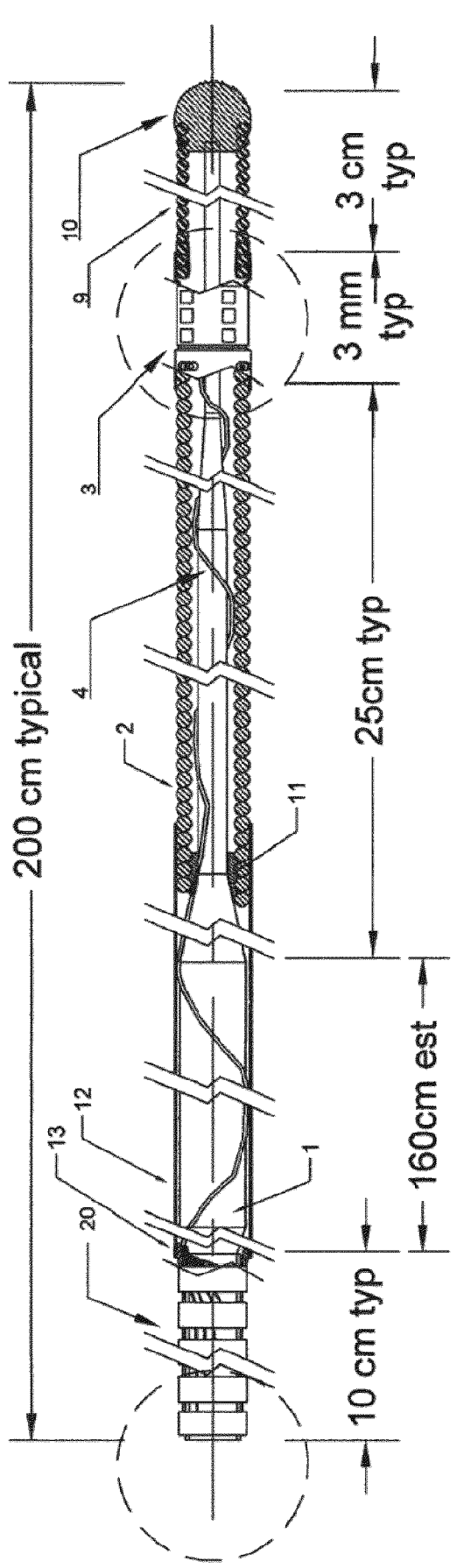
FIG. 31 is a schematic diagram illustrating an example of a guidewire which may be implemented in some embodiments.

An exemplary implementation of an insertable device in accordance with techniques described herein is illustrated in FIG. 31. The example of FIG. 31 is a guidewire that is an insertable device, having an elongate body and a probe having multiple sensors. It should be appreciated, however, that embodiments are not limited to operating with guidewires or insertable devices that are guidewires.

The probe may include sensor assembly 3, coil 9, and tip 10, as well as a distal portion of core wire 1 and other components that extend within the assembly 3, coil 9, and tip 10. The elongated body of the guidewire may include components of the guidewire positioned proximal to the sensor assembly 3 (i.e., to the left of sensor assembly 3 in FIG. 31). The elongated body may thus form the majority of the length of the guidewire of the example of FIG. 31.

Invasive probes of the types described herein may be designed to effectively transfer torque through the length of the probe, and to be sufficiently flexible to be able to navigate through tight curves. As such, these invasive probes are particularly suitable for use in tortuous vessels such as those that may be found on the way from a human torso to the human brain. Torque-ability may be promoted, at least in some embodiments, by using cores having a large tensile strength and by housing the core within a multi-filar coil having one or more wires. The position and number of the coils may be adjusted to provide a desired balance between torque-ability and rigidity. Flexibility may be promoted, at least in some embodiments, by tapering the shape of the core. In particular, the core may be shaped to be smaller in the distal region, thus increasing the core's flexibility where flexibility is most desirable.

Figure 32:
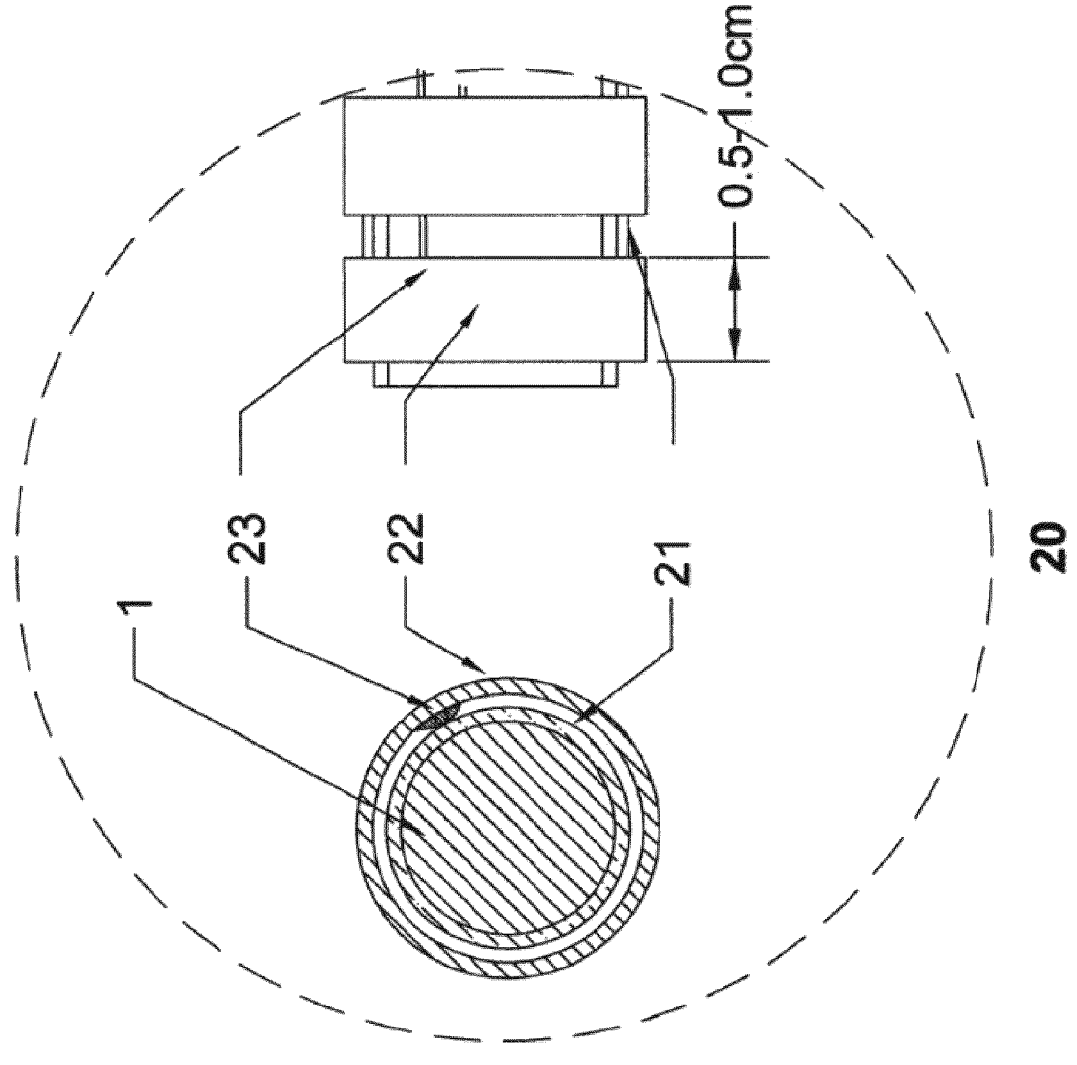
FIG. 32 illustrates an example of a connector assembly which may be used in some embodiments with the guidewire of FIG. 31.

Accordingly, the backbone of the guidewire of FIG. 31 is core wire 1. The core wire 1 is situated, along all of or at least a majority of the elongated body and/or of the probe, at a center of the device, coaxial with the device. Core wire 1 may be made of stainless steel, nickel-titanium or other materials having a large tensile strength, which is a tensile strength above a threshold (e.g., greater than 200 MPa, greater than 350 MPa, or greater than 500 MPa). The core wire may be a centerless ground wire (e.g., a solid core), and may have a gradually tapering distal end in some embodiments. The tapered shape may aid in increasing flexibility of the guidewire at the distal end, which in some cases may aid the guidewire in navigating through tortuous anatomy. As seen in FIG. 32, the wire also includes a proximal ground section in order to accommodate the contact assembly, as discussed below.

An exemplary version of the core wire is made from very high strength 304V Hi-ten stainless steel wire. The largest diameter may be approximately 0.012" (0.30 mm) but could be from 0.008" (0.20 mm) to 0.014" (0.36 mm). A typical length of the wire could be 200 cm but could be as long as 300 cm (such as is typical for an "exchange length" interventional guidewire) or as short as 90 cm or shorter.

Connector assembly 20 may connect the proximal end of core wire 1 to a handle, which may be held by a clinician to steer the guidewire through the patient's vasculature. An electrical connector placed at the proximal end of the guidewire may connect to a handle, which can act as a torque "transmitter," and which may be used to torque and push the guidewire. In some cases, though, the device may be operable without a handle, or may not have a handle. This is because some clinicians prefer to operate an insertable device without the extra weight of a handle, and instead use a classic torquer placed as close as possible to the introducer placed in the patient. In some cases in which a handle is compatible with the insertable device, clinicians such as these would connect the handle only when taking measurements using the sensors of the device.

The distal region of the guidewire may include a sensor assembly 3, which may include one or more sensors. The sensors may be arranged, at least in some embodiments, to detect the impedance of the tissues (e.g., the inner walls of a duct or a clot) surrounding the guidewire. In some embodiments, the sensor assembly 3 may include circuitry for generating probe signals for transmission towards the surrounding tissues and/or circuitry for processing the signals reflected by the tissues. As will be described further below, the sensor assembly 3 is sized and arranged to accommodate the sensor(s) and the circuits in a limited space. The sensor assembly 3 may be located, at least in some embodiments, within the last 7 cm of the distal guidewire, and more preferably about 3 cm proximal to the very end of the guidewire.

The region distal to the sensor assembly 3 may include a coil 9 and a tip 10. Coil 9 may be included to provide the distal end of the guidewire with sufficient flexibility to bend through tight curves. In some circumstances, this portion of the guidewire may be pre-bent (e.g., manually, by a clinician, automatically during manufacturing, or in another manner), before insertion into the patient, with a predefined curvature depending on the ducts through which the guidewire will be inserted. This pre-bend may aid the clinician in steering the guidewire through the patient's vasculature. In some embodiments, coil 9 is made of a material that is radio-opaque, such as platinum, gold, or a platinum alloy such as platinum iridium. Due to its radio-opacity, the position of the guidewire's end may be monitored as it is inserted into the patient, for example via x-ray imaging. Tip 10 may be positioned at the end of the guidewire and may be soldered to coil 9, in some embodiments. Tip 10 may have a curved shape to aid the guidewire in navigating anatomical ducts (e.g., vasculature), such as by sliding against the inner walls of the duct without perforating any tissue. Additionally, or alternatively, tip 10 may be shaped to ensure that the coil assembly (e.g., the multi-filar coil and the distal coil) is held in place relative to the core wire 2. This shape may reduce the likelihood that these coils and/or other distal components separate from the core wire and possibly embolize. This shape of tip 10, to aid in navigation and/or limit the risk of separation/embolizing, may be or include a solder ball in some embodiments.

Coil 9 may be sufficiently short to aid the clinician in positioning the sensor assembly in correspondence with a lesion. In some circumstances, for example, the clinician may push the guidewire forward to the point where the coil 9 passes the lesion, hoping that the sensor assembly 3 has established a contact with the lesion. While the position of coil 9 may be visible thanks to its radio-opacity, the position of the sensor assembly 3 may not (at least in some embodiments). Nonetheless, the clinician may still be able to infer the position of the sensor guidewire based on the position of coil 9. The inventor has discovered that in certain disclosed embodiments, the accuracy with which the position of the sensor assembly relative to coil 9 is inferred can be enhanced by having a short coil. In some cases, if the region appearing in the x-ray image is sufficiently short, the location of the sensor assembly can be easily inferred. At the same time, however, coil 9 may be sufficiently long to be pre-bent by the clinician. Accordingly, in some embodiments, coil 9 may have a length that is between 10 mm and 50 mm, between 15 mm and 50 mm, between 15 mm and 40 mm, between 10 mm and 40 mm, between 15 mm and 30 mm, between 10 mm and 30 mm, between 10 mm and 20 mm, between 30 mm and 40 mm, between 20 mm and 30 mm (such as approximately 25 mm), or between any other suitable values.

The guidewire may form a part of a system that includes the guidewire and a computing device separate from the guidewire, such as the system illustrated in and discussed above in connection with FIG. 2. In such a system, sensor assembly 3 may be placed in electrical communication with a medical device (e.g., a computer) disposed outside the guidewire via one or more wire leads 4. Being solid, the core wire does not include a longitudinal cavity for routing the wire leads therein, as in conventional catheters. Therefore, in the embodiment shown in FIG. 31, the wire lead(s) may be wound around, or otherwise run alongside, core wire 1. The wire lead(s) may be approximately 0.001" (0.03 mm) in diameter, though other sizes are also possible.

The wire leads may be formed of a suitable conductive materials, such as copper, gold, aluminum, or alloys of those materials.

In some embodiments, the lead wires may be individually insulated using an insulating coating, which may be any suitable insulator but may advantageously be polyimide in some embodiments. In some embodiments, the wires may be attached together to form a multi-strand ribbon. Joining the individual wires in this way can add resilience during manufacturing/assembly of the device, as the ribbon can be much stronger that individual leads and reduce the likelihood of breakage or damage during assembly/manufacturing. Joining the leads into a ribbon may also allow for greater control of the wire leads within the device, such as by controlling the order or placement of the leads relative to one another. Controlling order or placement may, in some circumstances, aid in reducing crosstalk between wires, such as by placing a ground wire in between two other wires (e.g., a clock wire and a communication wire, in devices that include those wires), for example.

For instance, the ribbon includes at least three lead wires suitable for any known parallel or serial communication protocol (such as: I2C, UART, SCSI, SPI and so on). In this case, crosstalk between said lead wires is generally observed.

For instance, in the case of SPI (Serial Peripheral Interface) protocol, the ribbon includes five lead wires forming respectively:

a ground wire (GND) and a positive potential wire (VDD) for feeding electric power to the sensor assembly;

a clock wire (CLK) for providing a clock signal to the sensor assembly;

a "Master Out Slave In" (MOSI) wire for conveying an uplink signal from the connector assembly to the sensor assembly (for instance for writing or reading registers in the sensor assembly);

a "Master In Slave Out" (MISO) wire for conveying a downlink signal from the sensor assembly to the connector assembly (for instance for acknowledging orders or for transmitting registers values).

As an example, each lead wire has a diameter of 25 μm and is insulated using a 5 μm-thick insulating coating made of polyimide. Thicker insulation would be beneficial but that would require to reduce the cross-section of the core wire, which would be detrimental for the mechanical properties of the guidewire.

In order to minimize crosstalk between wire leads (for instance, in order to prevent noise propagation from the clock wire to the remaining lead wires), said wire leads are arranged within the ribbon so that the clock wire is placed between the ground wire and the positive potential wire, for example according to the following order: VDD, CLK, GND, MOSI, MISO. This is advantageous, since the ground wire (the potential of which is constant over time) acts as a shield to avoid excessive noise within MOSI and MISO lines due to the clock signal. The same result would be achieved by placing the positive potential wire between the clock wire and any one of the MOSI wire or the MISO wire.

Preferably, a capacitor is provided in parallel with the sensor assembly and is connected to the ground wire and to the positive potential wire for stabilizing the power supply provided through the ground wire and the positive potential wire.

Advantageously, the core wire is made in an electrically conductive material, and is connected to a potential reference (e.g., the ground or the ground wire), either directly or through a capacitor. This feature is advantageous, since it significantly reduces crosstalk between the lead wires through the core wire. Due to such feature, the core wire also acts as an electromagnetic shield against external electromagnetic disturbances arising from the environment surrounding the guidewire.

Preferably, the core wire is connected to the potential reference at the handle 208. This allows for the use of discrete components that are rather bulky, which would not be possible on the invasive probe 210 side. For instance, in the case where a capacitor is used for such connection, said capacitor has a capacitance in the order of 1 μF. However, bigger capacitance values are also beneficial, as they will provide filtering over a larger frequency band, especially for lower frequencies.

Preferably, to mitigate the effects of the establishment time that is inherent to the guidewire (arising from the resistivity of the lead wires and from capacitive coupling) and which causes the uplink signal and the downlink signal to be out of phase, a delay is provided between the uplink signal generation and the downlink signal reading. For example, at the connector assembly, the value of the uplink signal is changed at a falling edge of the clock signal, while the value of the downlink signal is read a quarter of a period later.

Preferably, square signals on the lead wires are avoided, thus removing high frequency harmonics that would cause further interferences.

To electrically isolate the wire lead(s) from the environmental factors (e.g., fluids) that are present in a patient's body, and to mechanically protect the wire leads from torque or friction, a jacket 12 may be used to enclose the wire lead(s). Jacket 12 may enclose, for at least a portion of the guidewire, core wire 1 and wire lead(s) 4. The jacket 12 may extend along a majority of the length of the guidewire, by extending a majority of the length of the elongated body. The jacket 12 may extend more than half of the length of the guidewire and more than half the length of the elongated body. As illustrated in FIG. 31, the jacket 12 may extend along a 160 cm portion of the elongated body, where the total guidewire length (of the example of FIG. 31) is 201 cm and the total length of the elongated body is 195 cm. The jacket 12, in this example, therefore extends 80% of the length of the guidewire and 82% of the length of the elongated body.

Jacket 12 may be made of any of numerous materials, including but not limited to polyimide, polyethylene terephthalate (PETE) or polytetrafluoroethylene (PTFE), or a combination of those and/or other materials.

In some embodiments, jacket 12 is formed via a necking process. For example, the jacketed guidewire may be formed by threading the core wire, the wire leads and the multi-filar coil (or at least a portion of the multi-filar coil) through the lumen of a tubular plastic. The tubular plastic may be formed of a Teflon heatshrink, polyimide, or PET, or other polymer. Some polymers, such as PTFE or PET heatshrink, can be reduced to fit tightly on the core and components just by adding heat. Some polymers may not heatshrink, such as polyimide or PET. Some such other polymers can be reduced in diameter to compress tightly around the core and components by a combination of heat and tension, a process called necking. During a necking process, the material may be heated and stretched, such that a force is applied along the length of the guidewire's elongated body when the material is being applied. Necking will allow for decreasing the diameter of a tube of jacket material from which the jacket is to be formed (e.g., polyimide) to a desired diameter, such as a diameter that will tightly hold the wire lead(s) in place. In one example, the diameter of the jacket is between 0.015" (0.38 mm) and 0.020" (0.51 mm) (such as approximately 0.017", i.e., 0.43 mm) before the necking is performed and is reduced to between 0.012" (0.30 mm) and 0.015" (0.38 mm) (such as approximately 0.014", i.e., 0.36 mm) with the necking. In some embodiments, multiple polymers may be combined to form the jacket. For example, layers of poly-imide and PTFE may be combined. In some such embodi-ments, the layers of different polymers may be discrete layers, rather than layers of mixed polymers. For example, a layer of PTFE may be disposed outside of a layer of polyimide, such that the layer of PTFE is the outer layer. In such an embodiment, the polyimide layer may provide higher strength and precision over the PTFE layer, but the PTFE layer may be disposed outside of the polyimide layer to provide reduced friction as compared to the polyimide layer.

Figure 31A:
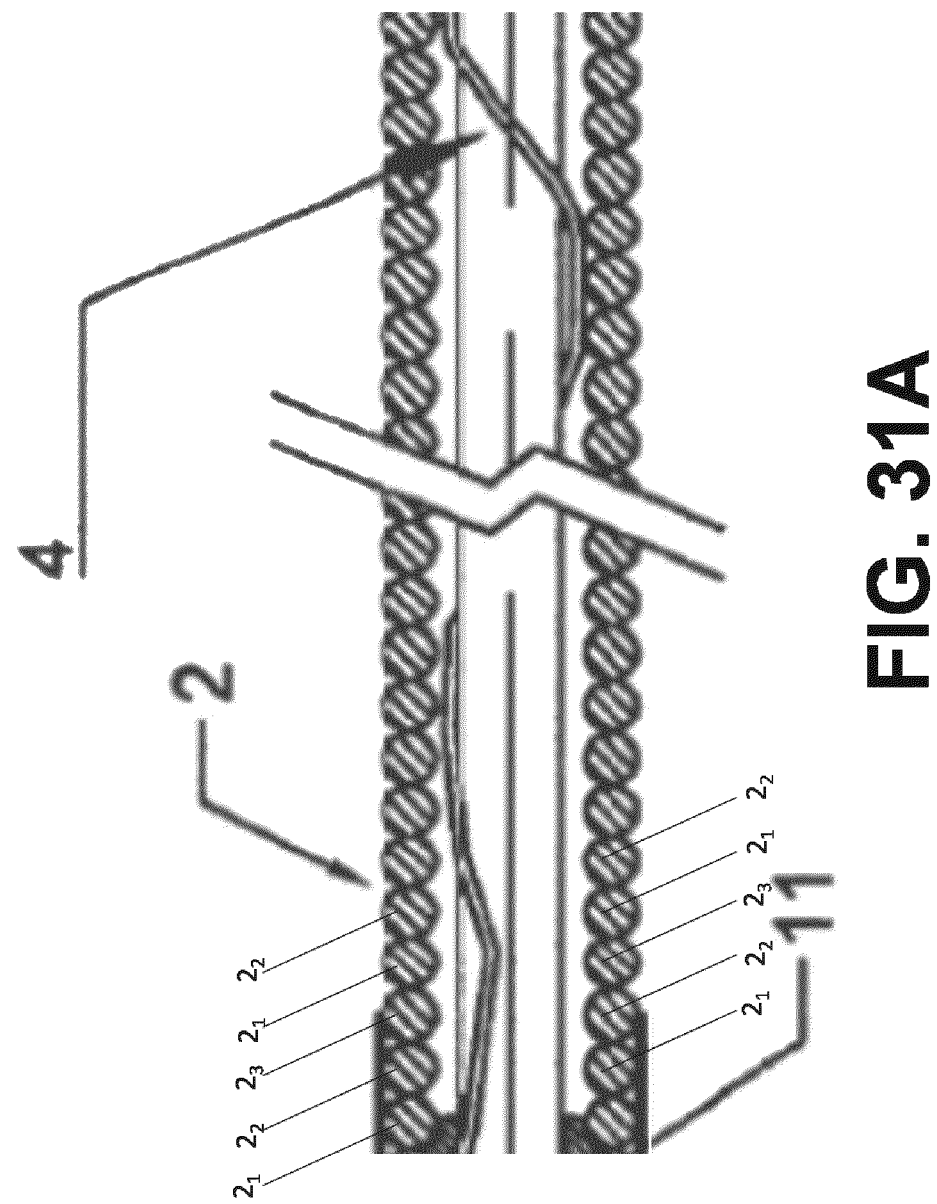
FIG. 31A illustrates a portion of the guidewire of FIG. 31 in additional detail.

In some embodiments, the guidewire is torque-able; that is, the guidewire is able to transmit torque from the proximal portion to the distal portion to be steered by a clinician. Torque-ability can allow the clinician to better control the orientation of the guidewire's distal end, thus facilitating steering of the guidewire along a desired path in the patient's vascular system. To promote torque transmission, in some embodiments, a multi-filar coil 2 is placed over the core wire 1, and then bound to the core wire 1 and/or other compo-nents of the guidewire such as the sensor assembly 3. Multi-filar coil 2 may be made by winding a number of wires, such between one and ten wires or between one and five wires. FIG. 31A, for example, illustrates a portion of a multi-filar coil having three wires (21, 22 and 23) disposed around the core wire, wrapped in a repeating sequential pattern as illustrated. An exemplary version of the coil 2 may be made by simultaneously winding a number of 304v HiTen wires in a coil such that each wire lays next to each other and is closely wound so very little or no space is between each wire. Each wire may have an outer diameter of 0.0015" (0.04 mm) to 0.003" (0.08 mm). The outer diameter of the guidewire including the core wire and the coil 2 may be between 0.010" (0.25 mm) and 0.014" (0.36 mm), such as between 0.012" (0.30 mm) and 0.013" (0.33 mm).

The advantage of a multi-filar coil is the unique ability to positively transmit torque while being very flexible and with a thin wall. The number of wires forming the multi-filar coil may be chosen to provide a desired torque-ability. For example, including an additional wire in the multi-filar coil may increase the torque in some embodiments. In some embodiments, torque may be a linear function of the number of wires included in the coil 2. Further, small increases in wire diameter and/or in coil diameter may also increase torque performance, though at the expense of some flexibil-ity. Thus, a desired torque-ability and flexibility can be selected by adjusting various parameters available in a multi-filar coil.

The stiffness of the guidewire may be adjusted by varying, among other parameters, the separation between adjacent wires in the coil. For example, wires that are packed against each other with virtually no gap in between may result in a stiffer guidewire that is more resistant to movement (less flexible). Separating the wires farther away from each other may increase flexibility of the guidewire and better suited for complex anatomical navigation.

Figure 31B:
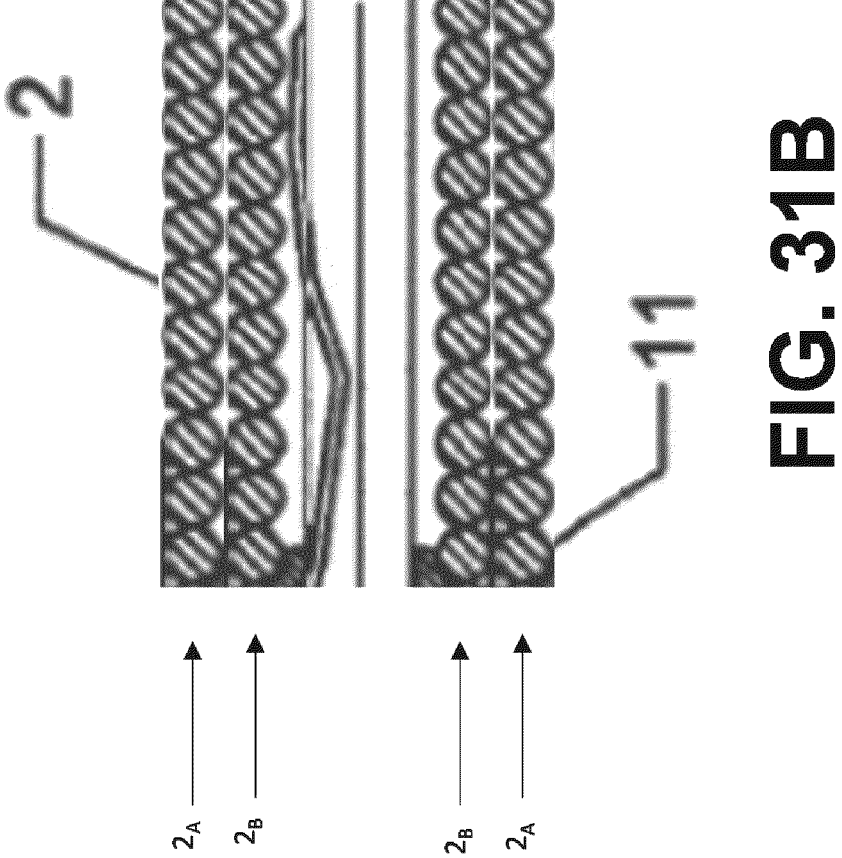
FIG. 31B illustrates a possible implementation for the guidewire of FIG. 31 with multiple rows of multi-filar coils.

In some embodiments, torque transmission may be further increased by including additional coils of the types described above. FIG. 31B, for example, illustrates a portion of a guidewire being wound with two multi-filar coils: $2_A$ and $2_B$. As shown in FIG. 31B, the two filaments may be wrapped in different layers, one on top of the other. In some such embodiments, the two layers may be wrapped in different ways, such as different wind directions and/or with different stiffnesses. Wind direction, called "lay" as in Left lay or Right lay, may have an effect on the nature of the torque-ability in a particular direction. By combining two layers of coils with opposite lay coils, the coil assembly will have similar torque characteristics in both directions. This may be advantageous for some (but not necessarily all) applications. Providing different layers of coil with different properties may further allow for fine selection of torque-ability properties. The multi-filar coil 2 can be connected to the housing hosting the sensor assembly 3 in any suitable manner, such as via laser welding.

The jacket 12 may extend along only a part of the coil 2, at an interface between the jacket 12 and the coil 2. At this interface, where the jacket 12 coextends along the guidewire with the coil 2, the jacket 12 may be wrapped around the coil 2 (as illustrated in FIG. 31) or the coil 2 may be wrapped around the jacket 12. The majority of the length of the coil 2 may extend along a section of the guidewire where the jacket 12 is not present.

In some embodiments, as illustrated in FIG. 31, wire leads for the sensor assembly 3 may extend along the guidewire within the coil 2, disposed between the core 1 and the coil 2. The wire leads may thus extend along the length of the jacket 12 and along the length of the coil 2 to reach the sensor assembly 3, and along the length of the wire leads, the wire leads may be disposed between the jacket 12 and the coil 2.

In order to reduce friction and thus to increase the insertable device's ability to navigate through the patient's vasculature, lubricious coatings may be used in some embodiments. In one example, a hydrophilic coating may be applied to the outer surface of the insertable device, for example to the outer surface of the multi-filar coil (or torque tube) and/or generally to the distal portion of the insertable device. Alternative, or additionally, one or more layers of PTFE may be used as coating along at least a part of the insertable device to reduce friction. The PTFE layer(s) may for example form an outer surface of jacket 12, as discussed above. In some embodiments, friction along the elongated body of the insertable device is reduced with a PTFE outer surface and friction in the probe is reduced with a hydro-philic coating.

Figure 34:
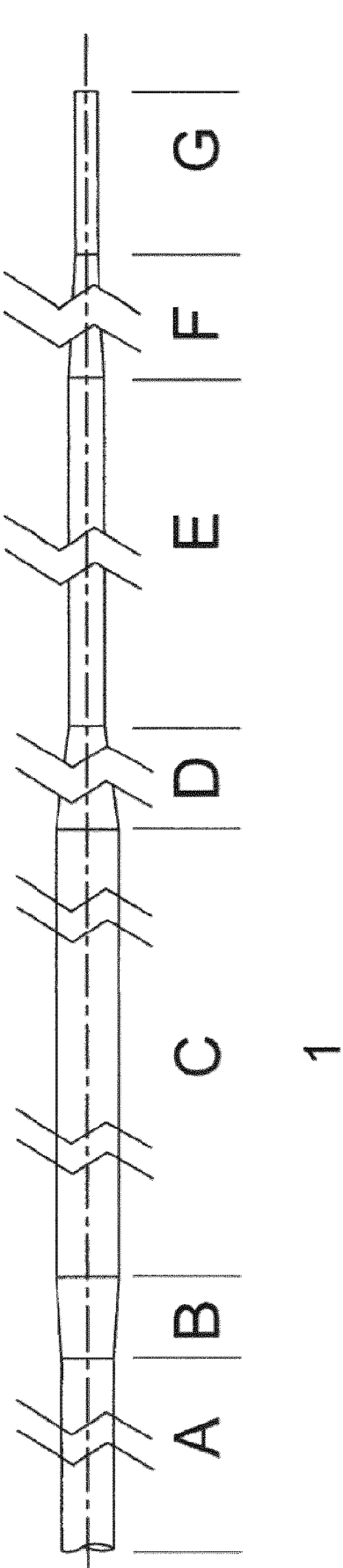
FIG. 34 is a schematic diagram illustrating a guidewire having a plurality of segments, in accordance with some embodiments.

FIG. 31 illustrates possible lengths for different portions of the guidewire. In this non-limiting example, connector assembly 20 is 10 cm long, the untapered portion of the guidewire is 160 cm long, the section between the untapered portion and the sensor assembly 3 is 25 cm long, the sensor assembly is 3 mm-long, and the distal end (including coil 9 and tip 10) is 3 cm-long. Of course, other dimensions, some of which are discussed in connection with FIG. 34, are also possible.

FIG. 32 shows an exemplary implementation of the connector assembly 20, in accordance with some non-limiting embodiments. The connector assembly may be constructed by first mounting an insulator tube 21, made for example of polyimide, over the proximal portion of core wire 1. A contact ring 22, made for example of stainless steel or other easily formed metal tube, is mounted over the insulator, and one wire lead 4 is stripped of insulation and bonded (with bonding material 23) to the contact ring 22. Each subsequent contact ring may be placed and spaced apart in a similar fashion. The insulator tube 21 may be made of polyimide with an outer diameter varying based on the size of the guidewire with which it will operate, such that it will be smaller than the guidewire. For example, the tube 21 may have a diameter between 0.006" (0.15 mm) and 0.014" (0.36 mm) (such as approximately 0.012", i.e., 0.30 mm) for guidewires having a diameter between 0.010" (0.25 mm) and 0.018" (0.46 mm). The tuber 21 may also have a 0.001" (0.03 mm) wall and with a length between 5 cm and 15 cm (e.g., 10 cm). The contact rings 22 may have an outer diameter between 0.012" (0.30 mm) and 0.015" (0.38 mm) (e.g., 0.014", i.e., 0.36 mm) with a 0.001" (0.03 mm) wall, and a length of between 0.5 cm and 1.0 cm. The contact rings can be specifically spaced apart using a polyimide spacer or other tubular plastic spacer of similar diametric size to the contact rings.

As described above, sensor assembly 3 may include sensor(s) and electronic circuits in some embodiments. In order to assemble the sensor(s) and the circuits together with the guidewire, sufficient space is needed. Yet, in some circumstances it may be desirable to limit the diameter of the guidewire to less than (or equal to) 0.014" (0.36 mm), or other suitable values, which renders packaging of the sensor(s) and circuit(s) challenging. In some embodiments, flexible circuits may be used to assemble the sensor(s) and circuits with the guidewire. Being flexible, these circuits may be folded or wrapped, thus limiting the amount of space occupied.

Figure 33:
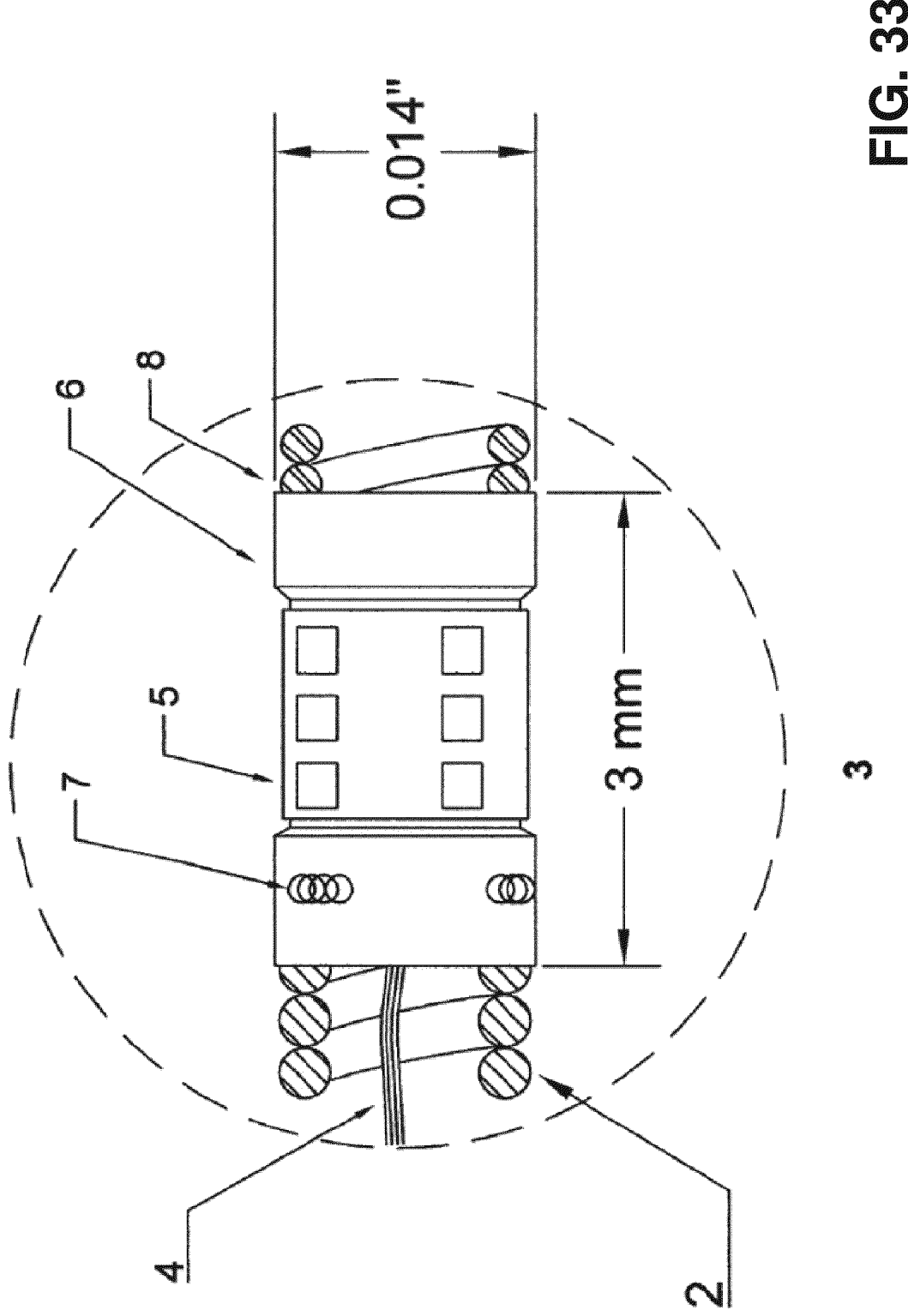
FIG. 33 illustrates an example of a sensor assembly which may be used in some embodiments with the guidewire of FIG. 31.

FIG. 33 shows a portion of the guidewire of FIG. 31 in additional detail, in accordance with some non-limiting embodiments. In this example, sensor assembly 3 comprises a flexible circuit 5 (also referred to as flexible substrate). Flexible circuit 5 may include the electronic circuits and the sensors, and may be supported by a sensor housing 6. In some embodiments, as will be described further below in connection with FIGS. 36A-36B, the flexible circuit may be wrapped around a portion of housing 6. As illustrated, the wire leads 4 may be inserted in the housing 6 and may be connected to the flexible circuit 5. Housing 6 may be attached to the multi-filar coil 2 in any suitable manner, such as using laser welds 7. Additionally, or alternatively, a solder joint, glue or some similar means may be used. Coil 9 may be bonded to the distal end of the sensor housing 6 by a solder joint 8, glue, or similar means.

In some embodiments, the diameter of core wire 1 may be varied along its length to enhance flexibility where needed. In one example, the diameter may be tapered along its length such that the diameter at the distal end is smaller than it is at the proximal end. In this way, the flexibility at the distal end is enhanced relative to the proximal end without necessarily sacrificing torque-ability. FIG. 34 illustrates schematically a core wire 1 having a tapered shape, according to some non-limiting embodiments. In this example, core wire 1 includes segments A, B, C, D, E, F and G. Segment A may include connector assembly 20, and may have a length between 5 cm and 15 cm, such as approximately 10 cm. At segment A, the core wire may have a diameter that is between 0.006" (0.15 mm) and 0.010" (0.25 mm), such as approximately 0.0080" (0.20 mm). Segment B may have a length between 1 cm and 3 cm, such as approximately 2 cm. Segment B may have a tapered-up shape, such that the diameter of the core wire increases to between 0.009" (0.23 mm) and 0.014" (0.36 mm), such as to approximately 0.011" (0.28 mm). Segment C, which may include jacket 12, may have a length between 100 cm and 200 cm or between 130 cm and 170 cm, such as approximately 155 cm. At segment C, the core wire may have a width between 0.010" (0.25 mm) and 0.014" (0.36 mm), such as approximately 0.011" (0.28 mm) or approximately 0.012" (0.30 mm). Multi-filar coil 2 may be included in segment E, and optionally in segments D and/or F or parts thereof. Segment D may have a length between 6 cm and 10 cm, such as approximately 8 cm. Segment D may have a tapered-down shape, such that the diameter of the core wire decreases to between 0.004" (0.10 mm) and 0.006" (0.15 mm), such as to approximately 0.005" (0.13 mm). Segment E may have a length between 7 cm and 13 cm, such as approximately 10 cm. At segment E, the core wire may have a width between 0.004" (0.10 mm) and 0.006" (0.15 mm), such as approximately 0.005" (0.13 mm). Segment F may have a length between 6 cm and 10 cm, such as approximately 8 cm. Segment F may have a tapered-down shape, such that the diameter of the core wire decreases to between 0.002" (0.05 mm) and 0.004" (0.10 mm), such as to approximately 0.003" (0.08 mm). Segment G, which may include sensor assembly 3, coil 9 and tip 10, and may have a length between 4 cm and 10 cm, such as approximately 7 cm. At segment G, the core wire may have a width between 0.002" (0.05 mm) and 0.004" (0.10 mm), such as approximately 0.003" (0.08 mm).

The specific dimensions described above may be engineered to provide a desired amount of torque-ability in the proximal and central portions of the guidewire, a desired amount of flexibility in the last 10 cm-30 cm of the guidewire, and sufficient space to accommodate the sensor(s) and the electronic circuits in the last 3 cm-7 cm. It should be appreciated, however, that not all embodiments are limited to the dimensions provided in connection with FIG. 34.

Figure 35:
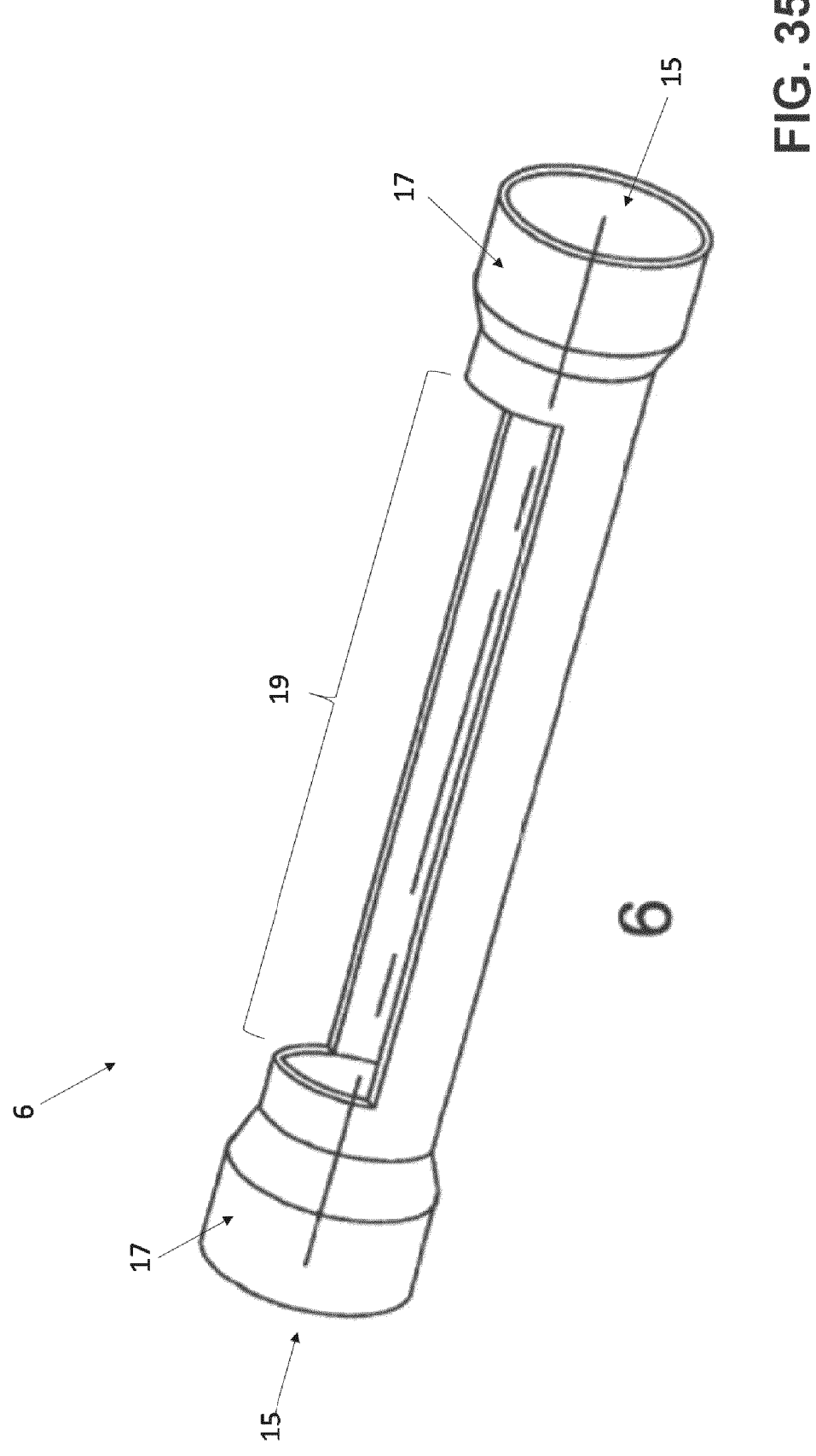
FIG. 35 illustrates an example of a housing which may be used in some embodiments with the guidewire of FIG. 31.

FIGS. 35-36B show more details of the components that make up the sensor assembly 3, according to some non-limiting embodiments. In particular, FIG. 35 shows a perspective view of a possible implementation of sensor housing 6. In some embodiments, housing 6 is formed from a stainless steel tube, though other materials may alternatively or additionally be used.

Housing 6 may be sufficiently short to not compromise the steer-ability of the guidewire in the distal end with its rigidity, while sufficiently long to accommodate the sensors and/or the circuits. In one example, the housing 6 may be approximately between 2 mm and 5 mm in length, between 2 mm and 4 mm, between 2 mm and 4 mm, between 3 mm and 5 mm, between 3 mm and 4 mm (such as approximately 3.5 mm) and between 0.012" (0.30 mm) and 0.015" (0.38 mm) in diameter at its maximum (such as approximately 0.014", i.e., 0.36 mm), though other dimensions are also possible.

Each end of the housing 6 may have an opening 15 through which core wire 1 may be passed. In some embodiments, the regions of the housing near its ends include respective flared or enlarged bosses 17, which may be designed for the multi-filar coil 2 and the coil 9 to be inserted and bonded to the housing.

The center of the housing may have a cut-away recess 19 formed on the side of the housing as shown in FIG. 35. Recess 19 may be formed by removing a portion of the housing's sidewall. Recess 19 may be sized to accommodate flexible circuit 5 (not shown in FIG. 35) therein. For example, recess 19 may be approximately between 1 mm and 2.5 mm in length, such as between 1.3 mm and 1.7 mm.

A portion of the flexible circuit may be inserted inside housing 6 through recess 19, and another portion may be wrapped around the housing, as will be described further below.

FIGS. 36A and 36B show a possible layout of the flex circuit 5, in accordance with some embodiments. The flex circuit 5, which may be made of a flexible material 28 such as polyimide, may include a sensor array 25, integrated circuits 26 (which may include Application Specific Integrated Circuits or other logic circuits), and solder pads 27 for bonding wire leads 4. The integrated circuits 26 may include chips performing functions of a measurement unit, such as measurement unit 214 discussed above in connection with FIG. 2.

Sensor array 25 may include a plurality of sensors for sensing one or more characteristics of the tissues surrounding the guidewire. In one example, the sensor array may be arranged as an impedance sensor array. It should be appreciated, however, that embodiments of the present disclosure are not limited to any specific type of sensor. Possible alternative types of sensors include pressure sensors and flow sensors, though other types of sensors may be used. In at least some of the embodiments in which an impedance sensor array is used, the sensor array may include a plurality of electrodes. In the example of FIG. 36A, nine electrodes are included (2511, 2512, 2513, 2521, 2522, 2523, 2531, 2532, and 2533) arranged in three columns and three rows. Of course, any other suitable number of electrodes may be used. Multiple rows may be included to increase the probability that at least some of the sensors are in contact with the clots to be sampled.

Some of the electrodes may be driven with signals produced by one or both of the integrated circuits 26 (referred to as probe signals), and may cause the signals to propagate outside the guidewire in the form of electromagnetic waves. In this respect, the electrodes behave essentially as antennas. These electrodes are referred to as transmitting (TX) electrodes. The transmitted electromagnetic waves may be reflected by the tissues surrounding the guidewire. The remaining electrodes, referred to as receiving (RX) electrodes, may receive the reflected electromagnetic waves. As discussed in more detail below, in some embodiments, the electrodes may be operated in groups of three, and one of the electrodes of each group may be operated as a TX electrode while the others operate as RX electrodes.

The signals obtained in response to reception of the electromagnetic waves (referred to as detection signals) may be transferred to one or both of the integrated circuits 26 for processing (e.g., analog-to-digital conversion). In some embodiments, the circuits of the integrated circuits may be configured to infer the impedance of the reflecting tissues based on a comparison between the transmitted and the received signals (for example by taking the ratio of the transmitted voltage to the received current). These measurements of impedance may be repeated at different frequencies, thus obtaining the impedance spectral response of the tissue. Data indicative of the impedance measurements may be transmitted to a medical device outside the guidewire for further processing via solder pads 27 and wire leads 4.

While the embodiments described herein are such that separate electrodes are used for the transmission and reception, respectively, of electromagnetic waves, it should be appreciated that in other embodiments the same electrodes may be used for both the transmission and the reception.

FIG. 36B illustrates a possible arrangement of the flexible circuit 5 in relation to housing 6, in accordance with some non-limiting embodiments. As illustrated, one end of the flexible circuit (e.g., the end on which solder pads 27 are disposed) is positioned inside the cavity formed by the housing 6. The wire leads 4, which may be inserted through the housing via openings 15 (shown in FIG. 35), are connected to respective contacts 27 inside the housing. The contacts 27 may be or include solder pads, a silver-filled epoxy, a conductive glue, or other conductive material. The flexible circuit may then be folded or wrapped around core wire 1 (which may also be passed through the housing via openings 15) and may be arranged such that the integrated circuits 26 are positioned, when the flexible circuit is wrapped, in correspondence with recess 19 (shown in FIG. 35). The flexible circuit may be wrapped around the perimeter of housing 6 and arranged such that the integrated circuits 26 are stacked on top of each other at the recess 19 (or inside the cavity). The remaining portion of the flexible circuit may be wrapped around the housing, such that the sensor array 25 is disposed outside the housing and is oriented outwardly relative the housing (i.e., facing away from the housing). In one example, the distances between the electrode rows (the first row including electrodes 2511, 2512 and 2513) are sized such that, when the flexible circuit is wrapped around the housing, the rows are angularly offset by approximately 120°, thereby being evenly distributed around an exterior of the guidewire.

Within each row, some electrodes may be arranged for transmission and other electrodes may be arranged for reception, though the role of each electrode may be changed over time. During one time interval, one electrode for each row may serve as a TX electrode and the other two electrodes may serve as RX electrodes. The TX electrode may transmit electromagnetic waves and the RX electrodes may receive waves reflected from neighboring tissues. In some such embodiments, the different RX electrodes of each row are arranged to detect impedance at different depths within a tissue. This may be accomplished by arranging the RX electrodes to have different distances with respect to the TX electrode. That is, one RX electrode (e.g., electrode 2512) is positioned at a first distance with respect to the TX electrode (e.g., electrode 2511) and another RX electrode (e.g., electrode 2513) is positioned at a second distance with respect to the TX electrode, where the first and second distances are different from each other. Since the distances relative to the TX electrode are different, the RX electrodes receive waves with different incident angles. Waves having different incident angles have different penetration depths into the tissue, and as a result can provide an indication of the impedance at different depths. Detecting impedance at different depths may enhance the ability to characterize the clot (e.g., to infer the clot's type, composition or other characteristics).

Additional details of some embodiments of flexible circuits are provided below.

Figure 41A:
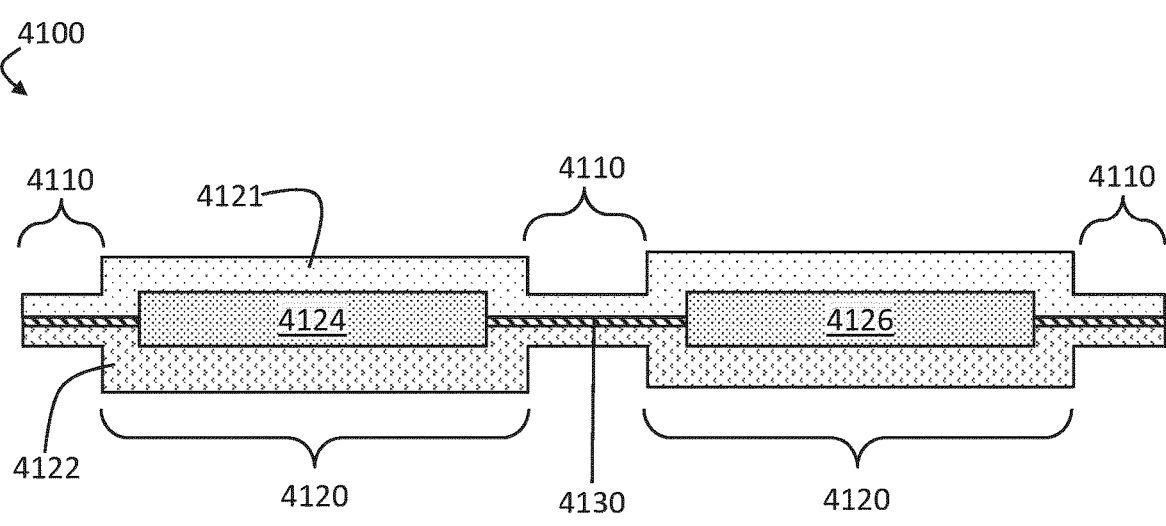
FIGS. 41A-41B are cross-sectional schematic side views of a flexible circuit board, according to some embodiments.
Figure 41B:
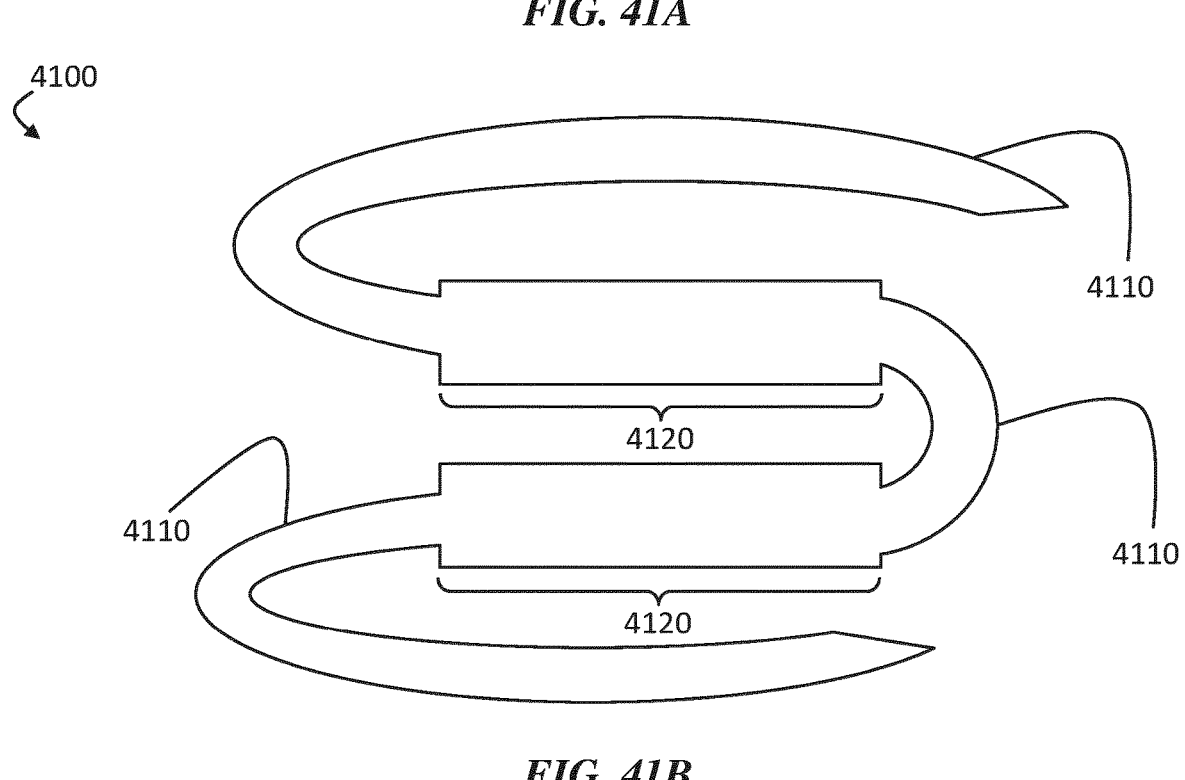

Referring now to FIG. 41A, flexible circuit board 4100 is schematically illustrated. As shown in the figure, the flexible circuit board can comprise first, flexible regions 4110 and second, inflexible regions 4120. In some embodiments, the first region has a flexibility greater than the second region. This may advantageously allow portions of the flexible circuit to wrap around portions of itself and/or other portions of an invasive probe (e.g., a guidewire). For example, as schematically illustrated in FIG. 41B, the flexible regions 4110 can bend and flex around the inflexible regions 4120. More details regarding the degree of flexibility between these two regions are described in more detail elsewhere herein.

The flexible circuit board may comprise a polymer or organic layer, which may contribute to the flexibility of the circuit board. For example, referring back to FIG. 41A, flexible circuit board 4100 may comprise a first polymer layer 4121 and a second polymer layer 4122 disposed on a first integrated circuit 4124, a second integrated circuit 4126, and interconnect layer 4130. As schematically illustrated in the figure, first polymer layer 4121 can be disposed on a top surface of interconnect layer 4130, while the second polymer layer 4122 can be disposed on an opposing back surface of interconnect layer 4130. However, it should be understood that other configurations of the first and second polymer layer are possible, other than the configuration shown in FIG. 41A.

The polymer layer (e.g., the first polymer layer, the second polymer layer) may comprise or be any suitable polymeric or organic material for providing flexibility to the circuit. In an exemplary embodiment, the polymer layer comprises polyimide. However, other polymeric materials are suitable. Non-limiting examples of other suitable polymeric materials include polyolefins, such as, for example, polyethylenes, polypropylenes, polyimides, paralyenes, and polysiloxanes, and benzocyclobutene (BCB). Other polymeric or organic materials are possible.

In some embodiments, the first polymer layer 4121 and the second polymer layer 4122 may have matching flexibility, such that during flexing the two layers, compression and expansion forces acting on the interconnect layer 4130 when flexed in one direction match the compression and expansion forces acting on the interconnect layer when flexed in an opposite direction. This is referred to as being in the neutral plane of the region. Having matching flexibility on the two sides of the interconnect layer 4130, and thus being in the neutral plane, at least in the flexible region can be helpful to increase reliability of the interconnect layer 4130 and of the flexible circuit, by mitigating risk of damage to the interconnect layer 4130 due to flexing. In some embodiments, this matching flexibility may persist through the flexible region 4110 and through a transition between the flexible region 4110 and the inflexible region 4120. Accordingly, in some such embodiments, at each transition between flexible region 4110 and inflexible region 4120, the interconnect layer 4130 may be maintained in a neutral plane between layers 4110, 4120.

In some embodiments, this matching flexibility may be achieved by arranging the thicknesses of the first polymer layer and the second polymer layer so as to provide a desired flexibility to the flexible circuit without damaging (e.g., cracking) the circuit (e.g., interconnect layer 4130 of the circuit 4100). For example, within the first region (e.g., the flexible region), the first polymer layer and the second polymer may have matching thicknesses. Two thicknesses may match when they are identical or are within a threshold tolerance of being identical. In some embodiments, the tolerance for matching thicknesses may be that the flexibility of the two layers are matching or result in applying identical forces or forces within a tolerance of one another to the interconnection layer 4130 during flexing. Tolerance for forces may be that the two forces are nearly equivalent so as to mitigate risk of the interconnect layer 4130 degrading or breaking due to flexing. In some embodiments, the flexibility of the layers 4121, 4122 may be substantially the same or the thicknesses of layers 4121, 4122 may be substantially the same. The term "substantially" as used in this context refers to a majority of, or mostly, as in at least 80%, 85%, 90%, 95%, 96%, 97%, 98%, 99%, 99.5%, 99.9%, 99.99%, or at least about 99.999% or more.

In some embodiments, the first polymer layer and/or the second polymer layer (e.g., within the first region, within the second region) may have a particular thickness. In some embodiments, a thickness of the first polymer layer and/or the second polymer layer is greater than or equal to 1 micron, greater than or equal to 5 microns, greater than or equal to 10 microns, greater than or equal to 15 microns, greater than or equal to 20 microns, greater than or equal to 25 microns, greater than or equal to 30 microns, greater than or equal to 40 microns, greater than or equal to 50 microns, greater than or equal to 60 microns, greater than or equal to 70 microns, greater than or equal to 80 microns, greater than or equal to 90 microns, or greater than or equal to 100 microns. In some embodiments, the thickness of the first polymer layer and/or the second polymer layer is less than or equal to 100 microns, less than or equal to 90 microns, less than or equal to 80 microns, less than or equal to 70 microns, less than or equal to 60 microns, less than or equal to 50 microns, less than or equal to 40 microns, less than or equal to 30 microns, less than or equal to 25 microns, less than or equal to 20 microns, less than or equal to 15 microns, less than or equal to 10 microns, less than or equal to 5 microns, or less than or equal to 1 micron. Combinations of the above-referenced ranged are also possible (e.g., greater than or equal to 1 micron and less than or equal to 100 microns). Other ranges are possible.

As mentioned above, the flexible circuit board may also comprise an interconnect layer, such as interconnect layer 4130 in FIG. 41A. The interconnect layer 4130 of FIG. 41A may be formed by one or more layers of a conductive material (e.g., gold, as mentioned above) that form conductive traces, vias, leads, conductive pads, or other known conductive elements of a circuit board in the flexible circuit board. For case of description, the interconnect layer 4130 is referred to herein as a "layer" (singular terminology), but those skilled in the art should appreciate that the interconnect layer 4130 may include one, two, or another suitable number of layers.

The interconnect layer may provide electrical communication to two or more components, such as a first integrated circuit and a second integrated circuit, between a second integrated circuit and one or more conductive contacts to which one or more wires of the invasive probe are connected, or between a circuit of the invasive probe and electrical circuitry at a proximal portion of the invasive probe, as non-limiting examples.

The interconnect layer may be of any suitable material for providing electric signals to be transmitted from one component to another. In one embodiment, the interconnect layer is or comprises gold. However, other suitable materials for the interconnect layer can be used. In some embodiments, the interconnect layer comprises a conductive metal. Non-limiting examples of interconnect layer conductive metals includes gold, platinum, palladium, nickel, silver, copper, aluminum, and combinations/alloys thereof such as AlSiCu. In some embodiments, the interconnect layer comprises an organic material, such as conductive organic materials like Pedot:PSS (poly(3,4-ethylenedioxythiophenc) polystyrene sulfonate). A conductive interconnect layer may be formed using known techniques such as depositing an entire layer using a technique such as chemical vapor deposition (CVD) or evaporation, or with deposition methods like inkjet printing.

In some embodiments, a position of the interconnect layer (e.g., within the first region, within the second region) is such that a desired flexibility of the flexible circuit can be achieved without breaking or damaging the interconnect layer. In some embodiments, the interconnect layer within the first region (e.g., the flexible region, region 4110 of FIG.

41A) is positioned between (e.g., in the middle of) the first polymer layer and the second polymer layer. In some embodiments, at a transition between the first region and the second region, and within the second region (e.g., the inflexible region, region 4120 of FIG. 41B), the interconnect layer 4130 is positioned nearer a top surface of the first polymer layer compared to a bottom surface of second polymer layer. Nearer the top surface may include in the top third of the flexible circuit. (In this example, "top" is the side of the flexible circuit at which the interconnect layer will form an electrical connection with a lead or other contact for an integrated circuit.) In some embodiments, in the transition between the flexible region 4110 and the inflexible region 4120, the interconnection layer 4130 may remain in a neutral plane between the two layers of the polymer. Staying in the neutral plane may include transitioning from being relatively in the middle between two polymer layers of matching thickness to being in the top portion (e.g., top third) of the device, with the second polymer layer 4122 having a higher thickness below the interconnect layer 4130 than a thickness above the interconnect layer 4130 of the first polymer layer 4121. Other positionings of the interconnect layer within the polymer layer are possible, and those skilled in the art in view of the teachings of the present disclosure will be capable of selecting a position of the interconnect layer to maintain the flexibility of the flexible circuit without damaging the circuit upon flexing of the circuit.

In some embodiments, the flexible circuit board comprises one or more integrated circuits (e.g., "chips"). For example, in FIG. 41A, flexible circuit board 4100 comprises first integrated circuit 4124 and second integrated circuit 4126. The one or more integrated circuits can be an inorganic, solid-state material, such as a silicon chip, and can be relatively rigid or inflexible compared to the organic, polymer layer. In some embodiments, the one or more integrated circuits is disposed within the second region (e.g., the inflexible region). As mentioned above, this provides the flexible circuit board regions of flexibility and regions of relative inflexibility.

In some embodiments, the inflexible region is prepared by positioning an integrated circuit adjacent (e.g., directly adjacent) a second polymer layer and depositing or otherwise forming a first polymer layer adjacent to the integrated circuit. The first polymer layer may be formed to have a certain desired thickness, which may be a desired range of thicknesses (e.g., a target thickness with a tolerance margin to be above or below the target thickness). The thickness dimension in these examples may be the height/vertical dimension in the cross-section of FIG. 41A.

In some embodiments, the desired thickness may be achieved by regulating how material is deposited, applied, grown, or otherwise initially formed into a first polymer layer. In other embodiments, the desired thickness may be achieved by processing a material of the first polymer layer to remove some initially formed material and, through the removal, achieve the desired thickness. For example, in some embodiments, a polymer layer may be deposited or otherwise formed that includes forming the polymer layer over the integrated circuit positioned on the second polymer layer. This initial polymer layer may be of an uncertain thickness, which may be a thickness that was initially uncontrolled or may be a thickness that was controlled in a manner that would obtain a thickness within a desired initial manufacturing range of the desired thickness but not identical to the desired thickness. In such an embodiment, because the initial polymer layer may deviate from the desired thickness but the amount of that deviation may be unknown, the thickness of the initial polymer layer can be determined. This may be determined through measuring the thickness of the initial polymer layer. For example, low-coherence interference microscopy using a laser and interference patterns may be used to measure the thickness. Alternatively, in an embodiment in which at least one area of the flexible circuit is free from the polymer layer (e.g., where the layer was not deposited or was removed), a profilometer may be used to measure step height.

Following the measuring, processing may be performed to remove some of the initial polymer layer, where the amount that is removed is determined based on the measured thickness and is an amount of material that will yield a first polymer layer with the desired thickness. Embodiments are not limited to performing this processing to remove material in any specific manner and known techniques may be used. For example, the initial polymer layer may be etched to achieve the desired thickness. In some embodiments, following the removal of some of the initial polymer layer, conductive contacts may be positioned on the integrated circuit in the region in which the initial polymer layer was processed to remove material.

In some embodiments, the integrated circuits may be encapsulated by a layer or coating, which protect the integrated circuits from substances (e.g., fluids) within a duct that might short or otherwise damage the circuits. For example, the integrated circuits may be encapsulated in a material that is waterproof to allow immersion of the invasive probe in bodily fluids without risk of the bodily fluids interrupting operations of the integrated circuits. In some embodiments, such an encapsulation layer may be or comprise silicon dioxide (e.g., $SiO_2$) and/or silicon nitride (e.g., $SiN_x$, $Si_3N_4$). Such an encapsulation layer may also add to the inflexibility of the second regions or to protect the integrated circuits.

Figure 44:
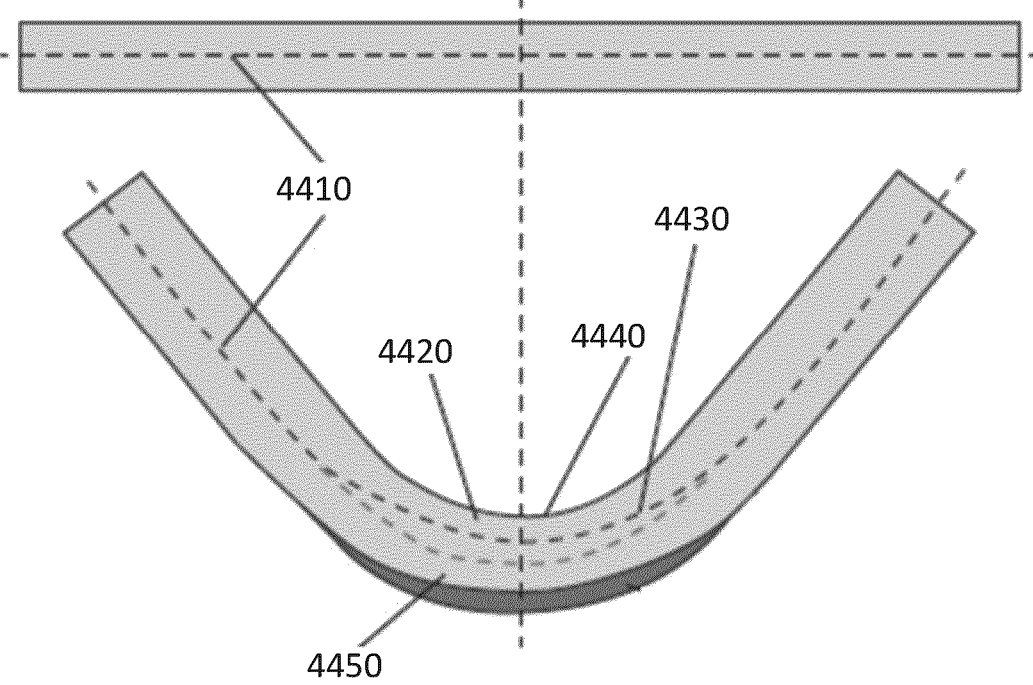
FIG. 44 schematically illustrates flexion in a material along with a bending radius of the neutral axis, according to some embodiments.

Flexibility can be measured by the achievable bending radius (without breaking the material). As an example, FIG. 44 schematically illustrates a neutral material and a flexed material. As shown in the figure, the neutral material has a neutral axis 4410, and, upon bending the material, the neutral axis 4410 is also bent, shown by flexion 4420. In the flexed state, a radius of neutral axis 4430 forms relative to neutral axis 4410. Flexing also causes the formation of an inside radius 4440 and outside radius 4450.

In some embodiments, the flexible circuit board (or a component of the flexible circuit, such as a first region, a polymer layer, an interconnect) may have a particular bending radius without cracking or otherwise damaging the circuit board or its components. In some embodiments, the flexible circuit board has a bending radius in the flexible regions of greater than or equal to 1 micron, greater than or equal to 3 microns, greater than or equal to 5 microns, greater than or equal to 7 microns, greater than or equal to 10 microns, greater than or equal to 12 microns, greater than or equal to 15 microns, greater than or equal to 18 microns, greater than or equal to 20 microns, greater than or equal to 25 microns, greater than or equal to 30 microns, greater than or equal to 40 microns, or greater than or equal to 50 microns. In some embodiments, the flexible circuit board has a bending radius of less than or equal to 50 microns, less than or equal to 40 microns, less than or equal to 30 microns, less than or equal to 25 microns, less than or equal to 20 microns, less than or equal to 18 microns, less than or equal to 15 microns, less than or equal to 12 microns, less than or equal to 10 microns, less than or equal to 7 microns, less than or equal to 5 microns, less than or equal to 3 microns, or less than or equal to 1 micron. Combinations of the above-referenced ranges are also possible (e.g., greater than or equal to 10 microns and less than or equal to 25 microns). Other ranges are possible.

A flexible region of a flexible circuit board may have a flexibility within any of the specified ranges, such as by being sufficiently flexible to have a specified bending radius while maintaining functionality during or following bending/wrapping/folding at that radius. An inflexible region may be one that, similarly, has a bending radius below a desired bend radius threshold or within a desired radius range. The bending radius of an inflexible region may thus be lower than a bending radius of a flexible region, and a flexibility of an inflexible region may be lower than a bending radius of a flexible region.

Flexibility may be measured using a variety of techniques. As one example, a rod having a radius corresponding to a desired wrap radius/diameter may be provided, and a substrate (e.g., the flexible circuit board) may be wrapped several times around the rod and then tested for functionality to evaluate whether the substrate is able to withstand bending at that radius. If so, the substrate is flexible enough to achieve the desired flexibility at the desired wrap radius/diameter. For small wrap diameters/radiuses, such a rod technique may be difficult or impractical. In such a case, the substrate may be folded and then pressure may be applied to achieve a desired thickness of the folded substrate stack. The folded substrate may then be tested for functionality to determine whether it withstood folding/wrapping at that thickness. Testing several times in succession may allow for determining a maximum folding/bending/wrapping radius the substrate is able to withstand. The bending radius may be calculated by dividing a thickness of the folded substrate stack at thickness and then dividing that thickness by the number of layers/folds. The testing for functionality during rod wrapping or folding may include monitoring electrical parameters such as resistance during the test, to determine whether there is a change that may indicate damage to or breaking of a component (e.g., an interconnect).

As mentioned elsewhere herein, the first region (e.g., the flexible region) of the circuit board can be wrapped around at least a portion of the second region (e.g., the inflexible region) and may also be wrapped within and/or around one or more components of the invasive probe. For example, as schematically illustrated in cross section in FIG. 41C, invasive probe 4140 shows first region 4110 wrapped around second region 4120. As shown in the figure, the flexible circuit (e.g., first regions of the flexible circuit) starts within the housing 4150 adjacent to the core 4160 and then is wrapped around a part of the housing 4150 that includes elongated core 4160, and disposed within the jacket 4170 of the invasive probe. As shown in the examples of FIGS. 41A-41B, the flexible circuit board 4100 of FIG. 41C includes a flexible first region that starts adjacent to the elongated core 4160 and then wraps around the housing 4150 until the second region 4120 of the second integrated circuit 4126 is disposed at a location in the housing 4150 where it can be seated flat in an area protected from flexing forces (see, e.g., the opening in the housing illustrated in FIG. 35). Another flexible region 4110 then continues wrapping around the housing 4150 until another inflexible region 4120 that positions the first integrated circuit 4124 at the location in the housing 4150 where it can be seated flat and protected from flexing forces and is aligned with the second integrated circuit 4124. Another flexible region 4110 then follows and wraps around the housing and the circuits 4124, 4126, as shown. This last flexible region 4110 may include one or more electrodes of sensors, as is shown in the example of FIG. 36A, such that the electrodes may be positioned on an exterior of the invasive probe and contact one or more tissues of a duct of an animal. In some embodiments at least one of the flexible regions (e.g., this last region) is configured to form one or more complete turns around a portion of the flexible circuit, a portion of an invasive probe (e.g., a guidewire).

The flexible circuit board and the integrated circuits may be adapted and arranged such that, when the flexible circuit board is in the wrapped configuration, the second regions (e.g., two or more integrated circuits of the second regions) are aligned within the invasive probe. Aligned may mean that the two circuits are disposed with one atop the other, as shown. For example, in FIG. 41C, the first integrated circuit 4124 and the second integrated circuit 4126 are aligned.

The first circuit 4124 may in some embodiments include one or more active electronics components and may be operatively associated with one or more sensors (not shown) to sense one or more values of the tissue(s) of the duct of the animal contacted by the sensor(s). This may include one or more components to generate and apply one or more electrical signals of one or more frequencies and one or more components to determine an impedance of the tissue(s) based on an analysis of the electrical signals received from the tissue(s) in response to the applying. The first circuit 4124 may include components and functionality discussed elsewhere herein of a measurement unit (e.g., measurement unit 214 of FIG. 2. As discussed above, positioning the first circuit 4124 on the flexible circuit 4100 close to the sensor(s)/electrodes (e.g., closer than the second circuit 4126, as shown-see, e.g., the illustration of FIG. 36A) may allow for reducing noise in signals received by the first circuit 4124. The second circuit 4126 may include passive components that are driven by the active components of the first circuit 4126. For example, the second circuit 4126 may be configured to process (e.g., impedance filter) the one or more values received by the first integrated circuit 4124. In such an embodiment, this can allow sensing and processing to be separated while still being a part of one flexible circuit board.

Figure 41C:
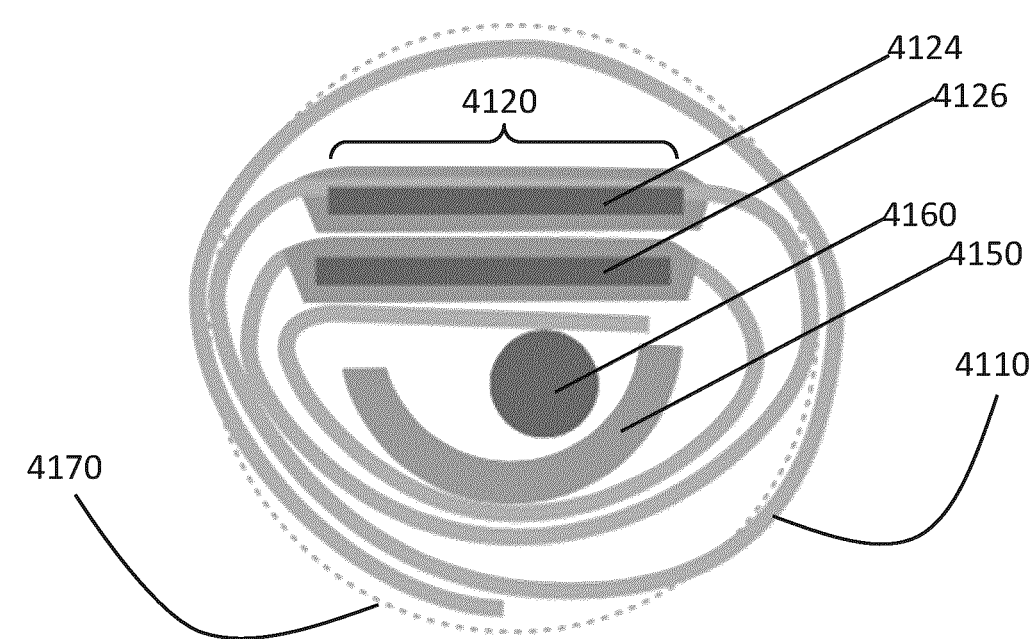
FIG. 41C shows a schematic cross-sectional view of a distal portion of a guidewire with a flexible circuit board wrapped around a housing, according to some embodiments.

While FIG. 41C shows two integrated circuits, it will be understood that the flexible circuit board may comprise more than two circuits, as this disclosure is not so limited. Those of ordinary skill in the art, based on the teachings of the present disclosure, will be capable of selecting an appropriate number of integrated circuits for the flexible circuit board while maintaining the desired flexibility and functionality.

FIG. 42 shows a flowchart for positioning and aligning a flexible circuit within a housing (e.g., an inflexible housing) of an invasive probe. In some embodiments, method 4200 starts by positioning the flexible circuit board into a slot of the housing, shown in block 4205. The slot of the housing may be sized and shaped to contain a portion of the flexible circuit board, which may be a flexible portion. The flexible portion the is arranged in the slot may be, in some embodiments, a portion that starts within the inflexible housing and extends away from the inflexible housing to an outside of the housing, such as a portion that includes one or more conductive contacts to which one or more wires are to be connected. In some embodiments, when the flexible circuit is initially disposed in the slot in the housing in this block 4205, a binding material is applied to the housing and flexible circuit to secure/bind this initial part of the flexible circuit to this inner part of the housing. The binding material may be, in some embodiments, an adhesive (e.g., glue). The adhesive may be, for example, an insulating glue such as an epoxy (which may have advantageous adherence properties for metal and polyimide and may advantageously be able to withstand high temperature), cyano adhesives (e.g., cyano-acrylate), or silicone adhesives. Referring back to the cross section of FIG. 41C, the centermost portion of the flexible circuit 4100 that is shown adjacent to the elongated core 4160 may be bound to the elongated core 4160 and/or to the housing 4150 using the binding material.

In some embodiments, the flexible circuit board is configured such that the flexible circuit board in total, and/or one or more flexible regions of the circuit board, wrap completely around the inflexible housing. In some embodiments, during the wrapping a consistent or uniform tension is applied to at least a portion of the flexible circuit board, shown in block 4210, so that the inflexible portion stays within the slot and that a uniform or desired wrapping can be achieved. In addition, in some embodiments, the integrated circuits of the flexible circuit board (e.g., circuits 4124, 4126 of FIGS. 41A-41C) are arranged on the flexible circuit board such that when the circuit board is wrapped, the integrated circuits are aligned. Applying a consistent or uniform tension to the flexible circuit board during wrapping may ensure that the wrapping is done with a desired tautness such that a desired positioning of the circuits and other components of the flexible circuit board relative to the housing and/or to the other components of the flexible circuit board is achieved.

This consistent or uniform tension may be achieved in various ways, including in some embodiments by securing a fixed weight to the flexible circuit board during wrapping.

Next, a first, flexible region of the flexible circuit board is wrapped, shown in block 4215, to begin the wrapping process. Embodiments are not limited to specific techniques for achieving the wrapping. In some embodiments, the wrapping may be achieved by moving the flexible circuit around the housing while keeping the housing in place. In other embodiments, the wrapping may be achieved by rotating the housing with the flexible circuit extending away from the housing, such that the flexible circuit starts to wrap around the housing as the housing rotates. The flexible region can be wrapped around a portion of the inflexible region and/or the housing. The inflexible regions can then be aligned, shown in block 4420, and the second flexible regions can continue to be wrapped around the flexible circuit (or other components), as shown in block 4225.

In some embodiments, following the wrapping, an insulating material may be applied to the assembly of the wrapped flexible circuit and housing. The insulating material may be, for example, an insulating glue.

The process 4200 of FIG. 42 was described without specific reference to what is performing the process. As should be appreciated from the foregoing, the process 4200 is a manufacturing process that may be performed by a suitable manufacturing entity. In some cases, some or all of the steps may be performed by human workers assembling an invasive probe or component thereof. In other cases, some or all of the steps may be performed by one or more machines arranged to perform the step(s). Embodiments are not limited in this respect.

In some embodiments, while the flexible circuit board may be contained within a housing, at least a portion of the flexible circuit may extend outside the housing. For example, FIG. 43A schematically illustrates flexible circuit board 4100 wrapped around housing 4150. Region 4305 of flexible circuit board 4100 is connected to the region that was initially disposed in the slot (e.g., at block 4205 of FIG.

42) and bound to the housing. The region 4305 extends outside of the housing and contains one or more conductive contacts, such as first contact 4310 and second contact 4312. One or more wires of the invasive probe are to be connected to these conductive contacts to provide power and/or communication to the circuits of the flexible circuit board (e.g., circuits 4124, 4126).

As discussed above, outside of the inflexible housing, flexing forces will be applied to the components of the invasive probe during navigation through anatomy of an animal. To protect the connection between the wires and the conductive contacts, the connections could be made within the housing where no or less flexing forces would be applied to the connections. However, arranging the connections within the housing would limit the space available for components within the housing (circuits, wires, etc.), which could limit functionality. By positioning the one or more conductive conducts outside of the housing, more space is advantageously provided for the circuit board within the housing, including space for the inflexible portions of the flexible circuit board. By using the techniques described below to affix the wires to the region 4305 and achieve the electrical connections, reliability of the connections may be improved while preserving flexibility of the invasive probe in the area of the region 4305.

Each contact of the one or more conductive contacts can be attached to a wire that extend towards the proximal portion of a guidewire. For example, in FIG. 43A, ribbon 4315 contains one or more wires that are physically joined at their insulating jackets to form a ribbon and that extend toward a proximal region of the invasive probe. Each one wire may be electrically connected to only one contact of the conductive contacts. For example, first wire 4320 of ribbon 4315 is electrically connected to contact 4310, and a second wire of the ribbon (not shown) is electrically connected to second contact 4312, and so on. Though, as should be appreciated from FIG. 43A, each of the wires of the ribbon 4315 contacts all of the conductive contacts at least via the insulating jacket of the wire of the wire in the ribbon 4315. More particularly, the ribbon 4315 overlays the conductive contacts in the example of FIG. 43A, but each wire of the ribbon 4315 is electrically connected to only one conductive contact and each conductive contact is electrically connected to only one wire of the ribbon 4315.

FIG. 43B shows a cross sectional side perspective of the connections described above. For example, first wire 4320 connects to first contact 4310 through aperture 4330. Wire insulation 4322 of first wire 4320 insulates first wire 4320 from other wires of the ribbon and from the conductive contacts to which the first wire 4320 is not to be connected. For example, as shown in FIG. 43B, there is no aperture in the jacket 4322 in the area of the conductive contact 4312 and, as such, the wire 4320 is electrically insulated from the conductive contact 4312 and not electrically connected to the contact 4312. The same would be true of the other contacts of the region 4305 (see FIG. 43A illustrating five contacts in that example). As a result of the aperture 4330, the first wire 4320 is connected only to the first contact 4310. Similarly, it should be appreciated that the aperture 4430 is in the insulating jacket 4322 of the first wire 4320 only and at the location of the first contact 4310 there is no corresponding aperture in the insulating jackets of the other wires of the ribbon (the other wires are not shown in the cross-section of FIG. 43B). This ensures the first wire 4320 is in electrical contact with only first contact 4310 of the conductive contacts and that the first contact 4310 is in electrical contact with only the first wire 4320.

However, the other wires of the ribbon 4315 would include corresponding apertures at the locations of the conductive contacts to which those wires are to be connected. For example, in the area of contact 4312 (to which the first wire 4320 is not connected and thus there is no aperture in FIG. 43B), there would be an aperture in the insulating jacket of another wire of the ribbon 4315.

The aperture 4430 is an opening in the insulation 4322. The opening of the aperture 4430 may be formed by, for example, a laser ablation or other process for forming an opening in the insulating jacket 4322.

In some embodiments, a conductive binding material (not shown in FIG. 43B) is disposed in and around the aperture 4330 and provides electrical contact of the first wire 4320 to the first contact 4310. The conductive binding material may be, for example, a conductive glue such as a silver filled epoxy (where percolation of conductive micro balls within the epoxy provides conductivity), carbon filled glues (e.g., epoxies, silicones, on cyano (e.g., cyanoacrylate)), or solder. The conductive binding material enables binding the first wire 4320 and the ribbon 4315 to the first contact 4310 and the region 4130 and to ensure a good electrical connection between the first wire 4320 and the contact 4310.

In some embodiments, the conductive binding material disposed in an area of each of the conductive contacts (see FIG. 43A) to electrically each of the wires to a respective one of the conductive contacts is disposed across each of the wires of the ribbon 4315, including the wires that are not to electrically connect to a particular conductive contact. As should be appreciated from the foregoing, at the location of each of the conductive contacts, an aperture is formed in only one insulating jacket of one wire of the ribbon. Accordingly, despite the presence of the conductive binding material in that area, as a result of the insulating jackets only one wire of the ribbon is connected to each conductive contact. Applying the conductive binding material to all wires may therefore be superfluous from an electrical perspective. However, the presence of the conductive binding material serves another purpose here. As discussed above, the region 4305 of the flexible circuit will be subjected to flexing forces during navigation of anatomy of an animal and these flexing forces could degrade or break the connections of the wires to the conductive contacts. In the example embodiment of FIG. 43B, the conductive binding material may help protect and secure the connections by binding the whole width of the ribbon to the whole width of the region 4305. The conductive binding material, once it hardens, forms an area of decreased flexibility in the flexible region 4305. That decreased flexibility protects the electrical connection of the wires to the conductive contacts during flexing. The overall region 4305 maintains desired flexibility in this embodiment, though, because the conductive binding material is applied only in the areas of the respective conductive contacts and the regions of conductive binding material are separated by regions where there is no conductive binding material. Those regions without conductive binding material preserve their flexibility, enabling the overall region 4305 to have a desired flexibility for navigating anatomy of an animal while also protecting the electrical connections.

In some embodiments, the entirety of the region 4305 (or at least the areas of the conductive binding material and the conductive contacts) is covered in an insulating material like epoxy or an adhesive like silicone or cyano (e.g., cyanoacrylate), or a spray coating of polymer or a conformal coating of epoxy, parylene, polyimide, or other insulating material.

While FIGS. 43A-43B show two wires within the ribbon, it should be understood that the ribbon may contain additional wires (e.g., a third wire, a fourth wire, a fifth wire) and may provide electrical communication to proximal portions of the guidewire by additional conductive contacts (e.g., a third contact, a fourth contact, a fifth contact) of the flexible circuit board. Each of the one or more wires may be in electrical contact to each of the one or more conductive contacts through each of one or more apertures made in the insulation of the one or more wires.

FIG. 37 shows an alternative implementation of the guidewire assembly, in accordance with some embodiments. In this example, the body of the wire that would make up the proximal 150-160 cm of the guidewire in-between the proximal connector assembly 20 and the multifilar coil comprises a metal torque tube 32. This metal tube would be made of stainless steel or nitinol, and have an outer coating such as PTFE (TEFLON). A distal core wire 31 and a proximal core wire 34 may be soldered or bonded 35 to the torque tube 32, such that the transition to the multifilar coil 2 and distal grind of the core wire 31 can be accomplished, and the connector assembly 20 may then be constructed in much the same way as the wire assembly shown in FIG. 31. Since the wire leads 4 in some embodiments transition out of the multifilar coil, then into the torque tube through the distal solder joint and then back out of the torque tube at the proximal end, in some such embodiments plastic jackets 33 may cover the wire leads 4.

The main benefit of using a metal torque tube is that the wires can be housed inside and thus more protected. Further, a torque tube may better be able to transmit torque since the outer diameter of the torque tube will be greater than the largest diameter of the core wire 1 used in the guidewire assembly in FIG. 31. For instance, a stainless steel torque tube can be 0.013" (0.33 mm) vs. 0.011-0.012" (0.28 mm-0.30 mm) of a full length core wire. One drawback of using a torque tube is that it is more easily kinked than a full length stainless steel core wire.

Figure 38:
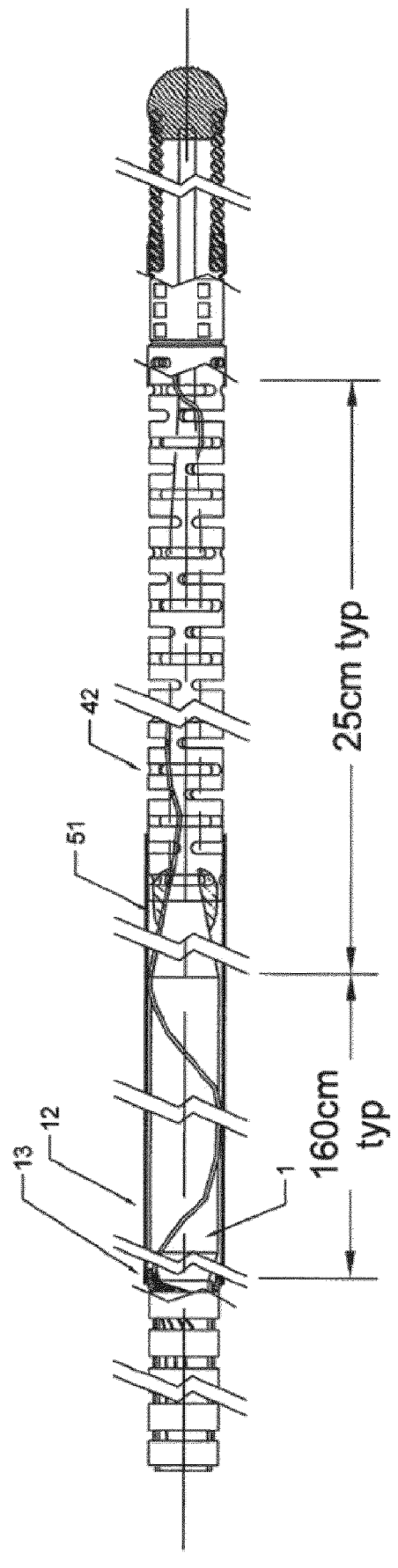
FIG. 38 is a schematic diagram illustrating yet another example of a guidewire which may be implemented in some embodiments.
Figure 39:
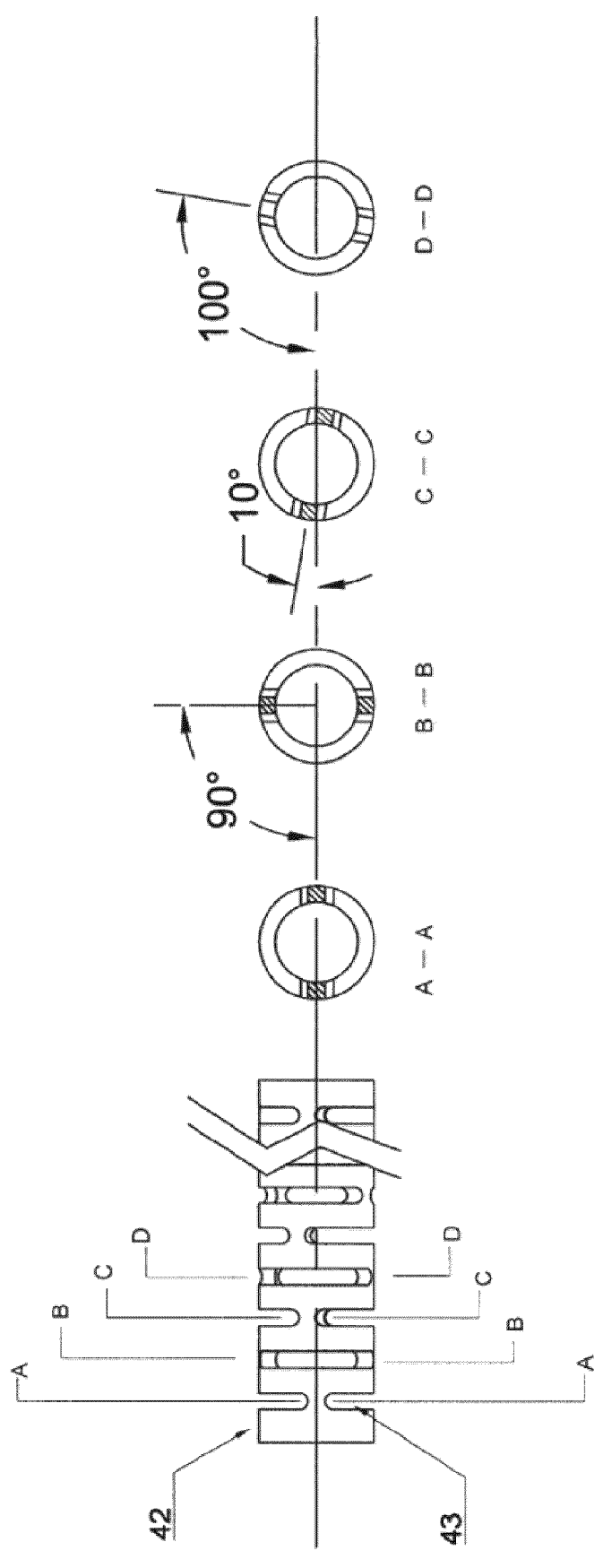
FIG. 39 illustrates a portion of the guidewire of FIG. 38 in additional detail and a plurality of cross sections, in accordance with some embodiments.

FIG. 38 shows another example of a guidewire assembly. In this example, the multifilar coil used in the guidewire assembly shown in FIG. 31 is replaced with a highly flexible torque tube 42 made of nitinol tube or other materials with a multitude of slots cut in a sequential manner. Guidewires using torque tubes similar to this are commercially available, such as the Synchro™ Guidewire marketed by Stryker Corporation. FIG. 39 shows an exemplary version of a flexible torque tube. This torque tube for example, would be made from 0.014" (0.36 mm) OD nitinol tubing with a wall thickness of approximately 0.002"-0.003" (0.05 mm-0.08 mm). Sequential slots 43 would be made using a laser, an abrasive cutting wheel, a wire EDM machine or the like. This version shows slots 43 made where each slot is approximately 0.006" (0.15 mm) deep and 0.002" (0.05 mm) wide, and the centerline of each slot 43 is 0.005" (0.13 mm) separate from the next. The slots may be cut in a progressing angular sequence, such that the first slot and the slot diametrically opposed are cut at 0 degrees, then using the first slot angle as baseline, the next set may be at 90 degrees, the next set may be at 10 degrees, the next set may be at 100 degrees, the next set may be at 20 degrees, the next at 110 degrees and so on. These angles and progression are shown in sections A-A through D-D.

The benefit of this type of torque tube is that it can transmit torque in true one-to-one manner around very tight curves, much like a driveshaft coupler or universal joint. The drawback of this type of torque tube is that they are expensive to manufacture.

FIG. 40 shows another example of a guidewire assembly. This example is similar to the assembly show in FIG. 31. The main difference is that the very distal end of the stainless steel core wire 1 is shortened, and coupled to a nitinol wire 60 using a tube coupler 61 and either laser welds, solder, glue or the like to complete the joint. A nitinol wire 60 of a diameter of 0.005"-0.007" (0.13 mm-0.18 mm) in diameter has the benefit of being very flexible and almost un-kinkable even in the tightest curve.

These examples are exemplary of some embodiments of the invention but it is understood that many combinations of the mechanical features detailed in these versions can be combined to create more versions, that would still be encompassed in the spirit of embodiments of the invention.

Examples of Sensors and Sensing Techniques

As discussed above, in some embodiments a measurement unit of an invasive probe may operate sensors of the invasive probe to perform an Electrical Impedance Spectroscopy (EIS). FIGS. 4-11 describe examples of ways in which such sensors and measurement units may be arranged, and describe examples of techniques for operation of such sensors and measurement units. It should be appreciated, however, that embodiments are not limited to operating in accordance with the examples for EIS described in this section.

The techniques described in this section with regard to FIGS. 4-11 allow for a discrimination of tissues and/or biological materials of a lesion of a duct of an animal, including of a mammal such as a human. "Discrimination" should be understood here to mean the possibility, given by this method, of distinguishing between lesions of different compositions, for example by determining one or more types of cells (e.g., red blood cells and/or white blood cells, or different types or states of endothelial cells) of the lesion and/or one or more types of other biological material (e.g., plaque materials such as cholesterol) of the lesion. More generally, the discrimination made possible by techniques described in this section includes determining at least one item of information relating to a tested lesion. Examples of information that may be determined through these techniques are given later.

Figure 4:
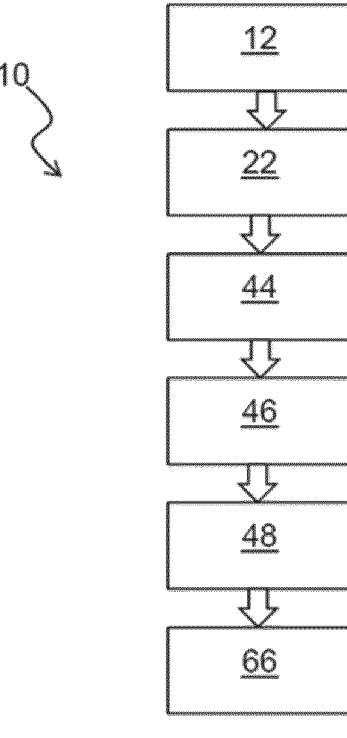
FIGS. 4-5 are flowcharts of processes that may be implemented in some embodiments to determine a composition of a lesion.

The cell discrimination method 10, as illustrated schematically in FIG. 4, comprises a first step 12 of determining a frequency spectrum of the impedance of a lesion that is tested.

Spectrum should be understood here to mean a set of pairs of values of the impedance of the lesion, the latter being able to be complex, and of a corresponding frequency. This spectrum may thus be discrete and comprise only a finite number of pairs. These pairs may notably be separated by several Hz, even by several tens of Hz, even by several hundreds of Hz. However, in other embodiments, the spectrum determined in this step is continuous, pseudo-continuous or discretized, over a frequency band. Pseudo-continuous should be understood to mean that the spectrum is determined for successive frequencies separated by 100 Hz or less, preferably by 10 Hz or less, preferably even by 1 Hz or less. The frequency band over which the impedance of the tissue is determined extends, for example, from 10 kHz, preferably 100 kHz. In effect, at low frequencies, the membrane of the tissue/material of the lesion acts as an electrical insulator, so that the impedance is very high and, above all, varies little. Moreover, the frequency band over which the impedance of the tissue/material is determined extends, for example, up to 100 MHZ, preferably 1 MHZ. In effect, at high frequencies, the wall of the tissue/material that make up the lesion become transparent from an electrical point of view. The measured impedance is therefore no longer representative of the biological structure. This spectrum may be a frequency spectrum of the real part and/or of the imaginary part and/or of the modulus and/or of the phase of the complex impedance of the lesion.

Figure 5:
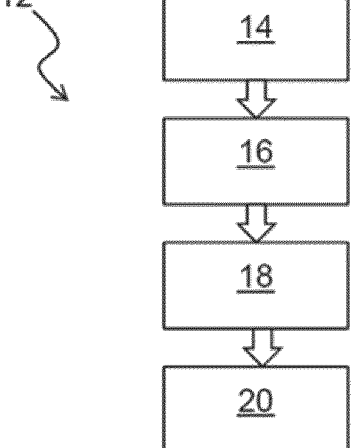

This first step 12 of determination of a frequency spectrum of the impedance of the lesion may notably be performed as described hereinbelow in connection with FIG. 5.

First of all, during a step 14, two, preferably three, even more preferably four electrodes are placed in contact with the lesion to be tested, the electrodes being linked to an alternating current generator. The measurement with four electrodes is preferred because it makes it possible to implement two electrodes to pass the current into the lesion to be tested and to measure the potential difference between the other two electrodes. This makes it possible to improve the accuracy of the measurement. Then, during a step 16, an alternating current is applied between the electrodes contacting the lesion. Then, by varying the frequency of the current applied during a step 18, the corresponding voltage is measured, at the terminals of the electrodes for different frequencies. Finally, during a step 20, the ratio between the voltage measured and the current applied is calculated, for each of the frequencies for which the measurement has been performed. This ratio gives the impedance of the lesion tested, as a function of the measurement frequency. The calculated ratios make it possible to define a frequency spectrum of the impedance of the lesion.

Figures 6, 7:
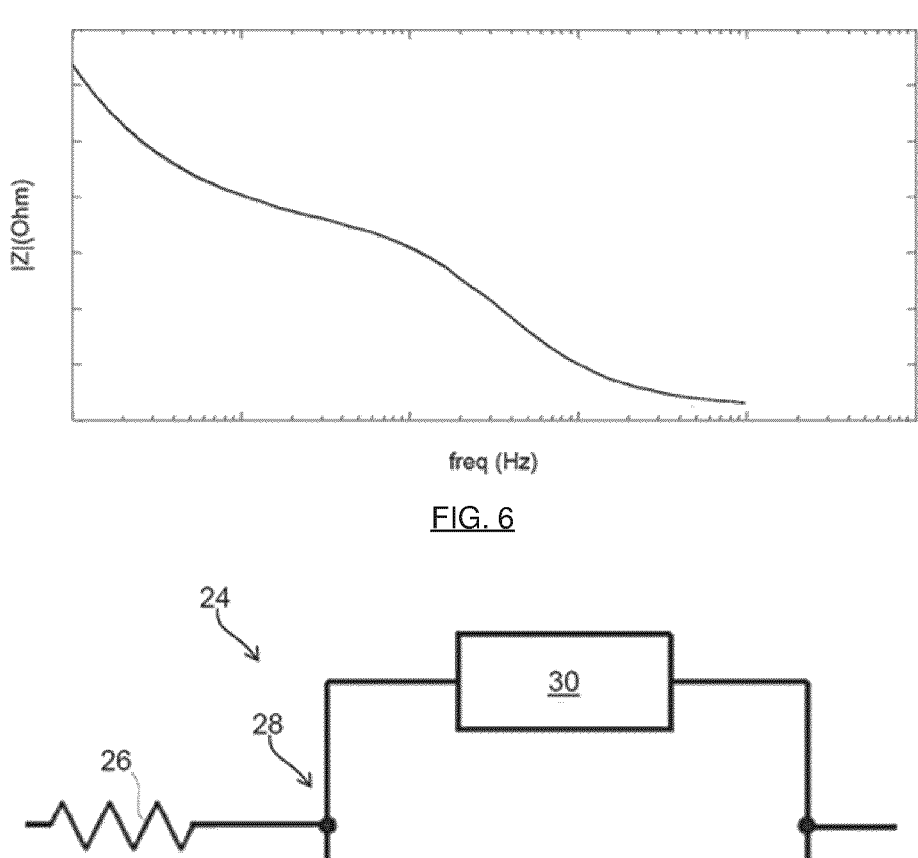
FIG. 6 is a representation of an exemplary frequency spectrum of the modulus of the impedance of a lesion.
FIGS. 7-10 illustrate exemplary models of the impedance of a lesion, that may be implemented in the method of FIG. 4, including a constant phase element.

When the spectrum is continuous or pseudo-continuous, it may be represented as illustrated in FIG. 6, in the form of a curve giving, in this particular case, the modulus of the impedance of the lesion as a function of the frequency, the latter being plotted according to a logarithm scale. It should be noted here that a logarithmic scale is used on the x axis.

In a step 22 of the discrimination method 10 of FIG. 4, different models of the impedance of the lesion, that is to say different electrical circuits that may model the lesion, are then chosen. Here, models are chosen that include a constant phase element, and not a capacitance. In effect, it has been found that a constant phase element models more realistically the behaviour of the lesion than a capacitance.

A constant phase element (or CPE) has an impedance $Z_{CPE}$ of the form:

$$Z_{CPE} = \frac{1}{(j\omega)^\alpha Q_0} \qquad [1]$$

or $$Z_{CPE} = \frac{1}{(j\omega Q_0)^\alpha} \qquad [2]$$

in which:

j is the square root of −1 ($j^2$=−1);

$\omega$ is the specific pulsing of the current ($\omega$=2πf, in which f is the frequency of the current);

$Q_0$ is a real parameter of the constant phase element; and $\alpha$ is another real parameter of the constant phase element, lying between 0 and 1, such that the phase $\varphi_{CPE}$ of the constant phase element is equal to −απ/2.

Hereinafter in the description, a constant phase element whose impedance is given by the equation [1a] or [1b] above is chosen by way of example.

The models of the impedance of the lesion may notably be chosen from those described hereinbelow, with respect to FIGS. 7-10. Obviously, the simpler the model, the simpler the calculations. However, a complex model may better correlate to the spectrum of the impedance obtained by the measurement and therefore give more accurate results.

According to a first model 24 illustrated in FIG. 7, the impedance of the lesion is modelled by a first resistance 26 mounted in series with a parallel connection 28 of a constant phase element 30 and of a second resistance 32.

In this case, the total resistance $Z_{tot}$ of the lesion is of the form:

$$Z_{tot} = R_1 + \frac{R_2}{1 + (j\omega)^{\alpha} Q_0 R_2}, \qquad [3]$$

in which:

$Z_{tot}$ is the total impedance of the first model 24 representing the lesion;

R1 and R2 are the resistance values of the first 26 and second 32 resistances.

Such a model describes particularly well a tissue covering measurement electrodes, like a set of individual parallel mountings, each individual mounting being made up of an individual resistance in series with a parallel mounting of an individual resistance and of an individual capacitance. Such a mounting makes it possible to model a distribution of the time constant over all of the surface of the measurement electrodes, according to different circuits in parallel whose parameters may be different, each of these circuits in parallel representing different tissue/material of a lesion. Thus, the fact that the tissues/materials of the lesion may exhibit different electrical properties, notably a different resistance and/or capacitance, is modelled.

Figure 8A:
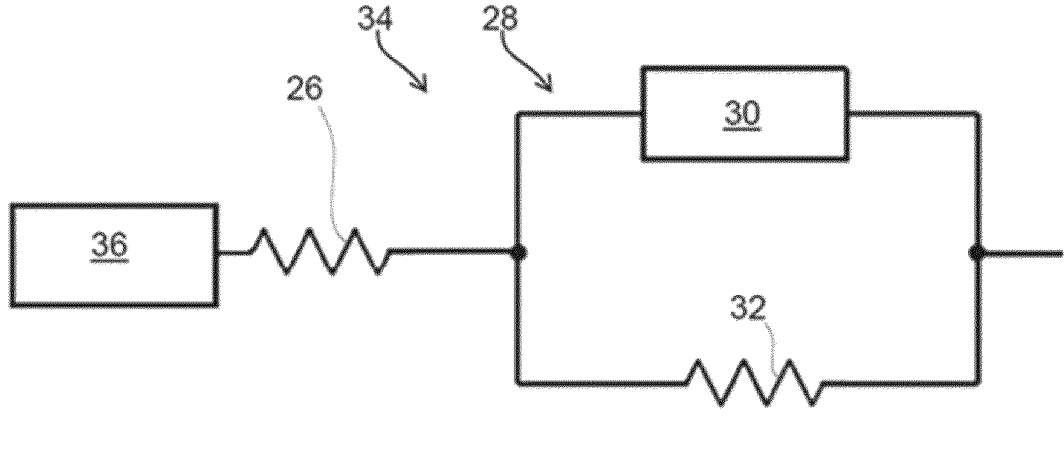

A second model 34, illustrated in FIG. 8A, complements the model 24 of FIG. 7, by the series mounting of a second constant phase element 36. The impedance $Z_{CPE,2}$ of this second constant phase element 36 may also be chosen to be of the form:

$$Z_{CPE,2} = \frac{1}{(j\omega)^{\beta} Q_1}, \qquad [4]$$

in which:

$\beta$ is a real parameter lying between 0 and 1, such that the constant phase of this second constant phase element is equal to $-\beta\pi/2$; and $Q_1$ is a real parameter of the constant phase element.

The total impedance $Z_{tot}$ of the lesion according to this second model 34 is therefore given by the following equation:

$$Z_{tot} = \frac{1}{(j\omega)^{\beta} Q_1} + R_1 + \frac{R_2}{1 + (j\omega Q_0)^{\alpha} R_2}. \qquad [5]$$

Figure 8B:
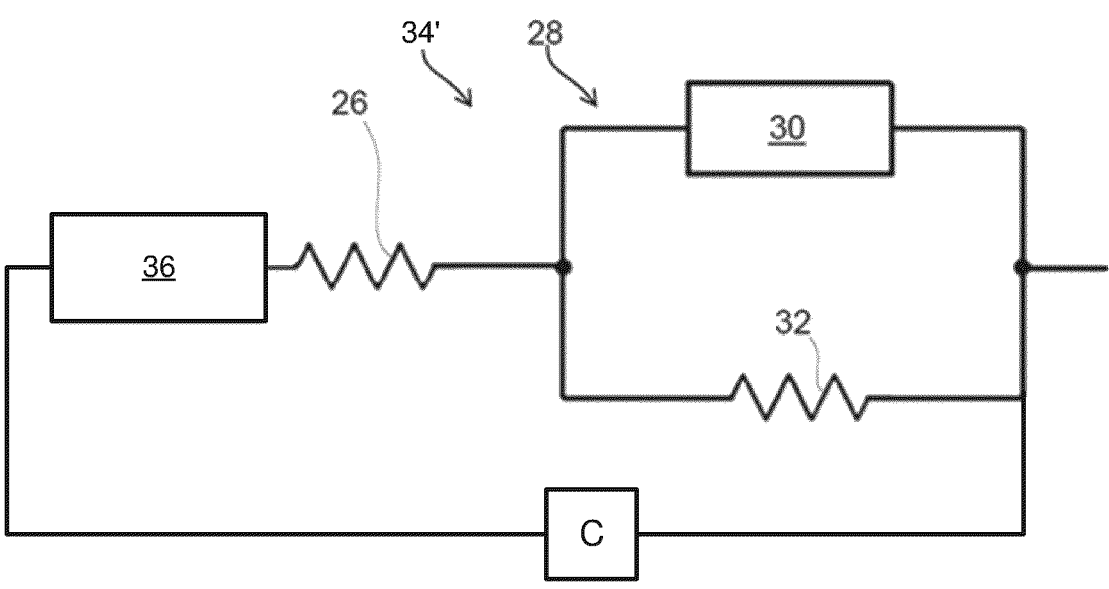

A variant 34′ of the second model 34 is shown in FIG. 8B, and differs from the model of FIG. 8A by the addition of a capacitance C in parallel with the circuit of FIG. 8A, for a better fit of the impedance curve at high frequencies.

Figure 9:
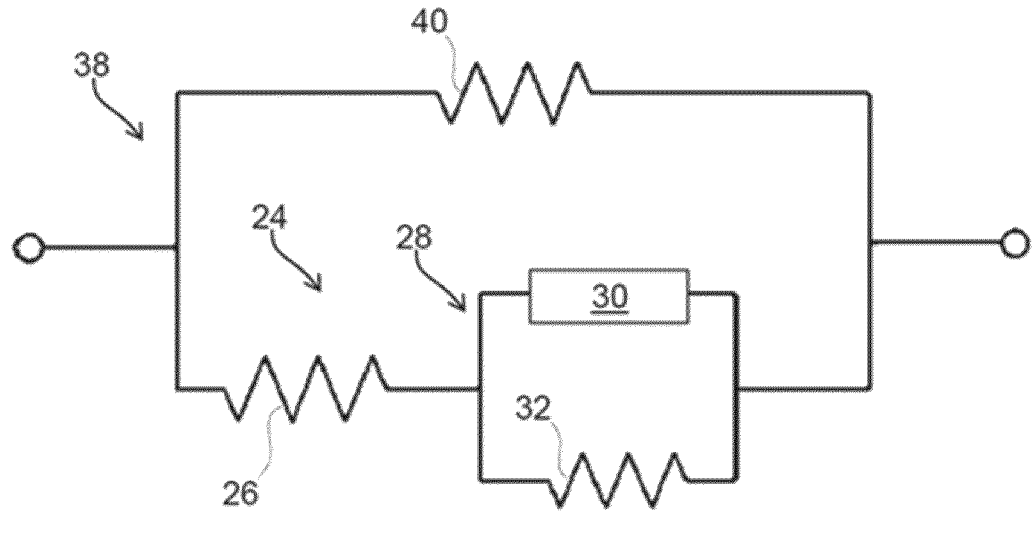

A third model 38, illustrated in FIG. 9, corresponds to the model of FIG. 7, mounted in parallel with a third resistance 40, of resistance $R_3$. In this case, the total impedance $Z_{tot}$ of the lesion is given by the equation:

$$\frac{1}{Z_{tot}} = \frac{1}{R_3} + \frac{1}{R_1 + \frac{R_2}{1 + (j\omega Q_0)^{\alpha} R_2}}. \qquad [6]$$

Figure 10:
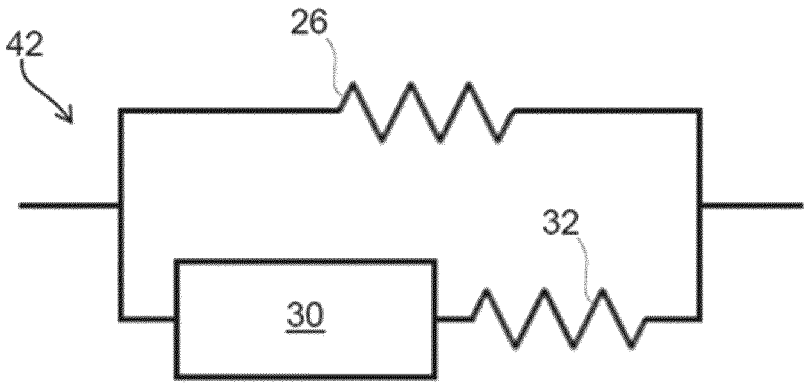

Finally, a fourth exemplary model 42 is illustrated in FIG. 10. This model 42 comprises, as illustrated, a first resistance 26, mounted in parallel with a series mounting of a constant phase element 30 and of a second resistance 32.

The total impedance $Z_{tot}$ of the lesion is given, for this model 42, by the equation:

$$\frac{1}{Z_{tot}} = \frac{1}{R_1} + \frac{R_2}{1 + (j\omega Q_0)^{\alpha} R_2} \qquad [7]$$

The discrimination method then continues with a step 44, during which, for each model chosen in step 22, the impedance of the constant phase element 30 that optimizes the correlation between the model of the impedance of the lesion and the spectrum determined in step 12 is determined.

This step of optimization of the correlation between the model of the impedance of the lesion and the spectrum determined in the step 12 may be implemented by any optimization method known by those skilled in the art. By way of example, the least squares method may be implemented, which allows for a practical and relatively simple implementation of this step 44.

In practice, the other parameters of the different models, other than those of the impedance of the constant phase element, are also determined during this step 44. These elements may also be useful for obtaining information on the lesion tested and/or on the tissues/materials of which it is composed.

An intermediate step 46 of the discrimination method 10 may then be provided. This step 46 consists in determining the model which seems to best correlate with the measured spectrum of the impedance of the lesion. This best model may for example be that which minimizes the standard deviation with the measured spectrum. Hereinafter in the description, the case in which the model 24 is retained as that correlating best to the measured spectrum of the impedance of the lesion is assumed.

During a step 48, an effective capacitance (or apparent capacitance) of the lesion is deduced from the parameters of the impedance of the constant phase element and from the corresponding model.

Theoretically, this effective capacitance is representative of a set of individual capacitances of elements of the cell structure. The effective capacitance is representative of distributed local capacitances of elements of the cell structure. These elements of the cell structure may notably be all or some of the nuclei of the cells of the cellular structure and also other parts of the cells such as the Golgi apparatus, vesicles, mitochondrion, lysosome and other elements which may play a role in membrane interaction. The effective capacitance may also be influenced by the geometry of cells and the space between cells. The effective capacitance is a model which allows for a representation of the electrical membrane behaviour of a part or of all of a lesion. This model makes it possible to relevantly discriminate the tissues/materials of the lesion More practically, this effective capacitance is determined by identifying the impedance of the lesion with a model comprising individual parallel mountings, each individual mounting comprising at least one individual resistance and one individual capacitance. Each mounting may notably comprise, preferably consist of, a first individual resistance in series with a parallel mounting of an individual capacitance with a second individual resistance. These individual mountings aim to model the behaviour of each tissue/ material of the lesion. The effective capacitance is then the capacitance resulting, in the lesion, from the presence of all the individual capacitances.

In the case of the model 24 (or 34 or 34'), the determination of the effective capacitance may notably be performed as follows. The impedance of the model 24 with a constant phase element is compared with the impedance of an equivalent or identical model, in which the constant phase element is replaced by an effective capacitance. The calculation, strictly speaking, of the effective capacitance may then be performed by comparing the real part and/or the imaginary part and/or the phase and/or the modulus of the impedance of the model chosen for the lesion with a constant phase element with the identical model in which the constant phase element is replaced by an effective capacitance.

In the case of the model 24 (or 34 or 34'), for example, by introducing a time constant $$\tau_0 = C_{\it eff} \frac{R_1 R_2}{R_1 + R_2}$$

into the equation of the admittance of the model 24, directly deduced from the equation [3], the equation [8] below is obtained:

$$Y_{tot} = \frac{1}{R_1}\left[1 - \frac{R_2}{R_1 + R_2}\left(1 + \frac{R_1 R_2}{R_1 + R_2}Q_0(j\omega)^\alpha\right)^{-1}\right] = \qquad [8]$$
$$\frac{1}{R_1}\left[1 - \frac{R_2}{R_1 + R_2}(1 + (j\omega\tau_0)^\alpha)^{-1}\right]$$

from which a formula for the effective capacitance may be deduced, in the form:

$$C_{\it eff} = Q_0^{1/\alpha} \times \left(\frac{1}{R_1} + \frac{1}{R_2}\right)^{(\alpha-1)/\alpha} \qquad [9]$$

In the case where another model of impedance of the lesion with a constant phase element is chosen, it is possible to determine a corresponding equation of the effective capacitance. To do this, it is sufficient to calculate the impedances $R_1$, $R_2$, $Z_{CPE}$ and $Z_{CPE,2}$, if appropriate, of the model 24 or 34 or 34', as a function of the parameters of the chosen model, for the model 24 or 34 or 34' to be electrically equivalent to the model of the impedance of the lesion. The effective capacitance may then be calculated by replacing $R_1$, $R_2$, $Z_0$ and α with the corresponding values, expressed as a function of the parameters of the chosen model.

The cell discrimination method 10 then continues with a step 66 of deduction of an item of information on the tissues/materials of the lesion, from the effective capacitance determined previously.

This deduction may notably be made by comparing the value of the effective capacitance determined in the step 48 with pre-established values. The pre-established values may notably be obtained during tests performed on tissues of known compositions, in known media, and with known test conditions. The pre-established values may be grouped together in a database of effective capacitance values, grouping together the effective capacitances measured for different types of cells and/or different conditions of different cells and/or in different test conditions. The effective capacitance value may be compared to a database of effective capacitances of cell type and condition susceptible to be found in the present measurement. For the comparison, the effective capacitance Ceff may be used together with other parameters. The comparison may not be an exact match and includes the determination whether the effective capacitance value falls or not within a pre-determined range.

It is thus possible to discriminate the tissues/materials of the lesion, that is to say to determine at least one of the following items of information:

the type of tissues and/or other biological materials in the lesion;

the composition of the lesion, notably if the latter is composed of different types of biological materials or of tissues/cells/other biological materials in different states;

when the lesion is composed of tissues, the types of cells included in the tissue and/or the number of layers of cells present in the tissue;

when the lesion is composed of other biological materials, such as plaque materials, the types of materials included in the lesion; and/or the state of the cells included in a lesion, notably if the cells are in a healthy state, in an inflamed state, in a degenerated state, notably if there are one or more cancerous cells, in an infected state.

Figure 18:
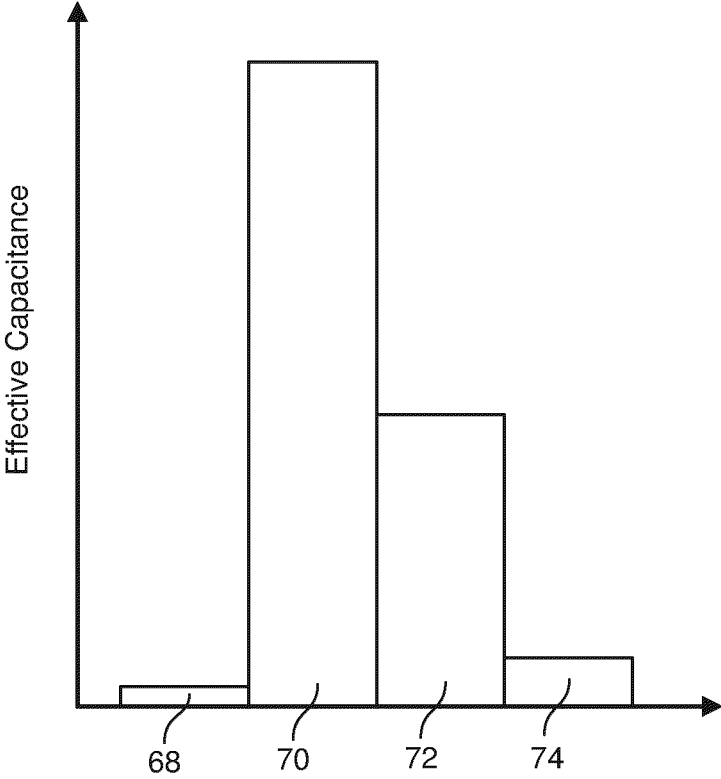
FIG. 18 shows an example, in diagram form, of effective capacitances of cellular structures determined by the method of FIG. 4.

As an example, FIG. 18 represents, in diagram form, the effective capacitances 68, 70, 72, 74 determined in the context of a test conducted according to the method described previously.

In the context of a test, cells were cultivated until the confluence of the cells was obtained. In the case of the exemplary test which was conducted, two days of culture were required in an incubator at 37° C. and 5% CO2, to obtain, by confluence, the tissues to be tested. The determination of the spectrum of the impedance of the different tissues to be tested was performed using an impedance spectroscopy system. The spectrum was determined between 1 kHz and 10 MHZ, by applying an alternating voltage estimated to be fairly low so as not to electrically excite the cells being studied, but sufficient to have correct measurements. In the example of the test conducted, an amplitude of 20 mV of the alternating voltage was retained.

The effective capacitance 68 is that of the test medium, static, alone. This test medium is a cell culture medium. The effective capacitance 70 is that of bovine aortic endothelial cells (BAEC). The effective capacitance 72 is that of bovine aortic smooth muscle cells (BAOSMC). Finally, the effective capacitance 74 is that of blood platelets (or thrombocytes). As this diagram shows, the effective capacitances of the different types of cells exhibit values clearly different from one another, which makes it possible to effectively distinguish between the different types of cells with accuracy, without risk of confusion.

Thus, one advantage of the discrimination method described above is that it allows for the discrimination of tissues/materials in a lesion contacting the electrodes, from a simple measurement of a frequency spectrum of an impedance of the lesion to be tested. The results obtained are accurate. There is no need to proceed with a normalization of the measured impedance, nor to proceed with a reference measurement in the absence of any sample to be tested. The method may thus be implemented without the need for prior sampling of cells or of a cellular structure to be tested, and may be implemented in vivo in some embodiments.

It should be noted, in the case where an effective capacitance is determined, that this single value for is often sufficient to discriminate the tissues/materials of the lesion. The parameters of the chosen model of the impedance of the lesion to be tested may also be compared to pre-established values to specify the result of the comparison of the effective capacitance. For example, when cells of a lesion are inflamed, the junction between the cells is more loose. The resistance at low frequency—that is to say the resistance 32 of the model 24 for example—is then lower, compared to healthy cells. A comparison of the value of this resistance with a value pre-established for healthy, non-inflamed cells may then make it possible to determine the inflamed state of these cells.

It should also be noted that the other parameters of the model may be considered to discriminate the tissues/materials of a lesion. However, these other parameters may also make it possible to determine additional items of information on the lesion tested. Thus, for example, R2 or the sum R1+R2 of the resistances 26, 32 of the model 24 may be considered to determine a thickness of a cellular structure, when a lesion includes tissues. To do this, the values R2, and possibly R1, are determined, notably concomitantly with the determination of the impedance of the constant phase element, so as to optimize the correlation of the model 24 with the measured impedance spectrum. The value R2 or the sum R1+R2 may then be compared to corresponding values, predetermined in known conditions, for example in vitro. These predetermined values may notably be stored in data store.

As stated previously, the method may easily be implemented in the context of devices that may be inserted into an animal subject, such as inserted into vasculature of a human subject.

Figure 11:
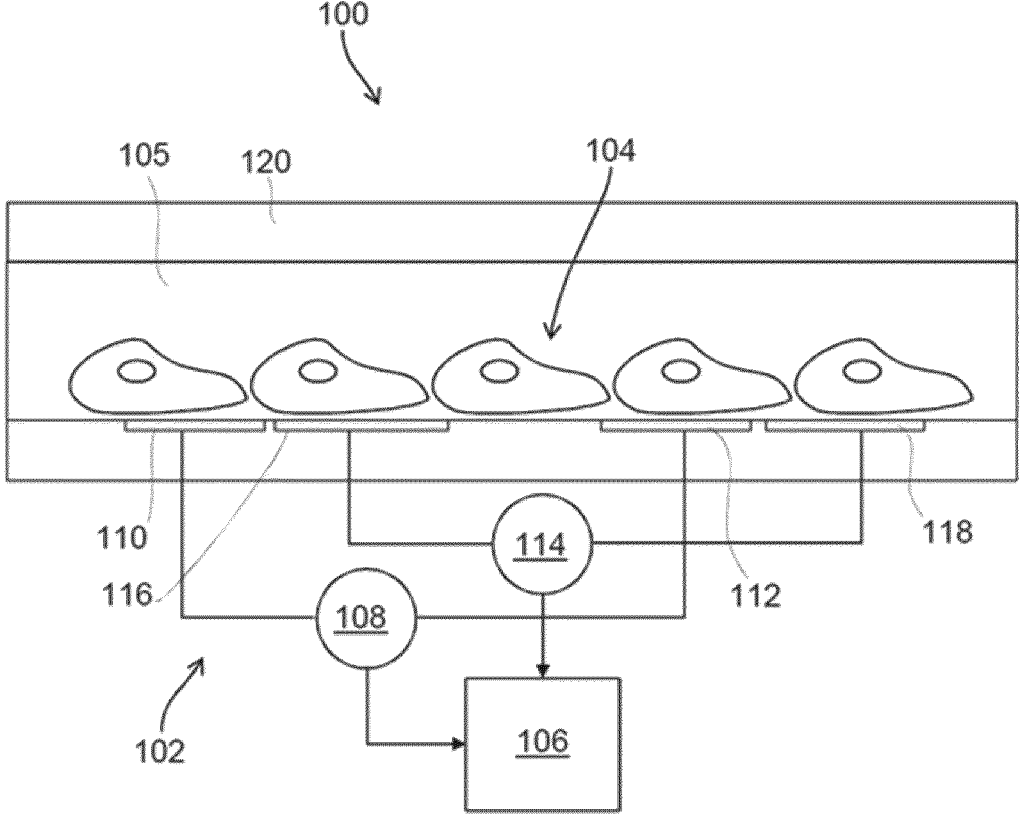
FIG. 11 illustrates an exemplary system for implementing the method of FIG. 4.

By way of example, FIG. 11 illustrates an example 100 of a system for implementing the method as described previously.

The system 100 essentially comprises means 102 for measuring the impedance of a lesion 104, here a single-layer tissue of confluent cells, dipped in a medium 105, for example blood, and an electronic control unit 106, linked to the measurement means 102, to implement the method and discriminate the tissues of the lesion 104 as a function of the measured impedance.

The measurement means 102 here comprise an electrical generator 108 of alternating current, linked to two electrodes 110, 112 in contact with the lesion 104. The measurement means 102 also comprise a device 114 for determining the intensity passing through the lesion 104, linked to said lesion 104 by two electrodes 116, 118 in contact with the lesion 104. The electronic control unit 106 is linked to the electrical generator 108 and to the intensity measurement device 114, in order to be able to determine the impedance of the lesion 104, for example from the measurement of the voltage and of the intensity at the terminals of the electrodes 110, 112, 116, 118.

The electrodes 110, 112, 116, 118 consist of an electrically conductive material, such as gold for example.

Here, advantageously, the measurement means 102 further comprise a medical device 120 that may be inserted in an animal subject, here an invasive probe. In this case, the electrodes 110, 112, 116, 118, the alternating voltage generator and the intensity measurement device may be fixed onto this medical device. The medical device is for example as described in the application FR3026631 A1 MEDICAL DEVICE PROVIDED WITH SENSORS HAVING VARIABLE IMPEDANCE filed on 2014 Oct. 3, the entire contents of which, and in particular the discussion of implantable medical devices including measurement devices, are incorporated herein by reference.

In this case, the alternating electrical generator 108 may include an armature, such as the body of the medical device or an antenna electrically insulated from the body of the medical device, adapted to emit an electrical current under the effect of an electromagnetic field emitted by an interrogation unit external to the stent 120. The electrodes may then form a sensor with variable impedance, the impedance of which varies as a function of the cellular structure which covers them. Finally, the electronic control unit may receive an item of information relating to the impedance between the electrodes, notably by emission of a magnetic field by an antenna fixed onto the body of the implantable medical device 120.

The stent 120 may thus make it possible to check the correct progress of the healing of the endothelium, after the stent 120 has been fitted. In effect, such a stent 120, in cooperation with the electronic control unit, makes it possible to determine, by implementing the method of FIG. 4, whether the cellular structure which is formed on the surface of the endothelium essentially comprises healthy endothelial cells, inflamed endothelial cells, smooth muscle cells and/or platelets.

The invention is not limited to the examples described hereinabove and numerous variants are possible, while within the scope of the definition given by the attached claims.

Thus, for example, it is possible to choose a single model of the impedance of the lesion in the step 22. In this case, it is not necessary to carry out the optimization for a number of models. The method is therefore simpler and faster to implement in this case. It is notably possible to proceed in this way when a model is considered as more relevant.

Moreover, in some examples described, the discrimination of the tissues/materials is based essentially on the calculated effective capacitance and on its comparison with pre-established values. As a variant, however, it is possible to proceed with the discrimination of the tissues/materials from parameters of the chosen model of the impedance of the lesion. However, it seems that the comparison of just the value of the effective capacitance is both simple and allows for a reliable discrimination of the cells.

Figure 19:
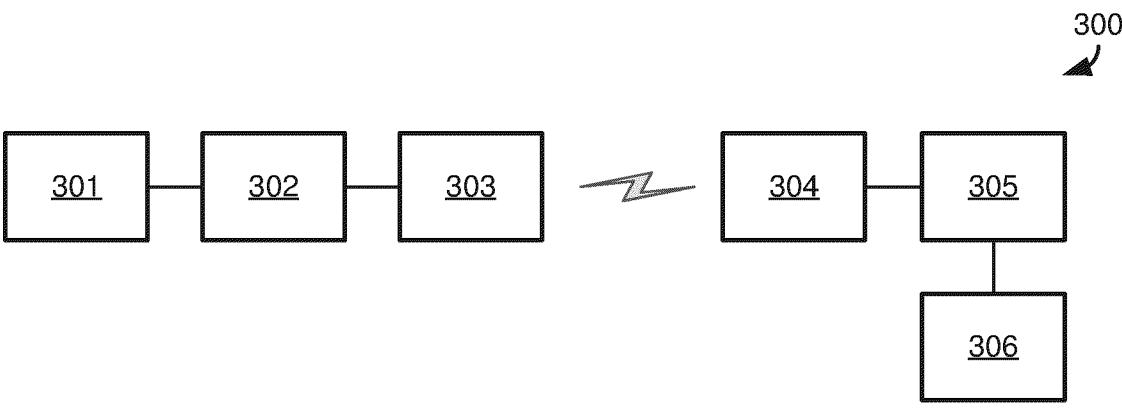
FIGS. 19 and 20 show examples of systems made in accordance with aspects of the present disclosure.

FIG. 19 shows an example of a system 300 made in accordance with aspects of the present disclosure. This system comprises a measurement module 301 with may be part of an implanted device, for example a stent, or of a device for in vitro cultivation of cells.

The measurement module comprises at least two electrodes and may be as described above with reference to FIG. 11.

The system 300 also comprises an internal processing unit 302 that is configured for example to generate an impedance spectrum from data from the measurement module.

The system 300 may comprise an emitter 303 to wirelessly transmit data (the data from the measurement module 301 and/or the impedance spectrum determined by the internal processing unit 302) to a receiver 304, which may be external to the body in case the measurements take place in vivo. The transmission may take place under any wireless protocol such as RFID, NFC, Bluetooth, WiFi, either radio or Infrared, inter alia. In some embodiments, the transmission may include transmission via one or more wired and/or wireless local and/or wide-area networks, including the Internet.

The system 300 may comprise an external processing unit 305 to compute the impedance spectrum (in the case of receiving from the emitter 303 the data from the measurement module 301) and/or the various parameters and effective capacitance Ceff based on the received data and display means 306 such as a LCD screen to display information relating to the type and/or condition of cells determined based upon comparison of a value representative of Ceff with reference data. To determine the various parameters and effective capacitance, the external processing unit 305 may be configured with information regarding one or more equivalent circuit models for an impedance, and determine the parameters of at least one of the model(s), such as in the manner discussed above. The external processing unit 305 may also be configured to select one of the models, following determination of the parameters of the model(s), as a model from which to determine the effective capacitance, as discussed above. The external processing unit may make the selection based on a degree of fit between the equivalent circuit model and the impedance spectrum. The system may provide, based on the at least one type and/or condition of cells thus identified, information representative of an evolution of a healing process, for example, information regarding a current status of an area in which (e.g., tissue to which) a procedure was performed (including positioning of an implant such as a stent) and/or provide information regarding a change over time in the status of the area that may be reflective of a response to the procedure in the area, such as a healing or scarring response.

The external processing unit may be a special-purpose device that includes specialized hardware such as an ASIC, EEPROM, or other component specially configured to perform the operations of the external processing unit described above. In other embodiments, the external processing unit may be a general-purpose device such as a laptop or desktop personal computer, a server, a smart/mobile phone, a personal digital assistant, a tablet computer, or other computing device including mobile computing devices. In the case that the external processing unit is implemented with a general-purpose device, the general-purpose device may include one or more processors and a non-transitory computer-readable storage medium (e.g., an instruction register, an on-chip cache, a memory, a hard drive, a removable medium such as an optical medium) having encoded thereon instructions for execution by the processor(s), where the instructions cause the processor to carry out the operations described above as performed by the external processing unit. The internal processing unit may, in some embodiments, be any appropriate IC chip or other hardware component with processing capabilities. The external and internal processing units may be located proximate to one another (e.g., within a same room, or within 5 feet) or may be located remote (e.g., in different parts of a building or complex of buildings) or geographically remote (e.g., miles apart) from one another, such as in the case that the external processing unit is implemented in a server and data is transmitted via one or more networks or the Internet.

Figure 20:
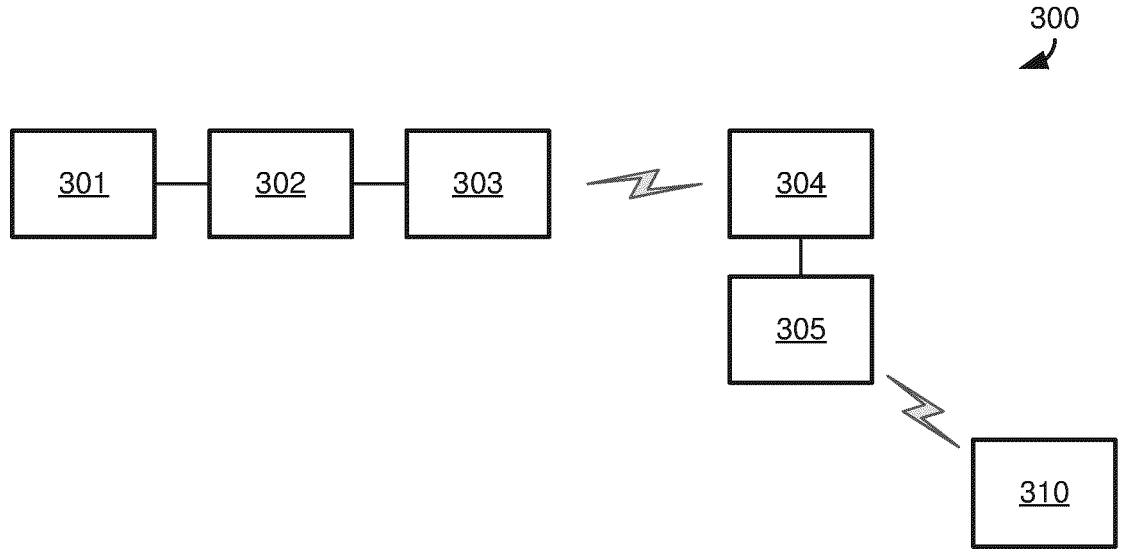
Figure 21B:
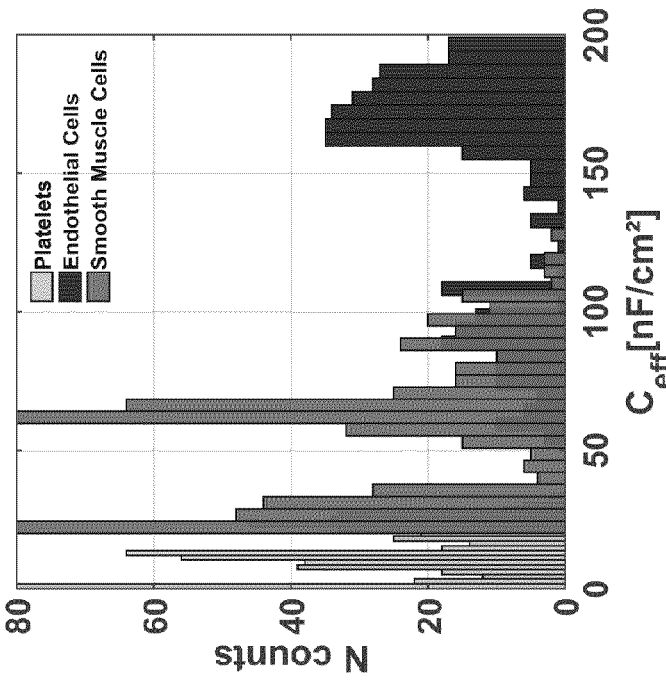
FIG. 21B is a histogram showing the determined effective capacitance of multiple types of cells under uncontrolled conditions.
Figure 21A:
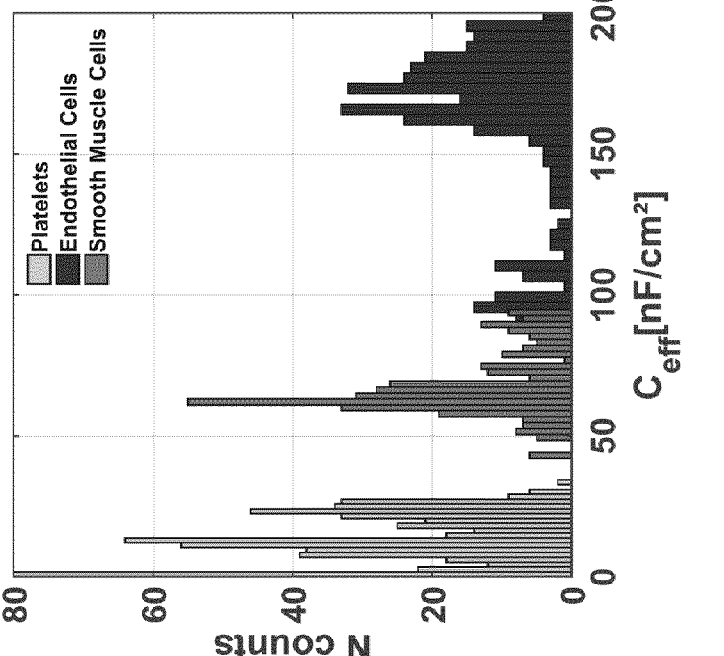
FIG. 21A is a histogram showing the determined effective capacitance of multiple types of cells under controlled conditions.

In a variant, as shown in FIG. 20, part of the processing is carried out in a distant server 310 to which data is transmitted via the internet for example.

Examples

Figure 25:
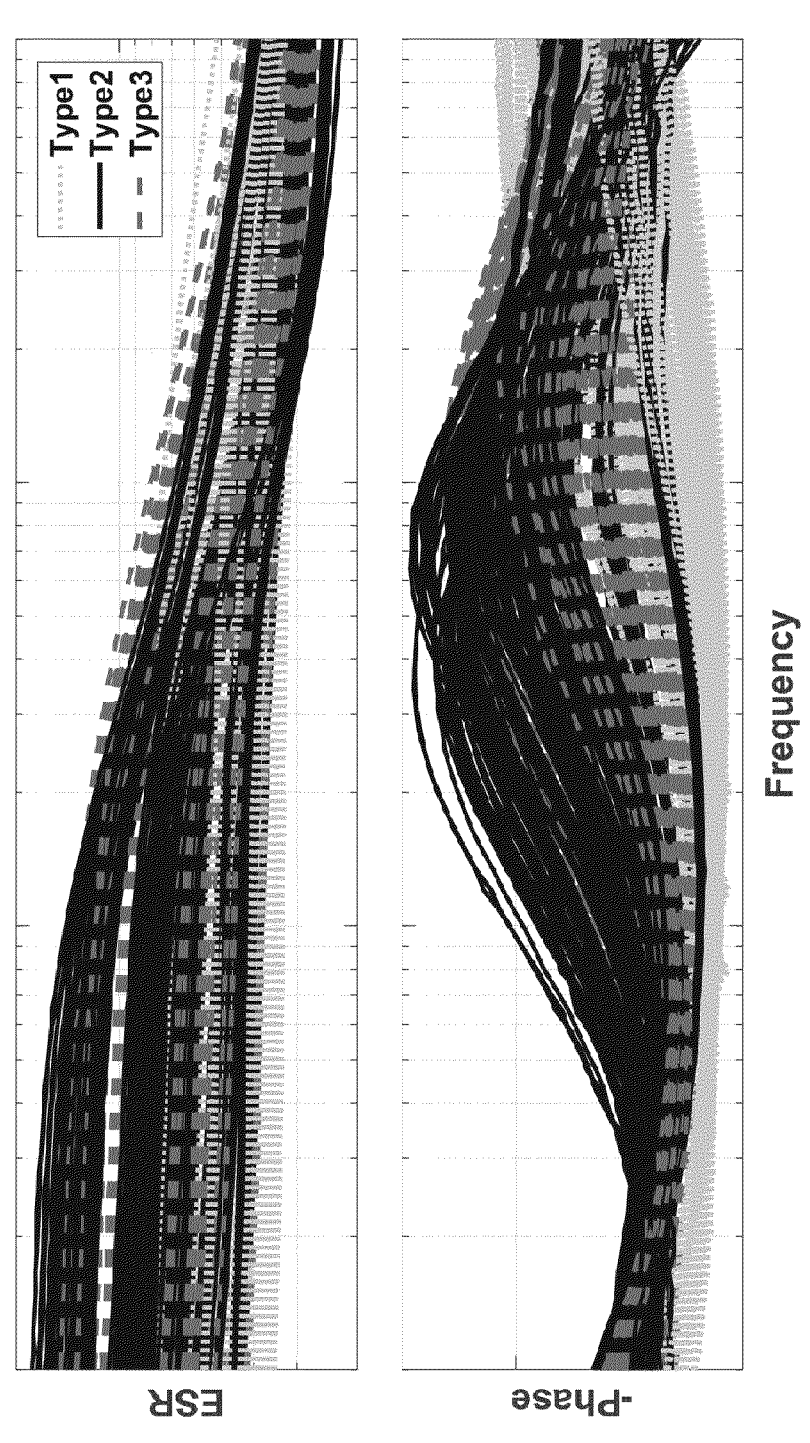
FIG. 25 is a graph showing amplitude and phase spectra for experimental data.

FIG. 25 shows a collection of amplitude and phase of an impedance spectra measured for cellular structures comprising respectively three cell types, i.e. platelets, smooth muscle cells and endothelial cells.

Comparative Examples

First, an equivalent circuit model without CPE is used, consisting of a double layer capacitance Cdl in series with a solution resistance in series with a R0Cmix (R0 resistance in parallel with Cmix capacitance).

Then, the Cmix parameter describing the impact of the cells layers on the complex impedance is computed.

Figure 26A:
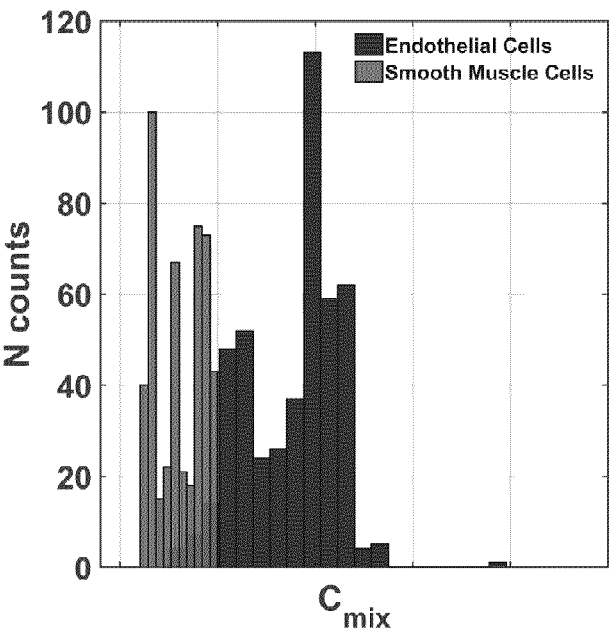
FIGS. 26A-27F are histograms showing various parameters distributions.
Figure 26B:
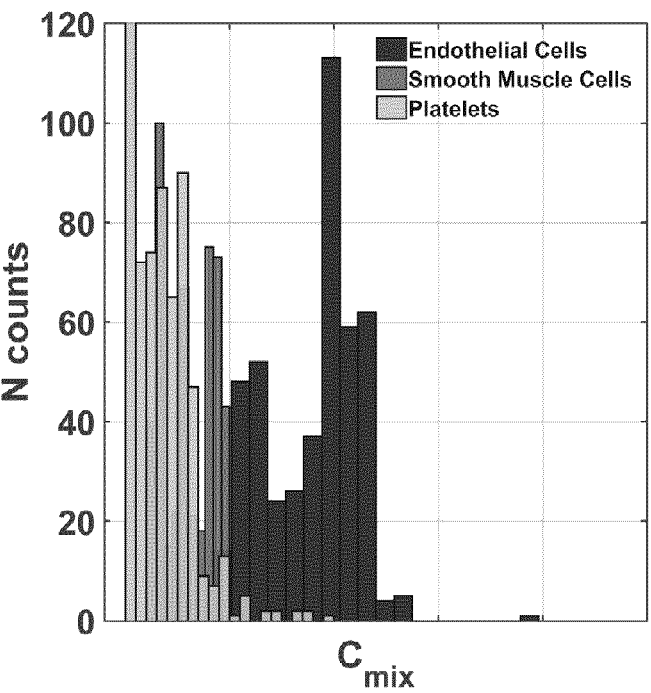
Figure 27A:
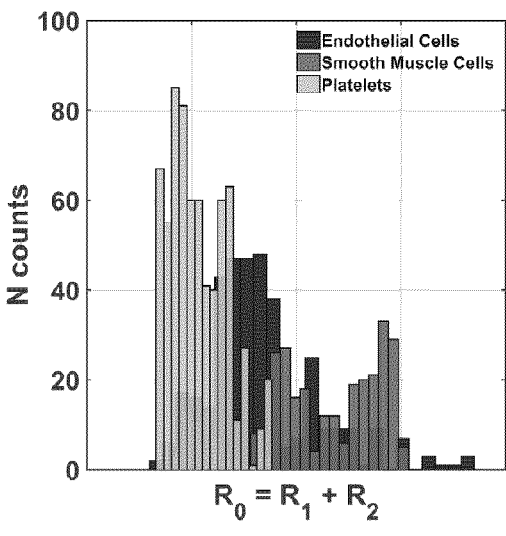
Figure 27B:
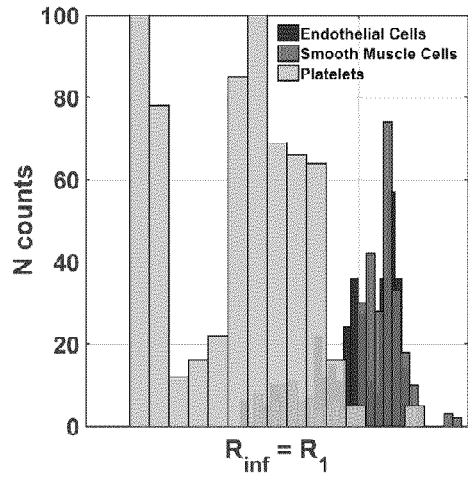
Figure 27C:
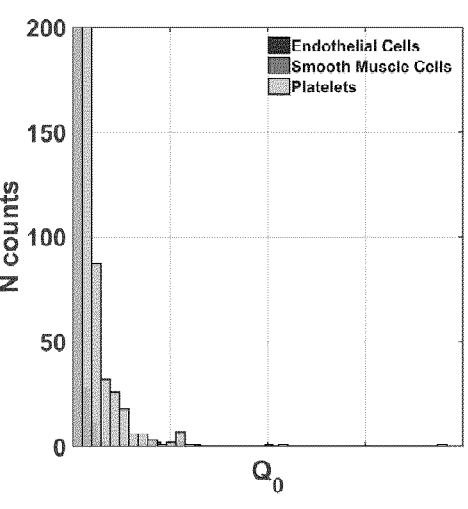
Figure 27D:
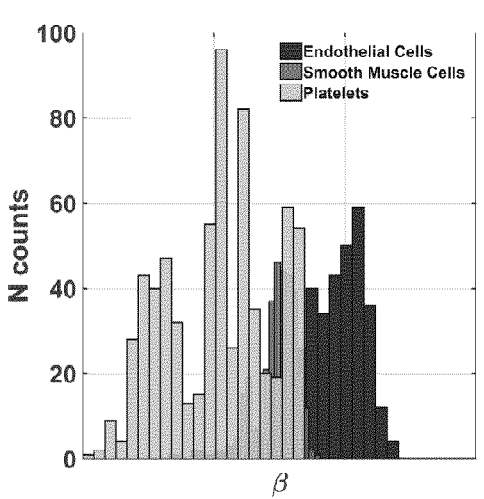
Figure 27E:
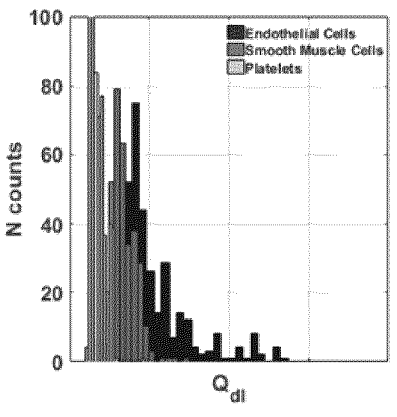
Figure 27F:
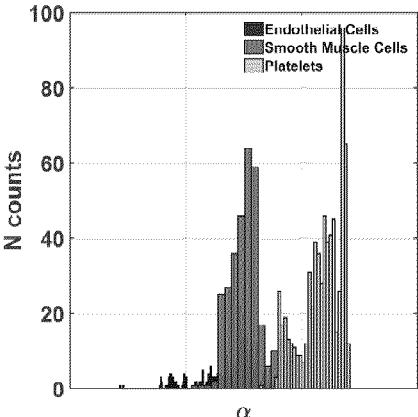

The result of the distribution of Cmix for two cell types is shown in FIG. 26A. It is possible to distinguish between the two cell types. However, if adding a third cell type the three cell types cannot be distinguished any longer, as shown in FIG. 26B.

If one uses a more sophisticated approach and implement CPE elements into the equivalent circuit model, and uses for example the model 34 shown in FIG. 8A, there are six parameters describing the system, i.e. R0, Rinf, Q0, β, Qdl and α.

These parameters can be computed so that the impedance of the equivalent circuit model best fit the experimental impedance spectra curves in FIG. 25.

Then, one can display for each parameter the distribution of this parameter for the three cell types, as shown in FIGS. 27A to 27F.

One can see that for each parameter the three cell types cannot be distinguished clearly, and no linear combination of these parameters can provide the cell discrimination that is looked for.

Examples

Figure 28:
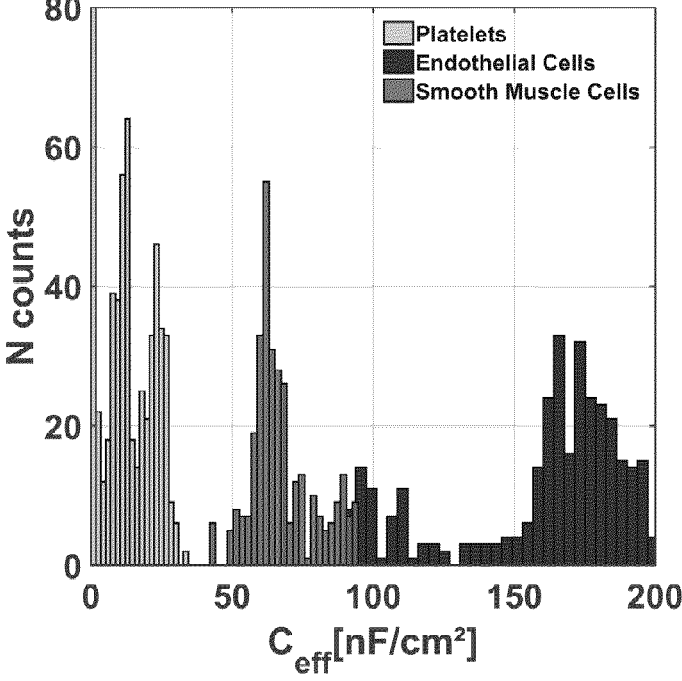
FIGS. 28-30 are histograms showing distributions of values representative of effective capacitance for different cell types.

FIG. 28 shows the distribution of a value representative of the effective capacitance Ceff for the three cell types, determined based on the formula [8] above.

One can see that it is possible to clearly distinguish between all three cell types. The precision is over 90%. The differentiation between cells is significantly improved compared to FIGS. 27A-27F.

Figure 29:
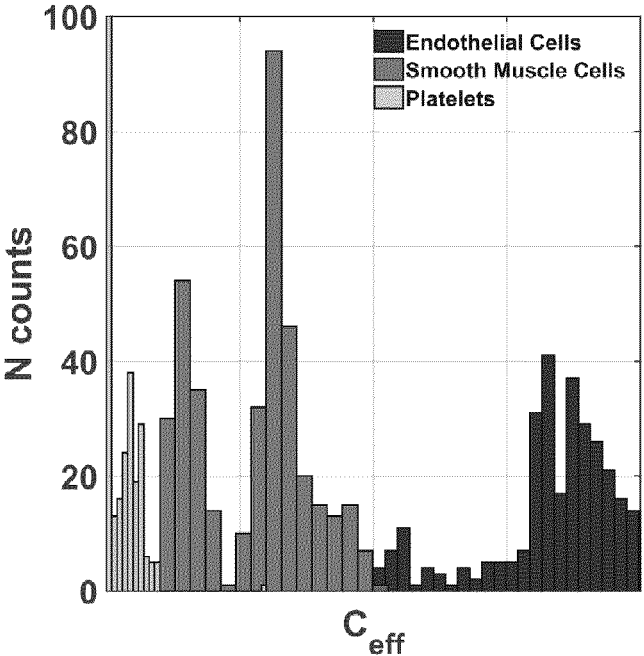

If the equivalent circuit is the one 34' of FIG. 8B, one obtains the Ceff distribution of FIG. 29.

Figure 30:
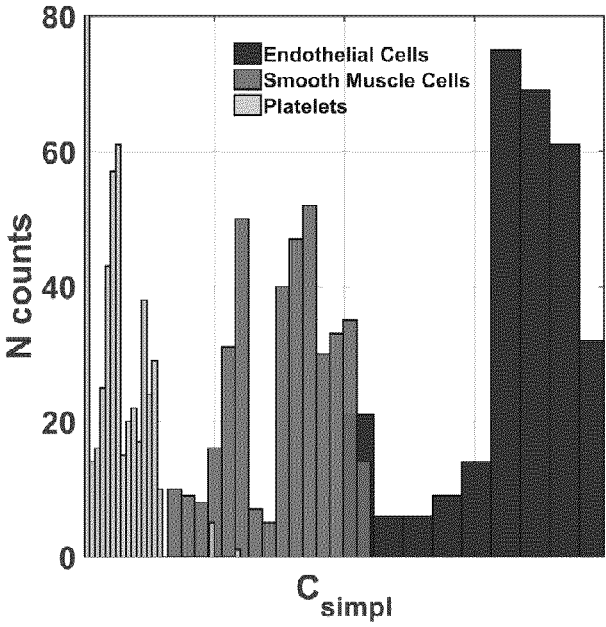

If one considers R0-Rinf is large in respect to Rinf, the equation [8] can be simplified as Ceff=$(1-\alpha)/\alpha$ The resulting distribution of Ceff is shown in FIG. 30. One can see that the three cell types can still be distinguished with a precision of about 85%.

The distributions shown in FIGS. 28-30 may serve as reference data for cell type determination.

For example, an impedance spectrum may be measured in similar conditions as the impedance spectra of FIG. 25, and based on this spectrum the values of parameters R0, Rinf, Q0, β, Qdl and α are determined. This determination may be based on least square fitting of the impedance curves of amplitude and phase with the equivalent circuit model 34 of FIG. 8.

Then, once the parameter values R0, Rinf, Q0 and α are known, the effective capacitance Ceff can be computed and the value compared with the distribution of FIG. 28 to determine to what cell type it corresponds. For example, a low value of Ceff in nF/cm2 will indicate that the cells are of first type; a value between about 50 and about 100 that the cells are of type 3, and a value of over about 100 that the cells are of type 2.

Methods of Operating a Medical Device

Examples of medical devices, sensors, and manners of sensing tissues/materials of a lesion are described in detail above with respect to FIGS. 2-11. Described below in connection with FIGS. 12-16 are examples of techniques that may be implemented by such a medical device and/or that a medical device may be operated to perform.

Figure 12:
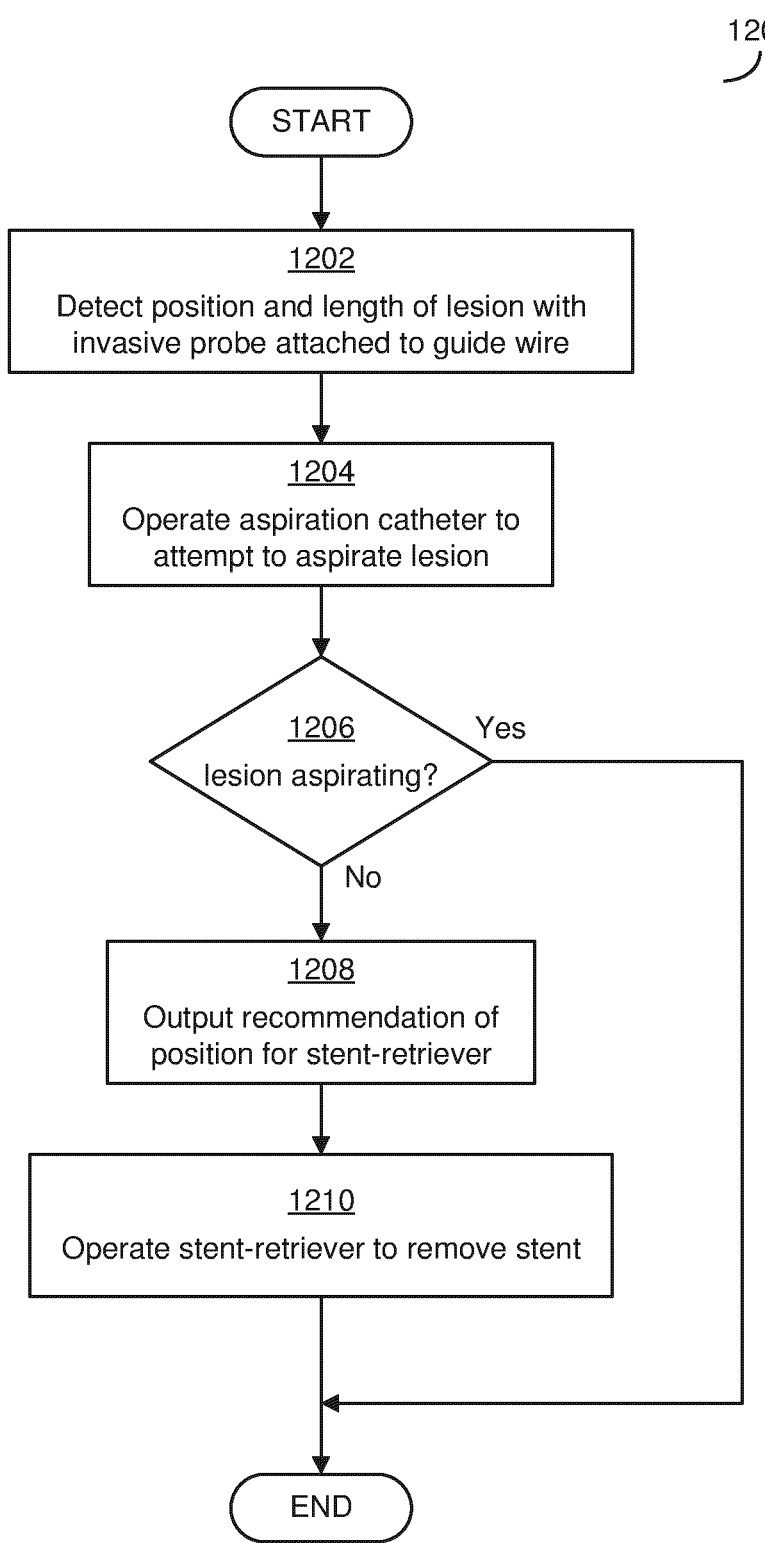
FIG. 12 is a flowchart of an illustrative method for operation of medical devices in accordance with some embodiments described herein to generate treatment recommendations.

FIG. 12 illustrates, for example, a process 1200 that may be performed by a medical device operating in accordance with some techniques described herein. The medical device of the example of FIG. 12 may be a medical device in which an invasive probe may include only a single sensor, which may include one or two electrodes. As should be appreciate from the foregoing discussion, a limited amount of information regarding a lesion may be determined from a single sensor, as compared to multiple sensors arrayed along an invasive probe (e.g., in the example of FIG. 3). In the example of FIG. 12, the sensor of the invasive probe may be disposed in treatment devices, such as in an aspiration catheter and in a stent-retriever, and/or in a guide wire that is inserted prior to insertion of the aspiration catheter or stent-retriever. The medical device may generate treatment recommendations based on characteristic(s) of the lesion determined using the sensor.

The process 1200 begins in block 1202, in which a sensor attached to a guide wire is operated to detect one or more characteristics of a lesion that is proximate to the sensor. Prior to the start of the process 1200, an invasive probe of the guidewire, of which the sensor is a part, may be inserted into vasculature of an animal and moved proximate to a predicted location of the lesion. The sensor then is operated to detect when the sensor contacts the lesion. Contact of the lesion may be determined by evaluating a change over time in a value output by the sensor. For example, the sensor may output one value when contacting blood, which may be the case when the sensor is disposed in a middle of a vessel at an area not blocked by the lesion. When the invasive probe is moved forward until contacting the lesion, a value output by the sensor may change once contact is made. In this manner, a location of the lesion may be determined using the single sensor. The sensor may additionally, in some cases, be operated to determine a length of the lesion, such as by continuing to advance the invasive probe until the sensor is no longer contacting the lesion and the output value returns to a value that was associated with contacting blood.

In the example of FIG. 12, using only a single sensor, the medical device may not be aware of a composition of a lesion and may not be able to make treatment recommendations regarding which treatment option may be best to treat a particular lesion. However, the medical device may be able to produce information regarding a progress or success of a treatment, which may be used to determine whether a selected treatment option is being performed successfully. Based on this information, the medical device may generate a treatment recommendation on whether to change a treatment being performed to another treatment.

In one treatment protocol that may be implemented in embodiments such as FIG. 12, an aspiration catheter may be used as a first option for treatment of a lesion. Accordingly, in block 1204, an aspiration catheter is inserted into vasculature until located proximate to the invasive probe of the guidewire and thus located proximate to the lesion. In some embodiments, a guidewire may not be inserted first, but rather the aspiration catheter may be inserted in block 1202 until positioned proximate to the lesion. In such a case, the sensor may be a component of the aspiration catheter. Embodiments are not limited in this respect.

In block 1204, following placement of the aspiration catheter proximate to the lesion, the aspiration catheter is operated to attempt to aspirate the lesion into the catheter. Following a time, the sensor of the guidewire and/or aspiration catheter may be operated to determine whether the aspiration catheter is having an effect on the lesion. Some lesions, such as hard lesions, may not be able to be aspirated using an aspiration catheter. For these lesions, other interventions (such as a stent-retriever) may be used. Accordingly, in block 1204, in addition to operating the aspiration catheter to attempt to aspirate, the sensor may be operated to determine whether a change has been seen in the lesion. This may be done, for example, by positioning the sensor within the lesion prior to a start of aspiration, such as at a portion of the lesion closest to the aspiration catheter, and determining after a time whether the value output by the sensor indicates that the sensor is no longer in contact with the lesion (and is rather, for example, in contact with blood).

If during (and potentially as a result of) operation of the aspiration catheter the sensor no longer contacts the lesion, a determination may be made in block 1206 that the lesion is aspirating. In this case, a treatment recommendation may be generated and output indicating that the aspiration catheter appears to be successfully treating the lesion and that continued operation of the aspiration catheter is recommended. In the example of FIG. 12, the process 1200 then ends. It should be appreciated, however, that in some embodiments successive determinations may be made over time for whether the aspiration catheter is continuing to successfully treat a lesion, such that a change may be recommended if appropriate or that a determination may be made of when a lesion has been fully aspirated.

If, however, the value output by the sensor is not changing during the aspiration and indicates that the aspiration is not having an effect on the lesion, a treatment recommendation may be generated and output that an aspiration catheter is no longer recommended and that instead, another treatment option is recommended. In the example of FIG. 12, a second option for treatment of a lesion may be a stent-retriever. Accordingly, in block 1208, a recommendation to use a stent-retriever may be output. In block 1210, the stent-retriever may be operated to treat the lesion by removing it with the stent-retriever. For example, the stent-retriever may be inserted until located proximate to the lesion. In some embodiments, as discussed above, the sensor with which a detection is made may be a component of a guide wire, separate from a treatment device. In such a case, the stent-retriever may be inserted along the guide wire (or inserted along a micro-catheter inserted along the guidewire, following removal of the guidewire), following removal of the aspiration catheter, until the stent-retriever is positioned proximate to the lesion. As another example, the sensor may be integrated with the stent-retriever and may detect when the stent-retriever is located proximate to the lesion. The medical device, through a value produced using the sensor, may generate a treatment recommendation regarding positioning of the stent-retriever for removal of the lesion. For example, the sensor may be used, as discussed above, to detect when an invasive probe has traversed a lesion and a distal end of the invasive probe is located on a far side of the lesion. It may be best to position a stent of a stent-retriever across a lesion, such that one end of the stent protrudes beyond the lesion, to aid in ensuring that a lesion is fully captured with a stent. Accordingly, by operating a sensor to detect a far side of a lesion, and recommending that a stent-retriever be inserted until the stent or sensor extends through the lesion, a treatment recommendation may be made regarding proper positioning of a stent.

Once the stent-retriever is operated to remove the lesion in block 1210, the process 1200 ends.

Figure 13:
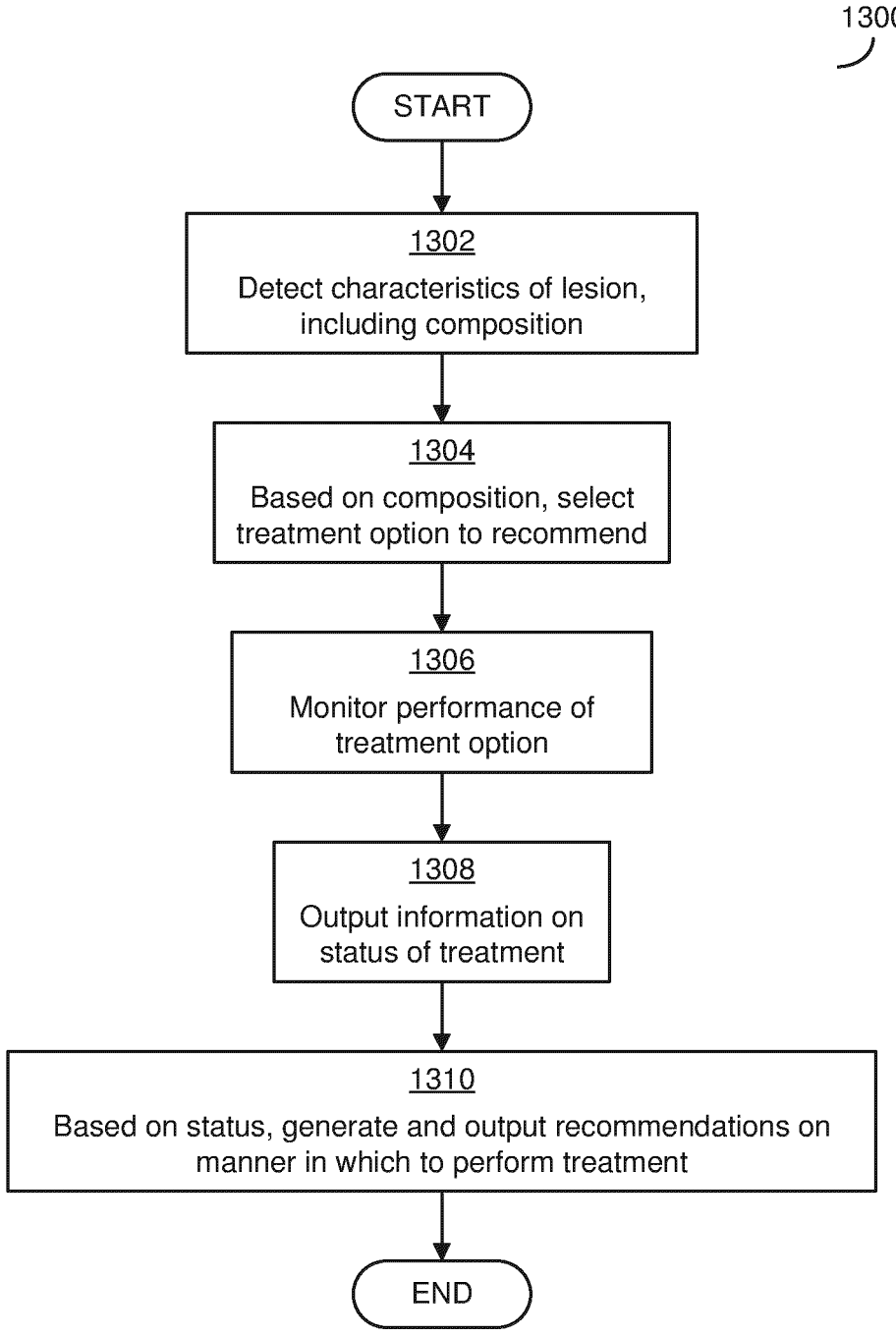
FIG. 13 is a flowchart of another illustrative method of some embodiments for operation of medical device in accordance with embodiments described herein to generate treatment recommendations based in part on a composition of a lesion.

FIG. 13 illustrates an example of a manner of operating a medical device to generate treatment recommendations for a lesion in accordance with another embodiment. In the embodiment of FIG. 13, an invasive probe may include multiple sensors arrayed along an exterior of a probe, such as in the example of FIG. 3 discussed above. As should be appreciated from the foregoing, with such an array of sensors, several different characteristics of a lesion may be determined, including composition of the lesion. For example, by performing an EIS process on the lesion, a composition of the lesion may be determined, as discussed above. The composition of the lesion may indicate different biological materials present in the lesion, such as different tissues or cells, or other biological materials such as plaque materials. In some such embodiments, for example, each sensor (e.g., the two electrodes of each sensor) may contact biological materials of the lesion, with some sensors contacting different biological materials of the lesion than do other sensors. Each sensor may then be operated, in accordance with techniques described herein, to determine an impedance spectrum of the biological material contacted by the sensor. This set of impedance spectra may then be used to determine a composition of the lesion, such as by identifying different biological materials present in the lesion. This composition information may be similar to the information that may be determined from performing a histology on the lesion. From the different impedance spectra for the lesion, and/or an identification of the different biological materials present in the lesion (e.g., the different tissues or plaque materials), characteristics of the lesion as a whole may be determined, such as by identifying (e.g., diagnosing) a type of the lesion.

For example, by performing an EIS process on the different biological materials of the lesion, it may be determined whether any of the following cells or tissues are present in the lesion: platelets, fibrins, thrombi, red blood cells, white blood cells, smooth muscle cells, elastic fibers, external clastic membrane, internal elastic member, loose connective tissues, endothelial cells, or any other tissue of a tunica intima, media or externa. In addition, by performing an EIS process on the lesion, the relative amount of each of the present cells or tissues may be determined. As a simple example, it may be determined that a lesion is composed by 50% red blood cells, 30% fibrin and 20% platelets. From this information, the lesion may be categorized as one particular type of lesion from a set of lesions, such as by diagnosing the lesion as being of one type of lesion rather than other types of lesions.

The process 1300 of FIG. 13 begins in block 1302, in which an invasive probe of a medical device is inserted into vasculature of an animal subject and operated to detect one of more characteristics of a lesion, including a composition of a lesion. Based on the characteristics, including the composition, the medical device may in block 1304 select a treatment option to recommend. The medical device may select the treatment option in any suitable manner, including according to a technique described below in connection with FIGS. 14-15B.

The treatment option that is selected may be selected based on a composition of the lesion. For example, if a composition of the lesion indicates that it is composed of smooth muscle tissue rather than a thrombus, the medical device may determine that implantation of a stent is a treatment that should be recommended. This may be because the lesion is not composed of cells/materials that may be extracted, but is instead a growth within the vessel. As another example, if the composition of the lesion indicates that it is a soft lesion, such as a soft lesion made of freshly-formed thrombus, the medical device may recommend an aspiration catheter. This may be because soft lesions are capable of being aspirated. As a further example, if the composition of the lesion indicates that it is a hard lesion, such as a hard blood clot, the medical device may recommend a stent-retriever, because it is unlikely that a hard lesion would be successfully aspirated.

Once a treatment is recommended in block 1304, the medical device may in block 1306 monitor performance of a treatment option that is selected. The medical device may monitor the treatment using one or more sensors, such as the one or more sensors with which the characteristics were determined in block 1302 or one or more sensors of a treatment device that is operated to perform the treatment. For example, in some embodiments, following the recommendation of block 1304, a clinician may insert another device into vasculature of the subject (e.g., an aspiration catheter, stent-retriever, etc., as appropriate) and the other device may include an invasive probe have an arrangement of sensors as described herein. In such an embodiment, the medical device may monitor the performance of the treatment using the sensors of the invasive probe of the other device.

The monitoring of the treatment in block 1306 may produce information regarding a status and/or progress of a treatment. For example, if the treatment is being performed with an aspiration catheter, the monitoring may produce information on an extent to which a lesion has been aspirated, and/or a remaining amount of the lesion to be aspirated. The progress may be monitored, for example, by the medical device periodically or occasionally inflating a structure (e.g., the stent-like mesh of FIG. 3) to contact a remaining portion of the lesion with sensors, to determine an extent of the lesion that remains. After the determination is made, the structure may be removed to continue aspiration of the lesion. If, on the other hand, the treatment is being performed with a stent-retriever, the monitoring may produce information on an extent to which a stent has coalesced with a lesion during inflation of the stent. For example, by monitoring sensors along an exterior of the stent (e.g., with an arrangement of sensors on a stent like the example of FIG. 3), a determination may be made of whether each portion of a stent corresponding to each sensor is fully expanded into a lesion. This determination may be made in any suitable manner, including by monitoring a change over time in values produced by each sensor and determining when a value for each sensor stops changing. When each sensor stops changing value, this may indicate that there has been no further change in an interaction between a lesion and a stent and, as such, the stent is fully expanded into the lesion and the lesion is coalesced around the stent.

Making such determinations may aid in performance of a treatment of a lesion. Accordingly, in block 1308, information on a status of a treatment is output by the medical device via a user interface, for presentation to a clinician. In addition, in block 1310, the medical device may generate one or more treatment recommendations on a manner in which to perform the treatment. For example, when the medical device determines that a lesion is fully coalesced with a stent during operation of a stent-retriever, as discussed above, the medical device may output a treatment recommendation that extraction of the stent begin.

Once the treatment is successfully performed, the process 1300 ends.

While an example of monitoring a treatment is given in the context of generating treatment recommendations, it should be appreciated that similar techniques may be used to raise error messages or other messages to a clinician regarding a status of a treatment. For example, if a sensor on a treatment device indicated presence of the lesion for a time, after which the sensor no longer detects the lesion, the medical device may determine that the treatment device is improperly positioned or that the lesion was lost. This may indicate either that the device needs to be repositioned or, potentially more problematically, that the lesion has become an embolism. A message to the clinician via the user interface may indicate such a potential problem.

Additionally, while the example of FIG. 13 described a manner of operating a medical device to provide treatment recommendations both relating to an initial selection of a treatment and related to a subsequent manner of performing that treatment, it should be appreciated from the foregoing that embodiments are not so limited. For example, in some embodiments, a medical device may include one or more sensors as described herein and may be operated to produce treatment recommendations on a manner of operation of that device, without generating an initial recommendation to use that device. For example, a stent-retriever or aspiration catheter, as discussed above, may include one or more sensors to generate data on a status or performance of a treatment and may produce treatment recommendations. As another example, a guidewire for treatment of a Chronic Total Occlusion (CTO) may generate information on a tissue/material contacted by a sensor and generate treatment recommendations. In a CTO procedure, the guidewire may be inserted through smooth muscle tissue or the plaque of a blood vessel when a solidified thrombus cannot be penetrated. Treatment recommendations may be made, based on sensed characteristics of tissue/material contacted by a sensor, of when a guidewire is positioned against the smooth muscle tissue and can be advanced and when the guidewire has been advanced through the endothelial tissue and is once again within the blood vessel, on a far side of the lesion. In addition, in some embodiments, one or more measurements may be taken of a thickness of smooth muscle tissue or other characteristics of the vessel wall that may be informative of a risk that the guidewire will puncture the tissue rather than navigate through the tissue. For example, if a measurement indicates a thinning of the smooth muscle tissue on one side of an invasive probe of the guidewire, this may indicate that the invasive probe is at risk of puncturing the vessel wall. A treatment recommendation may be made to proceed more slowly and/or to withdraw the guidewire, or another recommendation may be generated.

Figure 14:
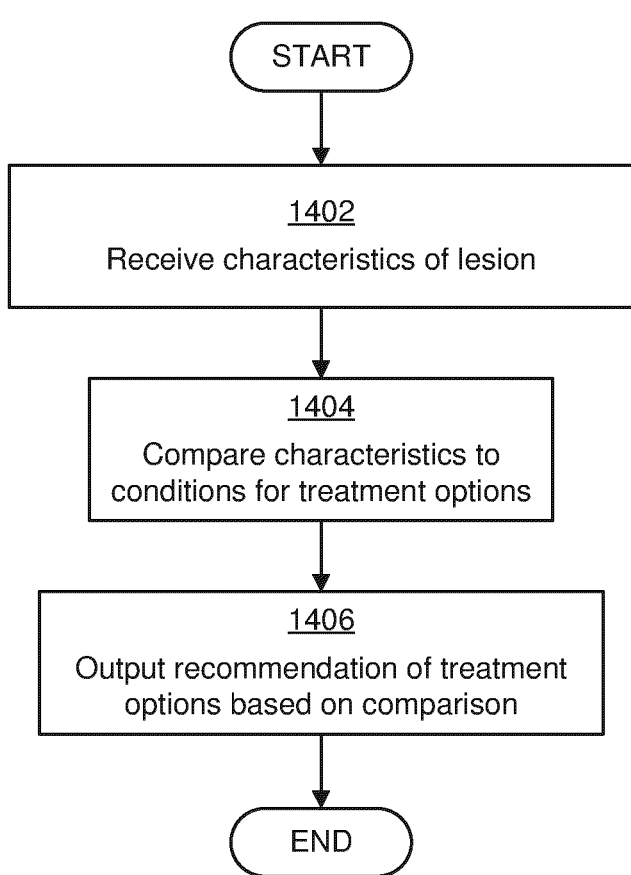
FIG. 14 is a flowchart of an illustrative manner of generating treatment recommendations using conditions, which may be implemented in some embodiments.

Those skilled in the art will appreciate from the discussion herein that there are a variety of ways in which a medical device may be configured to generate treatment recommendations based on characteristics of a lesion and/or a status of a treatment. FIGS. 14-15B illustrate one example of a technique that may be used for generating treatment recommendations.

FIG. 14 illustrates a process 1400 that may be implemented by a medical device in some embodiments for generating treatment recommendations.

The process 1400 begins in block 1402, in which the medical device receives one or more characteristics of a lesion. The medical device may receive the characteristic(s) from a component of the medical device, such as in a case that the characteristic(s) are determined using one or more sensors included in an invasive probe of the medical device and/or by another component (e.g., a lesion analysis facility) that generates characteristic(s) based on data produced by the sensors. The characteristic(s) may include a composition of the lesion, in some embodiments. The characteristic(s) may additionally or alternatively include a location of the lesion within the body, one or more dimensions of the lesion (e.g., a length, a thickness, etc.), a temperature of the lesion, or other information that may be determined based on the types of sensors described above.

In block 1404, the medical device compares the characteristic(s) received in block 1402 to one or more conditions for one or more treatment options. The medical device may be configured with information on multiple different available treatment options, each of which may be associated with one or more conditions that relate to one or more characteristics of lesions. For example, the medical device may be configured with one or more conditions for treatment of a lesion by implantation of a stent, one or more different conditions for use of an aspiration catheter, and one or more further different conditions for use of a stent-retriever. Examples of such conditions related to a composition of a lesion are described above in connection with FIG. 13.

The medical device may compare the characteristic(s) of the lesion to the conditions to determine which conditions are met. In some embodiments, the sets of conditions for treatment options may be mutually exclusive, such that a lesion may meet only one set of conditions and thus only one treatment option may be selected. In other embodiments, the set of conditions may not be mutually exclusive, and the medical device may determine which treatment option to recommend by identifying the one for which the most corresponding conditions are met or the one for which the corresponding conditions are met most closely (e.g., in the case that a condition is associated with a range of values, the condition for which a value most closely matches the range by, for example, falling in a middle of the range).

In block 1406, based on the comparison, the medical device may output a recommendation of a treatment option via a user interface of the medical device, and the process 1400 ends.

While the process 1400 is described in connection with generating an initial treatment recommendation for a treatment of a lesion based on characteristics of a lesion, those skilled in the art will understand how to extend the technique to generation of treatment recommendations during performance of a treatment, as described above in connection with block 1310. For example, in some embodiments, based on comparison of characteristics of a lesion (e.g., composition of the lesion) to one or more conditions for certain parameters of a treatment, such as a speed at which to extract a stent of a stent-retriever, the medical device may output recommendations on such parameters.

Those skilled in the art will appreciate that there are a number of ways in which to set the conditions for treatment options that may be used in connection with a process like process 1400 of FIG. 14. For example, values for characteristics of a lesion to use as conditions may be hard-coded into a medical device following at least some experimentation to determine a correspondence between the values, types of lesions, and successful treatment with various treatment options. The inventor has recognized and appreciated, however, the advantages of a system to learn such relationships and conditions based on characteristics of lesions and information on successful treatments of lesions, among other information. For example, a machine learning process, such as one that may include feature extraction and/or classification, may be implemented in some embodiments.

Figure 15A:
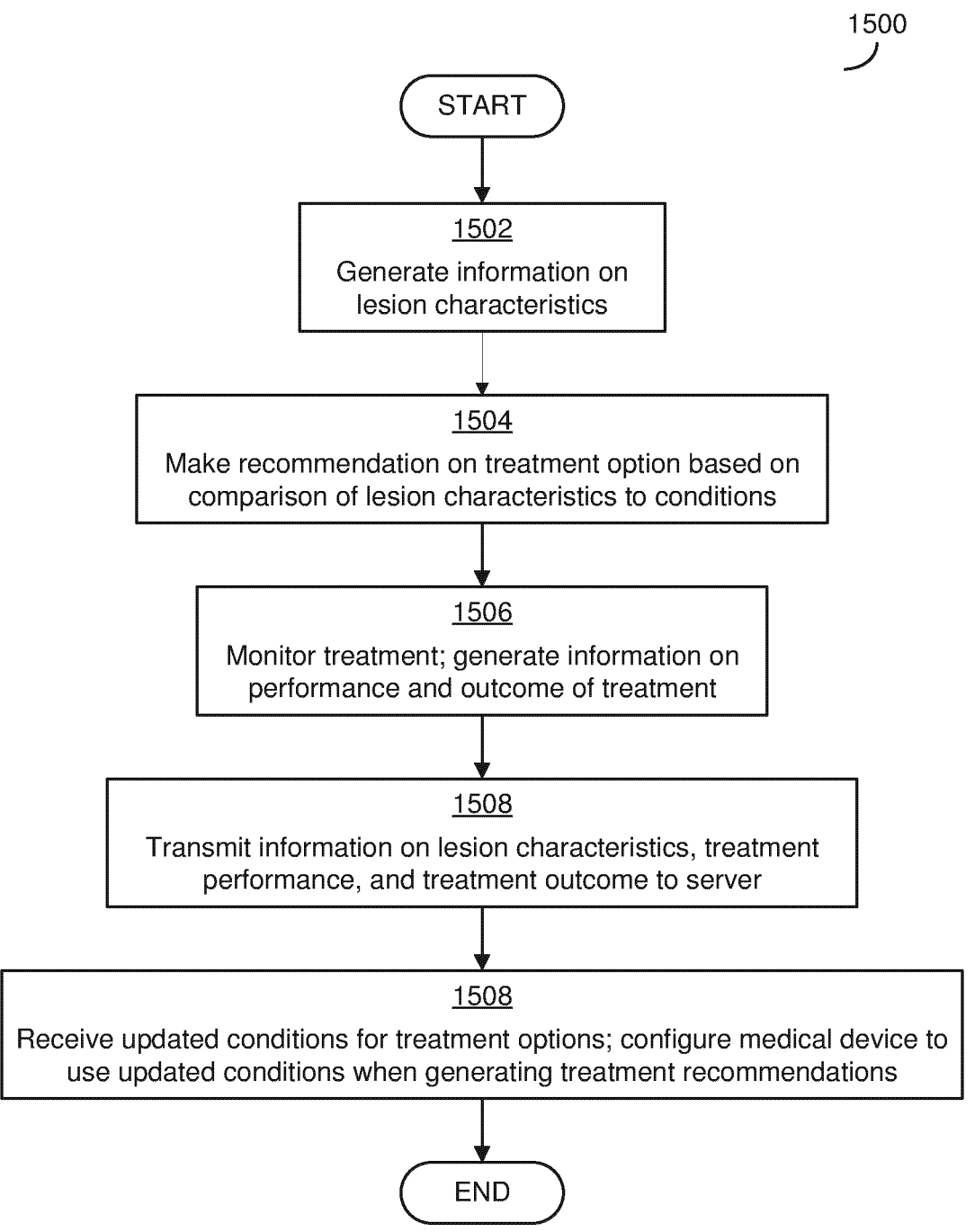

FIGS. 15A-15B illustrate an example of a machine learning process that may be performed in some embodiments. FIG. 15A illustrates a process that may be implemented by a medical device, whereas FIG. 15B illustrates a process that may be implemented by a computing device (e.g., a server) in communication with multiple different medical devices.

The process 1500 of FIG. 15A begins in block 1502, in which a medical device generates information on characteristics of a lesion. In blocks 1504 and 1506, the medical device may make recommendations on treatment options based on a comparison of lesion characteristics to conditions for treatment options as well as monitor a progress of a treatment and generate status information throughout the treatment. These operations of blocks 1502-1506 may be implemented similar to the manner described above in connection with FIGS. 13-14 and thus, for the sake of brevity, will not be described further. In addition, in block 1506, the medical device may generate information on an outcome of a treatment. The outcome of the treatment may indicate whether a lesion was successfully treated, whether the lesion was dislodged and released into the subject's body, whether multiple treatments were necessary, or other information indicating an outcome. The information indicating the outcome may be generated using sensors of the medical device, as should be appreciated from the foregoing. For example, using data generated by an accelerometer in a handle of the medical device, the medical device may determine whether it was operated multiple times to remove a lesion. As another example, as discussed above, if a sensor was detecting a lesion then stopped detecting the lesion, this may be an indication that the lesion has moved in the subject, including that the lesion was dislodged and became an embolism.

In block 1508, the information generated in blocks 1502-1506 is transmitted from the medical device, via one or more wired and/or wireless communication connections and/or networks, including the Internet, to a computing device. The computing device may be, in some embodiments, geographically remote from the medical device. In block 1508, following the transmission in block 1506, the medical device receives from the computing device (such as via the network(s) via which the information was transmitted in block 1508) one or more updated conditions for treatment options. The updated conditions may identify new values for evaluation of conditions with respect to characteristics of lesions. The medical device may configure itself to apply the one or more updated conditions for generation of treatment recommendations, such as through considering the one or more updated conditions in the context of a process like the one discussed above in connection with FIG. 14. Once the medical device is configured with the updated conditions, the process 1500 ends.

FIG. 15B illustrates a process that may be implemented by a computing device to perform a learning process on reports on treatments of lesions, to generate conditions for use in selecting treatment recommendations such as via a process like the one discussed above in connection with FIG. 14. Specifically, in the example of FIG. 15B, a computing device analyzes reports on treatments of lesions, in connection with information regarding characteristics those lesions, to identify relationships between successful (and/or unsuccessful) treatments and characteristics of lesions. Through identifying such relationships, conclusions may be drawn about which treatment options are best for particular types of lesions and, based on those conclusions, a treatment recommendation may be generated for treatment of a particular lesion based on characteristics of that lesion, as in the example of FIG. 14. Similarly, as discussed above, based on information regarding status or performance of a treatment, recommendations on a manner of performing a treatment (e.g., a time at or speed with which to extract a stent during a stent-retrieval) may be determined. While the example of FIG. 15B will be described in context of generating conditions for an initial selection of a treatment option to use for a lesion based on characteristics of a lesion, those skilled in the art will understand from the description below how to extend the technique for use with generating recommendations on a manner in which to perform a treatment.

The inventor has recognized and appreciated that the generation of such conditions and the identification of relationships between successful/unsuccessful treatments and characteristics of lesions may be advantageously determined using a machine learning process. Various machine learning algorithms are known in the art and may be adapted for use in this context. Some machine learning algorithms may operate based on feature extraction and classification techniques, in which groups (classifications) for units are identified and an analysis of properties of units is carried out to determine which properties, and/or values of those properties, most closely correspond to or predict correct membership in the groups. Based on these identified properties, subsequently-received unclassified units having such properties can be "classified" into one of the groups/classifications based on a comparison of the properties and/or values of the properties of the unclassified unit to the properties/values for each group. In some machine learning applications, the groups/classifications may be identified manually during a configuration of the machine learning process. In addition, or in others, the groups/classifications may be determined or adjusted over time by the machine learning process, such as through creation of new groups/classifications when the machine learning process perceives through its analysis that a new grouping may better characterize some units. A full discussion of machine learning is outside the scope of this document and not necessary for an understanding of techniques described herein. Those skilled in the art will understand how to implement a machine learning technique for use with information and goals described herein.

Here, groups may be defined as treatment options or treatment outcomes, and the example of FIG. 15B will be described in this context. In this case, the groups may be defined by characteristics of lesions and/or statuses of treatment. In this case, when characteristics of a lesion and/or of a status of treatment match characteristics for group, the corresponding treatment option may be selected for output. Additionally or alternatively, in some embodiments groups may be associated with different types of lesions (each type having one or more characteristics or ranges of characteristics different from the other types) and/or status of treatment, and these different groups may then be associated with particular treatment options or ways in which to operate a treatment device. In this latter case, when characteristics for a particular lesion or status of a treatment match a group, the corresponding treatment recommendation(s) for the group may be selected for output.

The process 1520 of FIG. 15B begins in block 1522, in which a learning facility executing on one or more computing devices receives, over time, multiple reports on treatment of lesions by medical devices. The medical devices may be medical devices operating in accordance with embodiments described above. The reports may include information on a lesion that was treated, such as one or more characteristics of the lesion. The report may also include information on a manner in which a lesion was treated, such as on one or more treatment devices that were operated to treat the lesion and the manner in which those lesions were treated. Information on an outcome of the treatment may also be included in a report, such as whether a treatment was successful, whether multiple treatments were necessary, whether a lesion was dislodged and became an embolism, or other outcomes.

The reports may contain information determined by one or more sensors of a medical device, including examples of sensors and types of information described above. As discussed above, various types of sensors may be included in embodiments, including one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors. It should be appreciated that various types of characteristics or other information may be generated from these sensors. Any of this information may be included in reports and used in the process 1520 for generating conditions associated with treatment recommendations. For example, as discussed above, an accelerometer disposed within a handle of a medical device may track movements of the medical device and be used to determine whether multiple treatments were performed to treat a clot. As another example, a force sensor may indicate a force with which a stent-retriever is extracted or a set of impedance sensors may determine, based on whether a detected impedance at one or more sensors of a stent of a stent-retriever varies over time during an extraction, whether a lesion is partially or fully separating from the stent during retrieval. Those skilled in the art will appreciate from the discussion above different types of data that may be generated by sensors of a medical device for inclusion in such reports.

Reports may also include information that may be entered by a clinician or retrieved from another system with which the medical device may interoperate. For example, the report may include information on a position of a lesion within anatomy of the subject, such as whether the lesion is in a cranial artery, femoral artery, pulmonary vein, common bile duct, or other duct. This information may be entered by the clinician via a user interface or, for example, retrieved from another system such as an angiogram device.

Optionally, the reports may include information about the patients, such as age, medical history and demographic.

The reports that are received in block 1522 may be received over time from a plurality of medical devices, which may be geographically distributed. By receiving these reports, and the contents of these reports, over time a set of conditions and treatment recommendation that define recommended or best practices may be generated.

Accordingly, in block 1524 the learning facility analyzes the information in the reports to identify relationships between lesion characteristics (and/or manners of operating treatment devices), options for treating lesions having those characteristics, and successful treatments. Based on this analysis, the learning facility may learn relationships between these pieces of information. Such relationships may indicate when certain treatment options are successful or not successful, or for which types of lesions different treatment options are successful or not successful. In at least some of the embodiments in which information about the patients are obtained, the learning facility may learn relationship between lesion characteristics, options for treating lesions having those characteristics, and successful treatments based on the patients' information. The model may be trained to learn which particular piece of information, among all the information obtained about patients, is likely to affect the probability of success of a treatment. For example, the trained model may identify that a particular treatment is likely to have different probabilities of success depending on the age of the patient, even if all the characteristics of the lesion are equal. As such, different treatment recommendations may be provided for two patients having identical lesions but different age. As another example, the trained model may learn that some treatments, when applied to subjects who have suffered a certain condition in the past, are less likely to succeed relative to subjects who have not suffered such a condition, even if the type of lesions are identical.

Based on this analysis in block 1524, the learning facility (through the feature extraction and classification processes of a machine learning process) may in block 1526 generate conditions for each of the treatment options. The conditions may be associated with characteristics of lesions, so as to indicate different characteristics or ranges of characteristics for lesions that may be successfully treated with each treatment option. For example, conditions may relate to a range of values for a visco-elastic property of a lesion, such that a visco-elasticity in one range may be associated with treatment using an aspiration catheter and visco-elasticity in another range may be associated with treatment using a stent-retriever. In this manner, when a lesion having a specific visco-elasticity is detected, a comparison to these conditions may be used (as in the process of FIG. 14) to determine which treatment option to recommend for that particular lesion.

In block 1528, once the conditions are generated in block 1526, the conditions may be distributed to medical devices such that the devices may be configured to use those conditions to generate treatment recommendations, as discussed above in connection with FIG. 15A. Once the conditions are distributed, the process 1520 ends.

While the process 1520 is discussed in FIG. 15B as a discrete process, it should be appreciated that in some embodiments the reception of reports and determination of conditions may be a process that is repeated over time, including continuously or at discrete intervals. Accordingly, in some embodiments the process 1520 may be performed multiple times or, following distribution of conditions in block 1528, the learning facility may return to block 1522 to receive additional reports and continue the learning process.

Examples are provided above of devices and processes for providing feedback to a clinician during a diagnosis and/or treatment of a lesion, including providing treatment recommendations during the diagnosis and/or treatment. In some embodiments, in addition to or as an alternative to providing such feedback during the diagnosis and/or treatment, a medical device may be configured to present information on a diagnosis and/or treatment to a clinician following the operation of the medical device in the diagnosis/treatment. FIG. 16 illustrates an example of such as process.

The process 1600 begins in block 1602, 1604, in which a medical device is operated to generate information on characteristics of a lesion and on performance of a treatment, and recommendations on a manner in which to perform the treatment. The operations of blocks 1602, 1604 may be similar to examples of generation of data discussed above.

In block 1606, following the treatment, the information generated in blocks 1602, 1604 is used by a chronicle generation facility to generate a chronicle of the treatment. The chronicle of the treatment may include information regarding how devices were operated over time, what characteristics of the lesion were detected, what recommendations were made by the medical device, and whether those recommendations were followed by the clinician. If an error was detected in the treatment, such as a loss of a part or entirety of a lesion that resulted in, for example, creation of an embolism or necessity of a subsequent treatment, the chronicle generation facility may analyze the error to determine a cause of the error. For example, if sensors detected at a time that a part of a lesion separated from a stent-retriever, and at an immediately-preceding time another sensor noted application of a sudden force to the stent-retriever, the chronicle generation facility may note this in the chronicle. If a force applied to a stent-retriever exceeded a maximum force recommendation from the medical device, or the medical device was operated in any other manner inconsistent with the treatment recommendation, this may be noted in the chronicle. When such information is included in the chronicle, recommendations may be made to the clinician on how to avoid the error in future procedures.

In addition, in some embodiments, the chronicle generation facility may include in the chronicle detailed information on a lesion and potential causes of the lesion, to aid a clinician in diagnosing the lesion. For example, while in some embodiments during a treatment a brief characterization of a lesion may be output (e.g., lesion is viscous), in a chronicle more detailed information on a composition may be output (e.g., lesion primarily composed of cholesterol). In addition, the chronicle generation facility may analyze the composition in context of a location of the lesion in the subject to determine whether the lesion was, for example, a result of an injury, a thrombus that developed at the site of the lesion, or an embolism that became stuck at the site of the lesion. For example, if the lesion is primarily composed of tissue like smooth muscle cell or atheroma, the lesion may have been a growth at the site following an injury. As another example, if the composition of the lesion indicated it formed in an area of the anatomy having a high shear stress, but the lesion is located at an area of the anatomy having a low shear stress, this may indicate the lesion was an embolism that became stuck at the site.

Once the chronicle has been generated in block 1606, the chronicle is output for presentation to a user (e.g., via a display, or stored to a memory or transmitted via a network), and the process 1600 ends.

EXAMPLES

Described below are various examples of scenarios in which medical devices and techniques may be used. It should be appreciated, however, that embodiments are not limited to operating in accordance with any one of these examples.

Example 1

One example of a way in which the techniques described herein may be used is with an invasive, smart guide wire. The invasive guide wire may be used in navigating the vascular system. Using sensors and analysis techniques described herein, the invasive guide wire may characterize tissue/materials with which it is in contact and communicate characteristics of this tissue/material to a clinician. The invasive guide wire may also help additional devices reach an intervention site within a patient.

In this example, the guide wire comprises a sensor (preferably an EIS sensor), an impedance spectrometer, and a handle. The guide wire may also include additional components that can be inserted along its length during use. The sensor may be used to sense and characterize properties of the tissue/material with which it is in contact. For example, the sensor may be used to determine tissue/material composition when used with the impedance spectrometer to perform high frequency impedance measurements. Both the sensor and the impedance spectrometer are preferentially located at an invasive tip of the guide wire so that tissue adjacent to the tip can be characterized without the need for long electric wires connecting sensor to the impedance spectrometer. This design may reduce electronic noise that may be otherwise inserted into electrical signals if the impedance spectrometer were located outside the subject.

The handle may contain additional components, such as those for communicating with the user, recording and transmitting data both during and after surgery, processing data, and powering the device. Examples of such components include a feedback unit such as a display or indicator light readable by a user, a unit for transmitting data either wirelessly or through a cable, a database, a processor, and a battery. The handle can be removable from the other device components; it can also be removably connected to circuitry on the guide wire itself.

Example 2

The guide wire described in Example 1 may be used by a clinician to determine an optimal treatment strategy for a patient experiencing a blocked artery. The clinician can use the guide wire to characterize the tissue/material that is blocking the artery and then choose between different possible treatments based on this information. In some embodiments, the guide wire may provide treatment recommendations to the clinician based upon one or more characterizations that it has performed and, optionally, based upon data from prior treatments performed with the aid of a guide wire.

In this example, the clinician can use the guide wire to assess and treat an arterial lesion. The clinician can begin by steering the guide wire to the site of the thrombus, optionally using the handle, and then penetrating the thrombus. Next, the clinician may use the guide wire to perform a measurement of the composition of the thrombus and/or of the tissue/material that is blocking the artery. The clinician can then determine an optimal treatment for the blocked artery based upon the results of this measurement. For example, the clinician may decide to use a stenting device if the blocking tissue is composed of cells from the arterial wall of the patient. If the blocking tissue is a thrombus, the clinician can instead decide to measure its viscoelastic properties and then determine whether to use an aspiration catheter or a stent to remove the clot on the basis of this information.

In some embodiments, the clinician may also receive a treatment recommendation from the guide wire. The treatment recommendation can be based upon the characterizations performed by the guide wire on the arterial lesion and/or based upon data collected during previous uses of a guide wire.

Upon conclusion of treatment, the clinician may remove the handle from the guide wire and insert the appropriate interventional device with the aid of the guide wire.

Example 3

An additional example of a device which may be used in accordance with the techniques described herein is a smart stent-retriever. The stent-retriever may be used to retrieve blood clots from a patient. Using sensors and analysis techniques described herein, the invasive stent-retriever may characterize a clot with which it is in contact and communicate characteristics of this tissue/material to a clinician.

In this example, the stent-retriever comprises at least one sensor (preferably at least one EIS sensor and/or EIT sensor), a measurement unit, and a handle. The stent-retriever may comprise multiple sensors at multiple strategic locations so that information regarding a blood clot with which it is in contact can be obtained from multiple locations within the clot. When a stent-retriever includes more than one sensor, the sensors may be able to sense different properties of the clot with which it is in contact. For example, the stent-retriever may comprise one or more sensors capable of sensing the integration of the clot with the stent-retriever, one or more sensors capable of sensing the position of the stent-retriever as a function of time, and/or one or more sensors capable of sensing the force applied to the clot. The integration of the stent-retriever with the clot may be determined by sensing the inductance and/or EIT signal of a stent as a function of time. Because the inductance and EIT values of the stent will vary with the expansion of the stent and the surrounding environment, constant values of these properties indicate that the stent has reached its maximal expansion and integration into the clot. A motion sensor may be used to sense the position of the stent-retriever as a function of time. This feature can enable the clinician to understand the movement of the stent-retriever within the patient and to determine the number of passes the stent-retriever has made during retrieval of a clot. Stress sensors may also be included to measure the force applied by the stent-retriever to a clot or tissue/material.

The measurement unit of the stent-retriever may be an impedance spectrometer and/or a tomography unit. This unit is preferentially located close to the tip of the stent-retriever so that a clot adjacent to the stent-retriever can be characterized without the need for long electric wires connecting sensor to the measurement unit. This design may reduce electronic noise that may be otherwise inserted into electrical signals if the impedance spectrometer were located outside the subject.

The handle may contain additional components as described in Example 1. It can also comprise a robotized pulling mechanism to allow accurate and automatized retrieval of the clot.

Example 4

The guide wire described in Example 1 and the stent-retriever described in Example 3 may be used together by a clinician to determine and execute an optimal treatment strategy for a patient experiencing a blocked artery. The clinician can use the guide wire to characterize the tissue/material that is blocking the artery and then use the stent-retriever to retrieve the clot and/or thrombus. Optionally, data can be collected during clot retrieval and uploaded to a database for later analysis.

In this example, a clinician can use a combination of smart devices to treat a patient experiencing a blocked artery. The clinician may begin by inserting the guide wire with a sheath and using the guide wire (with an invasive probe, as discussed above) to assess the lesion as described in Example 2. If the clinician decides to next use a stent-retriever based upon information and/or a recommendation provided by the guide wire, the clinician will remove the guide wire, leaving the sheath in place, and insert the stent-retriever along the sheath and steer it into the clot and/or thrombus. Once the stent penetrates the clot and/or thrombus, the sensors incorporated into the stent-retriever can sense aspects of the clot and/or thrombus and provide this information to the clinician as a function of time (e.g., on an external display). For example, the EIS and/or EIT sensors can characterize the integration of the stent with the clot and/or thrombus and the shape and composition of the clot and/or thrombus. The stent-retriever may also use data from prior clot and/or thrombus retrievals to provide treatment recommendations to the clinician. Treatment recommendations can include, for example, signals that integration of the stent-retriever with the clot and/or thrombus is optimal and/or recommendations regarding the appropriate speed and force with which to pull the clot and/or thrombus.

At this point, the clinician may act upon the information and/or recommendations provided by the stent-retrieve to retrieve the clot and/or thrombus. The clinician may decide to use an automatic pulling mechanism incorporated in the stent-retriever to retrieve the clot. The automatic pulling mechanism may then pull the clot and/or thrombus at a speed and using a force determined by the stent-retriever based upon data received from a database of prior clot and/or thrombus retrievals. If the clot and/or thrombus detaches from the stent retriever, the stent-retriever will signal the clinician using an alarm. The clinician may then penetrate the clot and/or thrombus once again and restart the retrieval process.

At the conclusion of the clot and/or thrombus retrieval, all the data collected during the intervention can be transferred to a database for later analysis.

Example 5

Another example of a device which may be used in accordance with the techniques described herein is a smart aspiration-catheter. The aspiration-catheter may be used to retrieve blood clots from a patient. Using sensors and analysis techniques described herein, the invasive aspiration-catheter may characterize a clot with which it is in contact and communicate characteristics of this tissue/material to a clinician.

In this example, the aspiration-catheter comprises at least one sensor (preferably at least one EIS sensor and/or EIT sensor), a measurement unit, and a handle. As in Example 3, the aspiration-catheter may comprise multiple sensors at multiple strategic locations so that information regarding a blood clot with which it is in contact can be obtained from multiple locations within the clot. When an aspiration-catheter includes more than one sensor, the sensors may be able to sense different properties of the clot with which it is in contact. For example, the aspiration-catheter may comprise one or more of the sensors described in Example 3 (i.e. one or more sensors capable of sensing the integration of the clot with the aspiration-catheter, one or more sensors capable of sensing the position of the aspiration-catheter as a function of time, and/or one or more sensors capable of sensing the force applied to the clot). The aspiration-catheter may also comprise an additional sensor capable of monitoring blood flow within the aspiration-catheter.

The measurement and the handle unit of the aspiration-catheter are identical to the measurement unit and handle of the stent-retriever described in Example 3.

Example 6

The guide wire described in Example 1 and the aspiration-catheter described in Example 5 may be used together by a clinician to determine and execute an optimal treatment strategy for a patient experiencing a blocked artery. The clinician can use the guide wire to characterize the tissue/material that is blocking the artery and then use the aspiration-catheter to retrieve the clot and/or thrombus. Optionally, data can be collected during clot retrieval and uploaded to a database for later analysis.

In this example, a clinician can use a combination of smart devices to treat a patient experiencing a blocked artery. The clinician may begin by inserting the guide wire and using it to assess the lesion as described in Example 2. If the clinician decides to next use an aspiration-catheter based upon information and/or a recommendation provided by the guide wire, the clinician will then insert the aspiration-catheter along the guide wire, steer it into the clot and/or thrombus, and begin the aspiration process. During aspiration of the clot and/or thrombus, an external display will provide information to the clinician regarding removal progress, the shape and composition of the clot and/or thrombus as sensed by the EIS and/or EIT sensors, and the passage of the clot and/or thrombus through the aspiration-catheter. The smart aspiration-catheter may determine also determine the optimal time to begin removal of the clot and/or thrombus based upon integration of the aspiration-catheter with the clot and signal this condition to the clinician. The clinician may then begin to remove the clot and/or thrombus. If the clot and/or thrombus detaches from the aspiration-catheter, the aspiration-catheter may signal the clinician using an alarm. The clinician may then penetrate the clot and/or thrombus once again and restart the retrieval process. When the sensors detect that the thrombus has been fully aspirated and passed along the tube of the aspirator, another message indicating successful removal may be generated and output.

At the conclusion of the clot and/or thrombus retrieval, all the data collected during the intervention can be transferred to a database for later analysis.

Example 7

The guide wire described in Example 1 may be used to treat a patient experiencing Chronic Total Occlusion (CTO). In this case, the patient's artery is blocked by an old and rigid thrombus that may be difficult for the clinician to penetrate in order to reestablish blood flow. The clinician may use the smart-guide wire to sense the position of the lesion and pass through the lesion. During operation, the guide wire can provide information to the clinician regarding when penetration of the lesion is initiated and when passage through the lesion to the lumen of the artery occurs. If the thrombus is too rigid to penetrate, the clinician can instead pass the guide wire through the arterial wall adjacent to the lesion. In this case, the guide wire can provide continuous information to the clinician regarding its position within the atheroma/plaque. This may help the clinician to avoid puncturing the vessel.

Example 8

The guide wire described in Example 1 may be used by a clinician in diagnosis and/or treatment of peripheral pathologies. Examples of peripheral pathologies include thrombi formed in deep veins or arteries, or thrombi formed in artificial veins or arteries. The guide wire may be used to determine an optimal treatment strategy for a patient experiencing a peripheral pathologies. The clinician can use the guide wire to characterize the tissue/material that is blocking the duct and then choose between different possible treatments based on this information. In some embodiments, the guide wire may provide treatment recommendations to the clinician based upon one or more characterizations that it has performed and, optionally, based upon data from prior treatments performed with the aid of a guide wire.

Example 9

As an additional example, any one of the foregoing invasive probes may be used to estimate the age of a clot (e.g., a thrombus). The age of the clot (i.e., the life of the clot since its formation) may be determined on the basis of one or more characteristics of the clot, such as the composition of the clot. Different treatments or combination of treatments may be provided based on the age of the clot, as determined from these characteristics. For example, one treatment may be recommended if the clot is less than fourteen days and a different treatment may be recommended if the clot is more than fourteen days.

Additionally, or alternatively, at least some of the devices and techniques described herein may be used to identify whether a biological structure is a healthy tissue. For example, the devices/techniques may be used to determine whether a wall of a vessel is healthy or whether an atheromatous plaque or a calcification has formed on the vessel wall. In such a case, a biological structure that is contacted by one of the devices described herein may be a vessel wall or an atheromatous plaque (or other lesion), and the techniques described herein may be used to determine whether it is one of those biological structures. Based on the identification, different treatment recommendations may be provided.

Methods of Operating a Medical Device for Use in Oncology

The inventor has recognized and appreciated that conventional techniques for examination of potentially cancerous cells are often unsatisfactory. For example, one conventional technique for examining potentially cancerous cells uses a needle to remove a tissue sample. To aid a clinician in guiding the insertion of the needle, conventional imaging systems such as x-ray, ultrasound, or magnetic resonant imaging (MRI) are used. However, images generated using these techniques are often inaccurate or blurred, thus making it difficult for the clinician to determine whether the needle is in contact with the cell or tissue being targeted. As a result, diagnosis and/or treatment of cancerous cells using such techniques is often inaccurate. As a result, when trying to determine whether a particular lesion is cancerous, a significant risk is that a needle intended to examine the potentially-cancerous lesion does not actually contact the lesion but instead contacts nearby healthy tissue, leading to an incorrect sample and incorrect medical conclusion. Similarly, when attempting to remove cancerous cells, two undesirable situations may arise: healthy tissues may be removed together with the cancerous cells, or some cancerous cells may be left unremoved.

Accordingly, in accordance with some embodiments described herein, a medical device may be used to determine the presence of a cancerous cell/tissue, the characteristics of a cancerous cell/tissue, and/or or the type of cancerous cell/tissue (e.g., carcinomas, lymphomas, myelomas, neoplasms, melanomas, metastases or sarcomas). For example, the machine learning techniques described above may be used to differentiate between cancerous cell/tissues and non-cancerous biological materials and/or to characterize cancerous cell/tissues. Furthermore, techniques of the type described herein (including machine learning techniques) may provide recommendations on how to treat a cancerous cell/tissue based, at least in part, on the characteristics of the cancerous cell/tissue. For example, ablation or removal of a cancerous cell/tissue may be recommended in some circumstances, as well as a manner in which to ablate or remove.

Examples of medical devices, sensors, and manners of sensing tissues/materials of a cancerous cell are described in detail above with respect to FIGS. 2-11. Described below in connection with FIGS. 31-33 are examples of techniques that may be implemented by such a medical device and/or that a medical device may be operated to perform.

Figure 22:
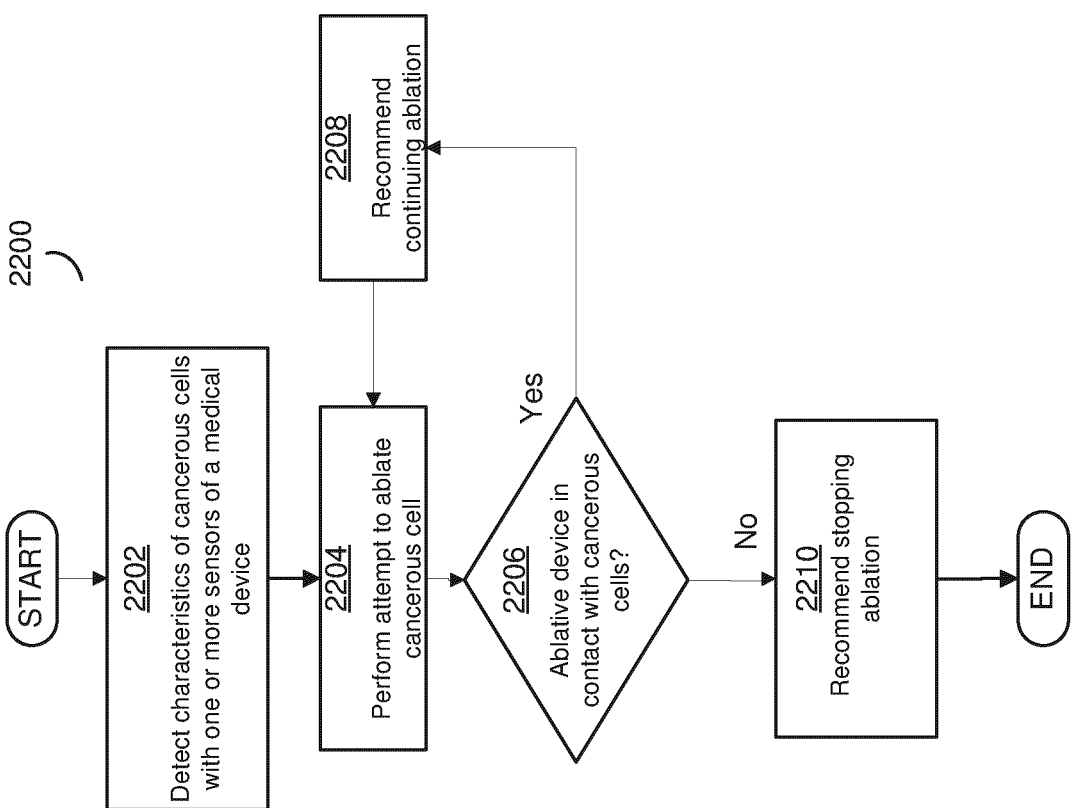
FIG. 22-24 are flowcharts of illustrative methods of some embodiments for operation of medical devices in accordance with embodiments described herein to generate treatment recommendations based in part on the characteristics of cancerous and/or noncancerous tissue.

FIG. 22 illustrates, an exemplary process 2200 that may be performed by a medical device operating in accordance with some techniques described herein. In the example of FIG. 22, the sensor may be disposed in diagnosis and/or treatment devices, such as in needles, ablation catheters, radiofrequency probes, robotic probes, laparoscopes, or cutting devices. In some embodiments, the sensor is disposed near the distal end of the medical device. The medical device may generate treatment recommendations based on characteristic(s) of the cancerous cell determined using the sensor. It should be appreciated that the processes described herein are not limited to use with invasive probes. In some embodiments, techniques described herein may be used with systems and devices that include non-invasive probes that may not be designed for use or solely for use within a body of an animal but may be additionally or alternatively be designed for use on biological structures, including tissues, on an exterior of an animal's body. For example, in some embodiments, devices, systems, and techniques described herein may be used for diagnosis and/or treatment of superficial lesions, such as skin cancer or other skin conditions.

The process 2200 begins in block 2202, in which an invasive probe of a medical device is operated to detect one or more characteristics (e.g., size and/or composition) of a lesion that is proximate to the sensor, which may be a cancerous tissue or cell. Prior to the start of the process 2200, the invasive probe may be inserted into the body of an animal and moved proximate to a predicted location of the lesion. The medical device then is operated to detect when the sensor contacts the lesion. Contact of the lesion, or of the tissue that is known to be or is potentially cancerous, may be determined by evaluating a change over time in a value output by the sensor (e.g., a change in impedance), or using machine learning techniques as described in connection with FIG. 17C. For example, the medical device may output (e.g., to a user, via a user interface) one result when the sensors of the invasive probe are not contacting a cancerous tissue/cell, or is not contacting the type of tissue of which the lesion is known to be a part.

For example, when the lesion to be investigated, as the invasive probe is moved through the animal toward the lesion, the medical device may output a value that is indicative of a tissue that it is contacting. The value may in some embodiments be a qualitative value, including a binary value such as a yes/no or true/false value to indicative whether the invasive probe is contacting the lesion.

The medical device may determine whether the invasive probe is contacting the lesion by analyzing the biological material(s) contacted by the invasive probe, including the tissues contacted by the invasive probe, to determine whether the invasive probe is contacting any biological materials that are "abnormal" and thus may be a part of a lesion. The medical device may, in some embodiments, determine whether a biological material contacted by the probe is "abnormal" by evaluating a location of the invasive probe within the animal, which may indicate biological materials that the invasive probe may be expected to contact.

The medical device may additionally or alternatively determine whether the invasive probe is contacting the lesion based on predictions about the lesion, which may be input by a clinician as a result of a preliminary diagnosis. For example, the clinician may input information preliminarily characterizing a lesion, such as whether the lesion is in vasculature or is a lesion of an organ, or in the case of a lesion of an organ what the organ is, a prediction of a composition of the lesion, or a prediction of a state of tissues or cells of the lesion (e.g., unhealthy, inflamed, cancerous, diseased, etc.). In embodiments in which such information is input, the clinician may input the information preliminarily characterizing the lesion individually, or may make a selection of a preliminary diagnosis of the lesion that may be associated with such information preliminarily characterizing the lesion (e.g., by selecting a particular category of atheroma, other information such as an expected composition of the atheroma and that it is located in vasculature may also be selected). As the invasive probe moves through the animal, the medical device may compare biological materials contacted by the invasive probe to the preliminary characterization of the lesion to determine whether the invasive probe is contacting the lesion. For example, if the lesion has been preliminarily diagnosed as a brain lesion that may be a brain tumor, the medical device may determine whether the invasive probe has contacted abnormal brain tissue and/or whether the invasive probe has contacted cancerous brain tissue, and output this result.

In other embodiments, rather than merely providing a binary value indicating whether the invasive probe is contacting the lesion, the medical device may output a value indicative of, for example, an identity, quantity and/or relative abundance of a biological material or biological materials being contacted by sensors of the invasive probe, which may vary as the probe moves through the body. The value indicative of the material(s) may be an identification of the materials, such as a list of materials identified from impedance spectra, as determined using techniques described herein (including the machine learning techniques described above). The values may, in other embodiments, be numeric values, such as values detected by sensors (e.g., an impedance value, or impedance spectrum) or other values.

The probe and its sensor may be moved until contacting a lesion, at which point a result output by the medical device may change once contact is made. In this manner, a location of a lesion may be determined using the invasive probe, and a determination may be made that the invasive probe is contacting the lesion.

The invasive probe may additionally, in some cases, be operated to determine the geometry of a lesion. For example, the geometry of a lesion potentially including cancerous tissue (e.g., a tumor) may be determined in some embodiments by moving the invasive probe in the proximity of the lesion and identifying when sensors of the invasive probe are or are not contacting the lesion. For example, if an analysis of values output by the invasive probe determines that the lesion includes cancerous tissue, the invasive probe may be moved and a determination made, over time, and for different sensors, of whether individual sensors are contacting cancerous tissue. The amount of movement of the invasive probe (e.g., measured using an accelerometer, as discussed above) and position of the sensors on the invasive probe may then be analyzed by the medical device to determine a geometry of the cancerous tissue within the animal, including one or more dimensions of the cancerous tissue.

In some such embodiments, the medical device may determine one or more treatment recommendations for a lesion based on the geometry of the lesion.

In one treatment protocol that may be implemented in embodiments such as the one illustrated in FIG. 22 ablation may be used as a first option for treatment of a cancerous tissue. Accordingly, in block 2204, an ablative device such as a needle or a radiofrequency probe is inserted into the animal. In some embodiments, the ablative device may include an invasive probe including sensors of the type described herein. The ablative device may be moved until the ablative device determines that contact with a cancerous cell or tissue has been formed. (Though, it should be appreciated that embodiments are not limited to operating with an ablative device that includes an invasive probe. In other embodiments, the invasive probe is part of a separate medical device, and after positioning of the invasive probe the ablative device is moved until located proximate to the invasive probe and thus located proximate to the cancerous cell/tissue.)

In block 2204, following placement of the ablative device proximate to the cancerous cell/tissues, the ablative device is operated to ablate the cancerous cell/tissue. Following a treatment time interval, the ablative device may be operated to determine whether the ablative device is having an effect on the cancerous cell/tissue. For example, in some embodiments, a treatment recommendation may be generated that guides a clinician in performing the ablation, including whether the ablation is effective and whether to continue with the ablation. Accordingly, in block 2206, the sensor may provide information indicating whether the ablative device is still in contact with cancerous cells or cancerous tissue. This determination may be made using techniques described herein (including the machine learning techniques described above). The information may be processed and may be used to provide a treatment recommendation, such as whether to stop the ablation or continue the ablation, or to check the positioning of the invasive probe before determining whether to stop ablating.

In some embodiments, the ablative device may include multiple different electrodes with which to ablate, such as different electrodes positioned at different locations, and the different electrodes may be individually operable, such that some may be operated to ablate at a time that others are not being operated to ablate. In some embodiments, each ablation electrode may be disposed near sensing electrodes, with the sensing electrodes being operated in accordance with techniques described herein to determine a biological material contacted by the sensing electrode. The ablative device may determine, using the sensing electrodes, whether a particular part of the ablative device is contacting cancerous tissue/cell or noncancerous tissue/cell. In some such embodiments, in response to determining that a part of the ablative device is contacting noncancerous tissue, the ablative device may cease or prevent operation of the ablative electrodes of that part of the ablative device, to limit ablation to only the cancerous tissues and minimize damage that may be done to noncancerous tissues.

In this way, the clinician may stop ablating if this treatment is ineffective, and the clinician may only continue ablating while the ablative device is in contact with the cancerous cell/tissue and thereby only ablate cancerous tissues. The clinician may thus be more confident at the end of the treatment of whether the treatment was successful and, if it was successful, that all of the cancerous cell/tissue has been ablated. In this way, the risk of ablating healthy tissues, and/or the risk of leaving cancerous cells un-ablated, is mitigated.

Accordingly, as illustrated in FIG. 22, if it is determined that the ablative device is still in contact with the cancerous cell/tissue, process 2200 proceeds to block 2208, in which a recommendation to continue to ablate is provided, and iterates to block 2204. Otherwise, if it is determined that the ablative probe is no longer in contact with the cancerous cell/tissue, a recommendation to stop the ablation is provided in block 2210. The process may be repeated by repositioning the ablative device. If contact can no longer be formed with a lesion even after several attempts to reposition the ablative device, process 2200 ends.

Figure 23:
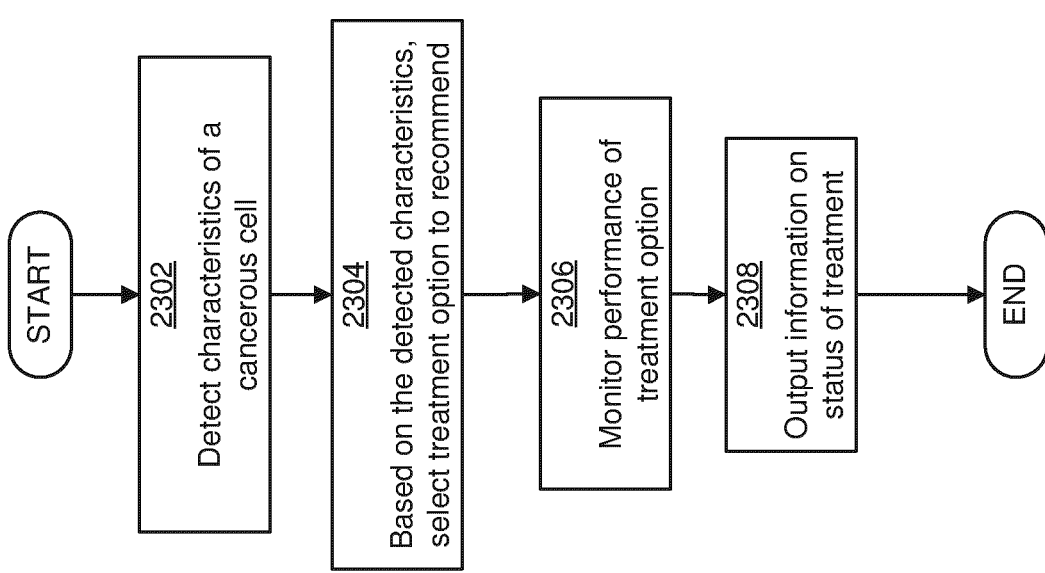

FIG. 23 illustrates an example of a manner of operating a medical device to generate treatment recommendations for a cancerous cell/tissue in accordance with another embodiment. In the embodiment of FIG. 23, a medical device may include multiple sensors arrayed along an exterior of a probe, such as in the example of FIG. 3 discussed above. As should be appreciated from the foregoing, with such an array of sensors, several different characteristics of a cancerous lesion may be determined, including composition of the cancerous lesion. For example, by performing an EIS process on the cancerous lesion, a composition of the cancerous lesion may be determined, as discussed above. In some embodiments, trained machine learning models as described above may be used to determine the composition or other characteristics of the cancerous lesion.

The process 2300 of FIG. 23 begins in block 2302, in which a medical device is inserted into the body of an animal subject and operated to detect one of more characteristics of a cancerous lesion, for example a composition of a cancerous lesion. Based on the characteristics, including the composition, the medical device may in block 2304 select a treatment option to recommend. Based on the composition, process 2300 may determine the type of cancerous lesion being probed, and an appropriate treatment recommendation may be provided. The medical device may be configured, such as in other embodiments described above, with information on impedance spectra and other electrical characteristics (e.g., effective capacitance) for different biological materials and on compositions of different lesions, such that biological materials may be identified using impedance spectra and lesions may be identified based on biological materials. The medical device may be further configured with different treatment recommendations for different types of lesions, such as different types of cancerous lesions. In one example, if it is determined using impedance spectra for different biological materials of the lesion that the cancerous lesion is or is a part of a carcinoma, a recommendation to remove the cancerous lesion may be provided. In another example, if is it determined that the cancerous lesion is part of a melanoma, radiofrequency ablation may be recommended. The medical device may select the treatment option in any suitable manner.

Once a treatment is recommended in block 2304, the medical device may in block 2306 monitor performance of the selected treatment option. The medical device may monitor the treatment using one or more sensors, such as the one or more sensors with which the characteristics were determined in block 2302 or one or more sensors of a treatment device that is operated to perform the treatment. For example, if ablation is recommended in block 2304, a clinician may insert an ablative device. The ablative device may have a sensor, such as a temperature sensor, for sensing the state of the cancerous lesion as ablation is being performed. The sensor may detect whether the ablation was successful by determining whether the cancerous lesion is burned or frozen.

In block 2308, information on a status of a treatment is output by the medical device via a user interface, for presentation to a clinician. Then, the process 2300 ends.

While an example of monitoring a treatment is given in the context of generating treatment recommendations, it should be appreciated that similar techniques may be used to raise error messages or other messages to a clinician regarding a status of a treatment. For example, if a sensor on a treatment device indicated presence of the cancerous lesion for a time, after which the sensor no longer detects the cancerous lesion, the medical device may determine that the treatment device is improperly positioned or that the cancerous lesion was lost. This may indicate either that the device needs to be repositioned or that the cancerous lesion has moved. A message to the clinician via the user interface may indicate such a potential problem.

Additionally, while the example of FIG. 23 described a manner of operating a medical device to provide treatment recommendations both relating to an initial selection of a treatment and related to a subsequent manner of performing that treatment, it should be appreciated from the foregoing that embodiments are not so limited. For example, in some embodiments, a medical device may include one or more sensors as described herein and may be operated to produce treatment recommendations on a manner of operation of that device, without generating an initial recommendation to use that device. For example, a needle or a radiofrequency probe, as discussed above, may include one or more sensors to generate data on a status or performance of a treatment and may produce treatment recommendations.

Figure 24:
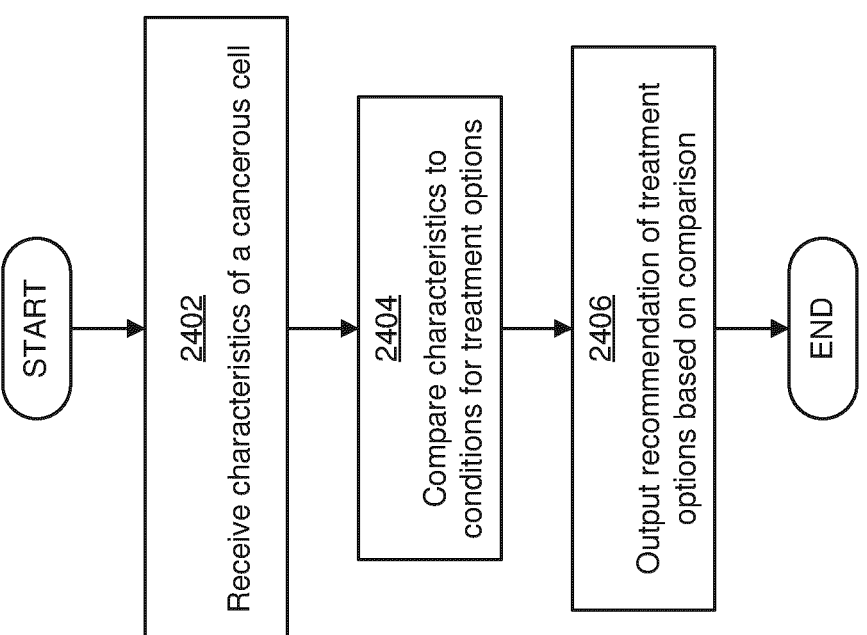

FIG. 24 illustrates a process 2400 that may be implemented by a medical device in some embodiments for generating treatment recommendations.

The process 2400 begins in block 2402, in which the medical device is operated to determine one or more characteristics (e.g., size and/or composition) of a cancerous lesion, using techniques described herein. The medical device may receive the characteristic(s) from a component of the medical device. For example, one or more sensors included in the medical device and/or another component that generates characteristic(s) based on data produced by the sensors. The characteristic(s) may include a composition of the cancerous lesion, in some embodiments. The characteristic(s) may additionally or alternatively include a location of the cancerous lesion within the body, one or more dimensions of an aggregate of cancerous lesion (e.g., a length, a thickness, etc.), a temperature of the cancerous lesion, or other information that may be determined based on the types of sensors described above.

In block 2404, the medical device compares the characteristic(s) received in block 2402 to one or more conditions for one or more treatment options. The medical device may be configured with information on multiple different available treatment options, each of which may be associated with one or more conditions that relate to one or more characteristics of a cancerous lesion. The treatment options may include ablation, removal, local dispensing of pharmaceuticals, occlusion of arteries feeding a lesion (e.g., a cancerous lesion), and biopsy (a diagnostic step, but which may be a part of an overall treatment regimen). Examples of such conditions related to a composition of a cancerous lesion are described above in connection with FIG. 23. Trained machine learning models, for example as described in connection with FIG. 15B, may be used to determine relationships between cancerous lesion characteristics and options for successful treatments.

The medical device may compare the characteristic(s) of the cancerous lesion to the conditions for one or more treatment options to determine which conditions are met. In some embodiments, the sets of conditions for treatment options may be mutually exclusive, such that a cancerous lesion may meet only one set of conditions and thus only one treatment option may be selected. In other embodiments, the set of conditions may not be mutually exclusive, and the medical device may determine which treatment option to recommend by identifying the one for which the most corresponding conditions are met or the one for which the corresponding conditions are met most closely. For example, in the case that different conditions are associated with different ranges of values, such as ranges of impedance spectra, a condition may be determined by identifying a range for which a value for a lesion most closely matches. The closest match may be the range, for example, that the lesion's impedance spectrum or other value falls within or is the farthest from a boundary value for the range, or has the most overlap with the range.

In block 2406, based on the comparison, the medical device may output a recommendation of a treatment option via a user interface of the medical device, and the process 2400 ends.

Those skilled in the art will appreciate that there are a number of ways in which to set the conditions for treatment options that may be used in connection with a process like process 2400 of FIG. 24. For example, values for characteristics of a cancerous lesion to use as conditions for selection of treatment options may be hard-coded into a medical device following at least some experimentation to determine a correspondence between the values, types of cancerous cells/tissues, and successful treatment with various treatment options. The inventor has recognized and appreciated, however, the advantages of a system to learn such relationships and conditions based on characteristics of cancerous cells/tissues and information on successful treatments of cancerous cells/tissues, among other information. For example, a machine learning process, such as one that may include feature extraction and/or classification, may be implemented in some embodiments.

Computer Implementation

Techniques operating according to the principles described herein may be implemented in any suitable manner. Included in the discussion above are a series of flow charts showing the steps and acts of various processes that characterize a lesion of a duct and/or generate one or more treatment recommendations for treatment of the lesion. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), Blu-Ray disk, a persistent or non-persistent solid-state memory (e.g., Flash memory, Magnetic RAM, etc.), or any other suitable storage media. Such a computer-readable medium may be implemented in any suitable manner, including as computer-readable storage media 1706 of FIG. 17 described below (i.e., as a portion of a computing device 1700) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 17:
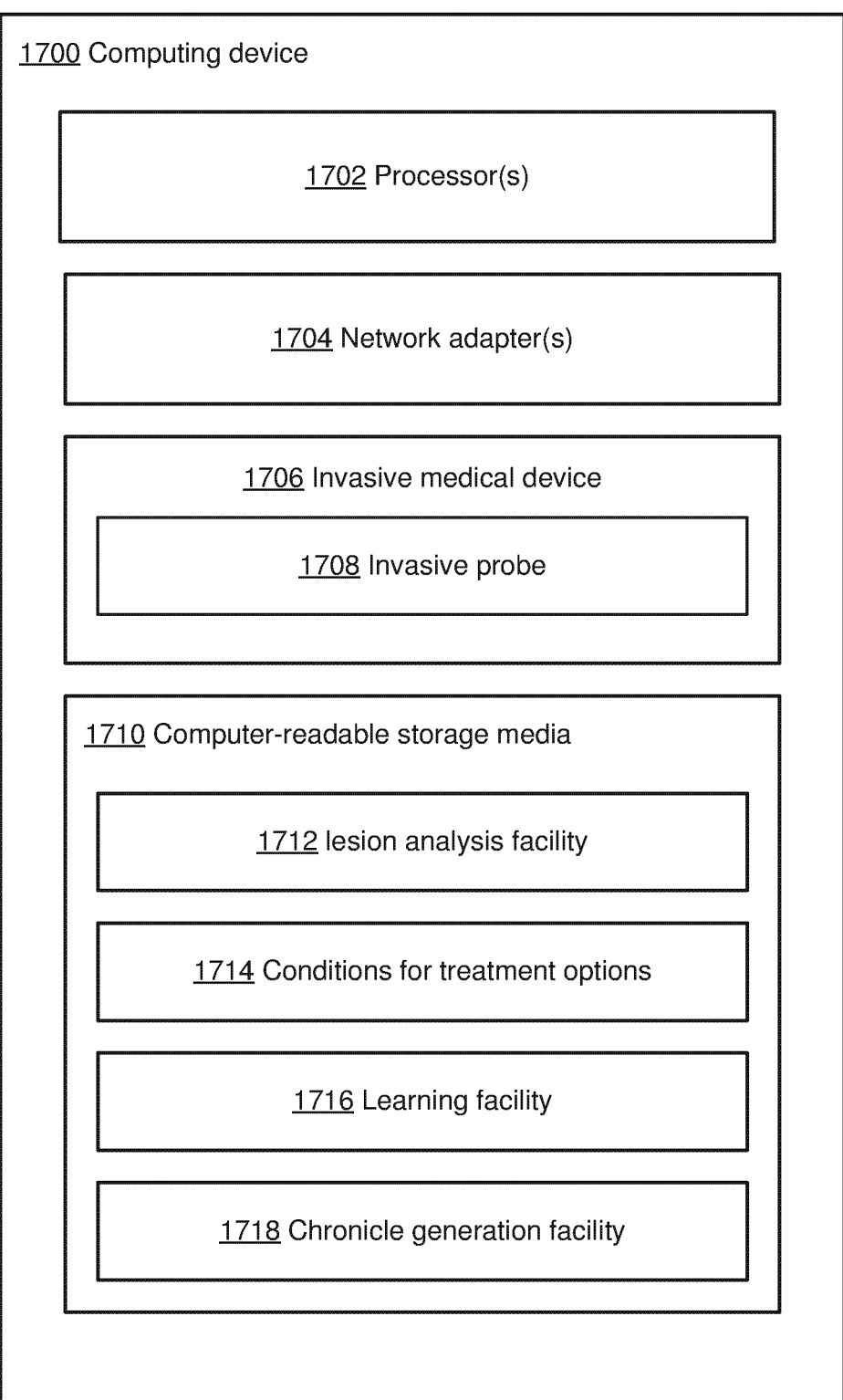
FIG. 17 is a block diagram of a computing device with which some embodiments may operate.

FIG. 17 illustrates one exemplary implementation of a computing device in the form of a computing device 1700 that may be used in a system implementing techniques described herein, although others are possible. It should be appreciated that FIG. 17 is intended neither to be a depiction of necessary components for a computing device to operate in accordance with the principles described herein, nor a comprehensive depiction.

Computing device 1700 may comprise at least one processor 1702, a network adapter 1704, and computer-readable storage media 1710. Computing device 1700 may be, for example, a medical device as described above, a desktop or laptop personal computer, a personal digital assistant (PDA), a smart mobile phone, a server, or any other suitable computing device. Network adapter 1704 may be any suitable hardware and/or software to enable the computing device 1700 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1710 may be adapted to store data to be processed and/or instructions to be executed by processor 1702. Processor 1702 enables processing of data and execution of instructions. The data and instructions may be stored on the computer-readable storage media 1710.

In embodiments in which the device 1700 is a medical device as described herein, the device 1700 may include an invasive medical device 1706 that is to be inserted into anatomy of a subject to diagnose and/or treat the subject. The device 1706 includes an invasive probe 1708, as discussed above.

The data and instructions stored on computer-readable storage media 1710 may comprise computer-executable instructions implementing techniques which operate according to the principles described herein. In the example of FIG. 17, computer-readable storage media 1710 stores computer-executable instructions implementing various facilities and storing various information as described above. Computer-readable storage media 1710 may store a lesion analysis facility 1712 to analyze one or more characteristics of a lesion, including a composition of a lesion, and/or to determine a treatment recommendation based on the analysis. The computer-readable storage media 1710 may additionally store conditions 1714 for treatment options that may be used by the facility 1712. The computer-readable storage media 1710 may also store a learning facility 1716 and a chronicle generation facility 1718.

While not illustrated in FIG. 17, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising." "having." "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

The terms "approximately", "substantially," and "about" may be used to mean within ±20% of a target value in some embodiments, within ±10% of a target value in some embodiments, within ±5% of a target value in some embodiments, and within ±2% of a target value in some embodiments. The terms "approximately" and "about" may include the target value. Having thus described several aspects of at least one embodiment, it is to be appreciated that various alterations, modifications, and improvements will readily occur to those skilled in the art. Such alterations, modifications, and improvements are intended to be part of this disclosure, and are intended to be within the scope of the principles described herein. Accordingly, the foregoing description and drawings are by way of example only.

The invention claimed is:

1. A circuit board for use with an invasive probe to be inserted into a duct of an animal, the circuit board comprising:
  a first region, comprising:
    an interconnect layer,
    a first polymer layer disposed on a first side of the interconnect layer, and
    a second polymer layer disposed on a second side of the interconnect layer opposite the first side; and
  a second region, comprising:
    one or more integrated circuits,
    the interconnect layer connected to the one or more integrated circuits,
    the first polymer layer disposed on the first side of the interconnect layer and the one or more integrated circuit, and
    the second polymer layer disposed on the second side of the interconnect layer and the one or more integrated circuit, opposite the first side;
  wherein in the first region a first thickness of the first polymer layer matches a second thickness of the second polymer layer, and wherein a first flexibility of the first region is greater than a second flexibility of the second region.

2. A circuit board according to claim 1, wherein the one or more integrated circuits include:

a first integrated circuit arranged to operate one or more sensors to sense one or more values, and a second integrated circuit electrically connected to the first integrated circuit and comprising one or more circuits to be operated by the first integrated circuit.

3. An invasive probe comprising:

a housing;

one or more electrical components; and a circuit board according to claim 1, the circuit board being at least partially disposed within the housing, wherein the one or more electrical components are mounted on the circuit board, and wherein the circuit board comprises:

a region of the circuit board that extends from the housing comprising two or more conductive contacts disposed outside of the housing, the two or more conductive contacts comprising a first contact and a second contact, at least one interconnect layer to electrically connect the two or more conductive contacts to the one or more electrical components, wherein a first wire is electrically connected to the first contact disposed outside of the housing, and wherein a second wire is electrically connected to the second contact disposed outside of the housing.

4. The invasive probe of claim 3, wherein:

the housing is an inflexible housing;

the invasive probe further comprises at least one additional wire;

the two or more conductive contacts are three or more conductive contacts and comprise one or more additional conductive contacts disposed outside of the inflexible housing;

the first wire, the second wire, and the at least one additional wire are joined in a ribbon, wherein the first wire, the second wire, and each of the at least one additional wires are electrically isolated from other wires of the ribbon and each wire of the ribbon is electrically connected to one conductive contact of the three or more conductive contacts.

5. The invasive probe of claim 4, wherein:

each wire of the ribbon comprises an insulating jacket that electrically isolates the wire in the ribbon; and for each wire of the ribbon that is electrically connected to one conductive contact of the three or more conductive contacts of circuit board, the insulating jacket of the wire contacts the other conductive contacts of the three or more conductive contacts of the circuit board.

6. The invasive probe of claim 5, wherein:

the three or more conductive contacts of the circuit board are distributed outside the inflexible housing across the region of the circuit board that extends from the inflexible housing;

each wire of the ribbon includes an aperture in an associated insulating jacket of the wire at a position corresponding to a position of a conductive contact of the three or more conductive contacts to which the wire is electrically connected; and the invasive probe further comprises three or more regions of a conducting material joining the ribbon to the circuit board, the three or more regions of the conductive material respectively positioned on the circuit board at positions corresponding to positions of each of the three or more conductive contacts.

7. The invasive probe of claim 6, wherein:

the circuit board is flexible;

the ribbon is flexible; and the three or more regions of the conducting material form three or more regions of inflexibility where each is positioned on the circuit board.

8. The invasive probe of claim 3, further comprising an insulating glue disposed proximate an area where the first wire, the second wire, and/or additional wires are electrically connected to the first contact, the second contact, and/or additional conductive contacts.

9. The invasive probe according to claim 3, the invasive probe being a guidewire comprising a core wire made in an electrically conductive material, each of the first wire, the second wire, and/or additional wires being arranged on an external surface of the core wire, the core wire being connected to a potential reference.

10. The invasive probe of claim 9, further comprising a filar coil comprising one or more filaments configured to transfer torque from a user of the probe along a length of the probe.

11. The invasive probe of claim 10, wherein the filar coil is comprised of between 2 filaments and 10 filaments.

12. The invasive probe of claim 10, wherein the filar coil is configured to adjust a stiffness of the guidewire by adjusting spacing between the filaments.

13. The invasive probe according to claim 3, wherein the first wire, the second wire, and/or additional wires include at least one of a ground wire and a positive potential wire for feeding electric power to the circuit board, and a signal-carrying wire for providing, to the circuit board, a time-dependent signal, the signal-carrying wire being arranged between the ground wire and the positive potential wire.

14. The invasive probe according to claim 3, wherein at least one integrated circuit is configured to implement a digital communication protocol by feeding a digital time-dependent signal through at least one of the first wire, the second wire, and/or additional wires.

15. The invasive probe according to claim 3, wherein the first region radially surrounds at least a portion of the second region with respect to a longitudinal direction of the housing.

16. The invasive probe of claim 3, further comprising a sensor array.

17. The invasive probe of claim 16, wherein the sensor array comprises one or more presser and/or flow sensors.

18. A method of fabricating an invasive probe according to claim 3, wherein the housing includes a slot, the method comprising:

positioning a flexible circuit board according to claim 1, with respect to the housing, wherein the positioning comprises positioning the second region of the flexible circuit board within the slot of the housing; and wrapping the first region of the flexible circuit board around the housing with the second region positioned within the slot.

19. The method of claim 18, wherein wrapping the first region around the housing comprises applying a consistent pressure to the first region before and/or during the wrapping.

20. The method of claim 18, further comprising:

joining each of the wires of the invasive probe to a respective conductive contact of the conductive contacts of the invasive probe, wherein the conductive contacts are formed on the flexible circuit board of the invasive probe, the flexible circuit board being partially disposed within the housing and the conductive contacts being disposed outside of the housing.

* * * * *